US012409339B2

(12) United States Patent
Rezaie et al.

(10) Patent No.: US 12,409,339 B2
(45) Date of Patent: *Sep. 9, 2025

(54) INTERNAL ULTRAVIOLET THERAPY

(71) Applicant: CEDARS-SINAI MEDICAL CENTER, Los Angeles, CA (US)

(72) Inventors: Ali Rezaie, Beverly Hills, CA (US);
Mark Pimentel, Los Angeles, CA (US);
Gil Y. Melmed, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 351 days.

This patent is subject to a terminal disclaimer.

(21) Appl. No.: 18/020,847

(22) PCT Filed: Aug. 13, 2021

(86) PCT No.: PCT/US2021/046011
§ 371 (c)(1),
(2) Date: Feb. 10, 2023

(87) PCT Pub. No.: WO2022/036263
PCT Pub. Date: Feb. 17, 2022

(65) Prior Publication Data
US 2023/0302292 A1 Sep. 28, 2023

Related U.S. Application Data

(60) Provisional application No. 63/065,167, filed on Aug. 13, 2020.

(51) Int. Cl.
*A61N 5/06* (2006.01)
*A61N 5/00* (2006.01)

(52) U.S. Cl.
CPC ......... *A61N 5/0624* (2013.01); *A61N 5/0601* (2013.01); *A61N 2005/002* (2013.01);
(Continued)

(58) Field of Classification Search
CPC ................ A61N 5/0624; A61N 5/0601; A61N 2005/002; A61N 2005/0651;
(Continued)

(56) References Cited

U.S. PATENT DOCUMENTS 5,053,033 A 10/1991 Clarke
5,573,531 A 11/1996 Gregory
(Continued)

FOREIGN PATENT DOCUMENTS

AU 2017273699 A1 12/2018
CA 2515304 A1 2/2004
(Continued)

OTHER PUBLICATIONS

International Search Report and Written Opinion for PCT/US2017/035316 dated Oct. 2, 2017,.
(Continued)

*Primary Examiner* — Jonathan T Kuo
(74) *Attorney, Agent, or Firm* — Nixon Peabody LLP

(57) ABSTRACT

Methods and systems one or more for performing intraluminal ultraviolet therapy for treating and/or ameliorating a gastrointestinal tract inflammation and/or infection are provided. In one example, a light delivery catheter may include a light emitting portion and non-illuminating portion, wherein the light emitting portion may include one or more UV transparent balloons. In some examples, the UV light source is configured to emit narrow-band light having wavelengths in a range between 335 nm and 349 nm.

30 Claims, 42 Drawing Sheets

(52) U.S. Cl.
CPC ............... *A61N 2005/0651* (2013.01); *A61N 2005/0661* (2013.01)

(58) Field of Classification Search
CPC .... A61N 2005/0661; A61N 2005/0602; A61N 2005/0609; A61N 5/06–2005/073; A61B 2018/00285; A61B 2018/00494; A61B 2018/00815
See application file for complete search history.

(56) References Cited

U.S. PATENT DOCUMENTS

| | | | |
|---|---|---|---|
| 5,855,203 A | 1/1999 | Matter | |
| 6,316,872 B1 | 11/2001 | Ge et al. | |
| 6,890,346 B2* | 5/2005 | Ganz | H01J 35/32 607/94 |
| 7,311,722 B2 | 12/2007 | Larsen | |
| 7,409,954 B2 | 8/2008 | Dobkine et al. | |
| 9,014,789 B2* | 4/2015 | Mercader | A61B 1/0676 600/407 |
| 9,023,092 B2 | 5/2015 | Natale et al. | |
| 9,820,798 B2 | 11/2017 | Schwartz | |
| 10,004,918 B2 | 6/2018 | Klang | |
| 10,357,661 B2 | 7/2019 | Hellstrom et al. | |
| 10,842,567 B2 | 11/2020 | Grace et al. | |
| 11,179,575 B2 | 11/2021 | Rezaie et al. | |
| 11,318,325 B2 | 5/2022 | Rezaie et al. | |
| 11,571,586 B2* | 2/2023 | Xu | A61N 5/0616 |
| 11,992,699 B2* | 5/2024 | Rezaie | A61N 5/0603 |
| 2002/0120358 A1 | 8/2002 | Lalonde | |
| 2003/0191459 A1* | 10/2003 | Ganz | H01J 35/32 600/101 |
| 2004/0232359 A1 | 11/2004 | Fiset | |
| 2005/0070759 A1 | 3/2005 | Armstrong | |
| 2005/0075703 A1 | 4/2005 | Larsen | |
| 2005/0106710 A1 | 5/2005 | Friedman et al. | |
| 2005/0107853 A1 | 5/2005 | Krespi et al. | |
| 2005/0177208 A1 | 8/2005 | Irwin | |
| 2006/0047329 A1 | 3/2006 | Krespi et al. | |
| 2006/0069314 A1 | 3/2006 | Farr | |
| 2006/0127531 A1 | 6/2006 | Jobe | |
| 2006/0130846 A1 | 6/2006 | Rife | |
| 2006/0167531 A1 | 7/2006 | Gertner et al. | |
| 2006/0183987 A1 | 8/2006 | Murray | |
| 2006/0217787 A1 | 9/2006 | Olson | |
| 2007/0135874 A1 | 6/2007 | Bala | |
| 2008/0033519 A1 | 2/2008 | Burwell | |
| 2008/0073565 A1 | 3/2008 | Jeon | |
| 2008/0159908 A1 | 7/2008 | Redmond | |
| 2008/0194973 A1 | 8/2008 | Imam | |
| 2008/0257355 A1 | 10/2008 | Rao et al. | |
| 2009/0179547 A1 | 7/2009 | Auday | |
| 2009/0216177 A1 | 8/2009 | Akiyama et al. | |
| 2009/0287137 A1 | 11/2009 | Crowley | |
| 2010/0220472 A1 | 9/2010 | Dahm | |
| 2010/0241198 A1 | 9/2010 | Klepper | |
| 2011/0084275 A1 | 4/2011 | Yamamuro et al. | |
| 2011/0226966 A1 | 9/2011 | Takahashi et al. | |
| 2011/0313299 A1* | 12/2011 | Brennan, III | A61B 5/02007 600/478 |
| 2012/0004710 A1 | 1/2012 | Kerber | |
| 2012/0321509 A1* | 12/2012 | Bak | A61M 39/16 250/435 |
| 2013/0102862 A1* | 4/2013 | Mercader | A61B 1/0676 600/317 |
| 2013/0104884 A1 | 5/2013 | Vazales | |
| 2013/0178788 A1 | 7/2013 | Jaquins-Gerstl | |
| 2013/0261368 A1 | 10/2013 | Schwartz | |
| 2013/0274549 A1 | 10/2013 | Natale et al. | |
| 2014/0150782 A1 | 6/2014 | Vazales | |
| 2014/0235942 A1 | 8/2014 | Hellstrom et al. | |
| 2015/0209457 A1 | 7/2015 | Bonutti et al. | |
| 2015/0359595 A1* | 12/2015 | Ben Oren | A61B 18/1492 606/41 |
| 2016/0008624 A1 | 1/2016 | Grossman | |
| 2016/0038621 A1 | 2/2016 | Victor et al. | |
| 2016/0114185 A1 | 4/2016 | Mankin | |
| 2016/0128767 A1 | 5/2016 | Azamian | |
| 2016/0151639 A1 | 6/2016 | Scharf et al. | |
| 2017/0265942 A1 | 9/2017 | Grace et al. | |
| 2017/0281966 A1 | 10/2017 | Basiony | |
| 2019/0168023 A1 | 6/2019 | Eltorai | |
| 2019/0175938 A1 | 6/2019 | Rezaie et al. | |
| 2020/0030473 A1* | 1/2020 | Sugimoto | A61N 5/0624 |
| 2020/0046835 A1 | 2/2020 | Kamaev et al. | |
| 2020/0121943 A1* | 4/2020 | Anderson | A61N 5/0603 |
| 2020/0147409 A1 | 5/2020 | Basiony | |
| 2020/0346032 A1 | 11/2020 | Rezaie et al. | |
| 2021/0106844 A1 | 4/2021 | Rezaie et al. | |
| 2021/0205632 A1* | 7/2021 | Xu | A61N 5/0601 |
| 2022/0040497 A1 | 2/2022 | Rezaie | |
| 2023/0035292 A1 | 2/2023 | Rezaie et al. | |
| 2023/0147752 A1 | 5/2023 | Rezaie et al. | |
| 2024/0024697 A1 | 1/2024 | Rezaie et al. | |
| 2024/0198131 A1 | 6/2024 | Pimentel et al. | |
| 2024/0366960 A1 | 11/2024 | Rezaie et al. | |

FOREIGN PATENT DOCUMENTS

| | | |
|---|---|---|
| CA | 3024711 A1 | 12/2017 |
| CN | 1646191 A | 7/2005 |
| CN | 109414591 A | 3/2019 |
| EP | 3463570 A1 | 4/2019 |
| EP | 3893993 | 10/2021 |
| HK | 40001485 A | 2/2020 |
| IN | 201827043869 A | 10/2019 |
| JP | 2000285854 A | 10/2000 |
| JP | 2007-511286 A | 5/2007 |
| JP | 2007511279 A | 5/2007 |
| JP | 2008528188 A | 7/2008 |
| JP | 2009505365 A | 2/2009 |
| JP | 2011530327 A | 12/2011 |
| JP | 2014-233712 A | 12/2014 |
| JP | 2015505678 A1 | 2/2015 |
| JP | 2019517305 A | 6/2019 |
| KR | 20190015357 A | 2/2019 |
| MX | 2018014694 A | 5/2019 |
| NZ | 748479 A | 10/2021 |
| SG | 11201810515 T | 12/2018 |
| WO | 2010/029292 A1 | 3/2010 |
| WO | 2010058607 A1 | 5/2010 |
| WO | 2011083381 A1 | 7/2011 |
| WO | 2014022867 A1 | 2/2014 |
| WO | 2014165854 A1 | 10/2014 |
| WO | 2017/210366 A1 | 12/2017 |
| WO | 2021076399 A1 | 4/2021 |
| WO | 2021189020 A1 | 9/2021 |
| WO | 2021202402 A1 | 10/2021 |
| WO | 2022036263 A1 | 2/2022 |
| WO | 2022235966 A1 | 11/2022 |

OTHER PUBLICATIONS

European Supplementary Search Report for EP17807445.6 dated Feb. 26, 2020, 14 pages.
Extended European Search Report or EP17807445.6 dated Jun. 25, 2020, 13 pages.
SR and WO for PCT/US20/054758 dated Jan. 11, 2021, 9 pages.
JP Notice of Reasons for Rejection for JP2018-562598 dated Nov, 2, 2020, 16 pages.
NZ Examination Report for App No. 748479 Oct. 14, 2020, 5 pages.
NZ Examination Report for App No. 748479 Mar. 24, 2021, 4 pages.
Hamamoto et al., New water disinfection system using UVA light-emitting diodes, Journal of Applied Microbiology, Aug. 30, 2007, vol. 103:6: 2291-2298.
Aihara, et al., Vegetable surface Sterilization system using UVA Light-Emitting Diodes, Journal of Medical Invesstigation, Sep. 27, 2014, vol. 61, pp. 285-290.
SG Written Opinion for 11201810515T dated Mar. 2, 2020, 4 pages.

(56) References Cited

OTHER PUBLICATIONS

SG Written Opinion for 11201810515T dated Jan. 20, 2021, 7 pages.
Wikipedia, Inverse-square law, 2021; https://en.wikipedia.org/wiki/inverse-square_law#Light_and_other_electromagnetic_radiation (Year: 2021).
Extended European Search Report for EP 20877251.7 dated Jan. 21, 2022, 6 pages.
ISR-WO for PCT/US2021/023354 dated Jun. 30, 2021, 9 pages.
European Centre for Disease Prevention and Control, Outbreak of severe acute respiratory syndrome coronavirus 2 (SARS-COV-2): increased transmission beyond China—fourth update, Feb. 14, 2020 [retrieved May 26, 2021], retrieved from the internet: <URL: https://www.ecdc.europa.eu/sites/default/files/documents/SARS-COV-2-risk-assessment-14-feb-2020.pdf>, pp. 1-12.
Pekmezovic et al., Candida pathogens induce protective mitochondria-associated type I interferon signalling and a damage-driven response in vaginal epithelial cells, Nature Microbiology, 2021, pp. 643-657.
SR-WO for PCT/US2021/046011 dated Nov. 17, 2021, 10 pages.
JP Notice of Reasons for Rejection for JP2018-562598 dated Jul. 7, 2022, 5 pages.
PRP for PCT/US20/054758 dated Apr. 19, 2022, 9 pages.
European Search Report for EP21771541.6 dated Apr. 19, 2024, 7 pages.
SESR for 21856823.6 dated Apr. 20, 2024, 8 pages.
CA Exam Report for 3,172,543 dated Nov. 29, 2024, 4 pages.
Notice of Reasons for Rejection for JP 2023-509643 dated May 1, 2025, 15 pages (with translation).
IL Office Action for IL 263062, Mar. 26, 2025, 17 pages.

\* cited by examiner

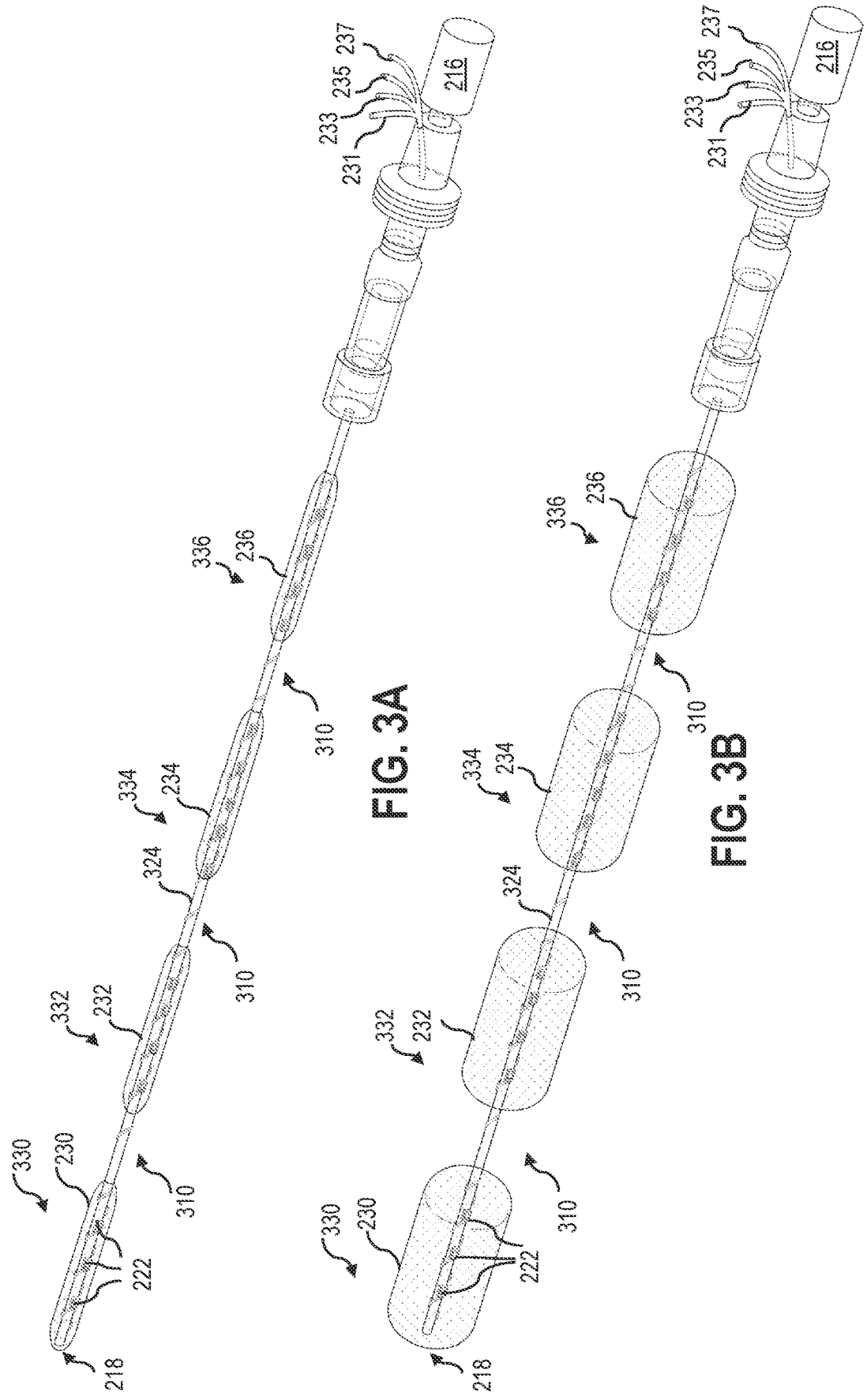

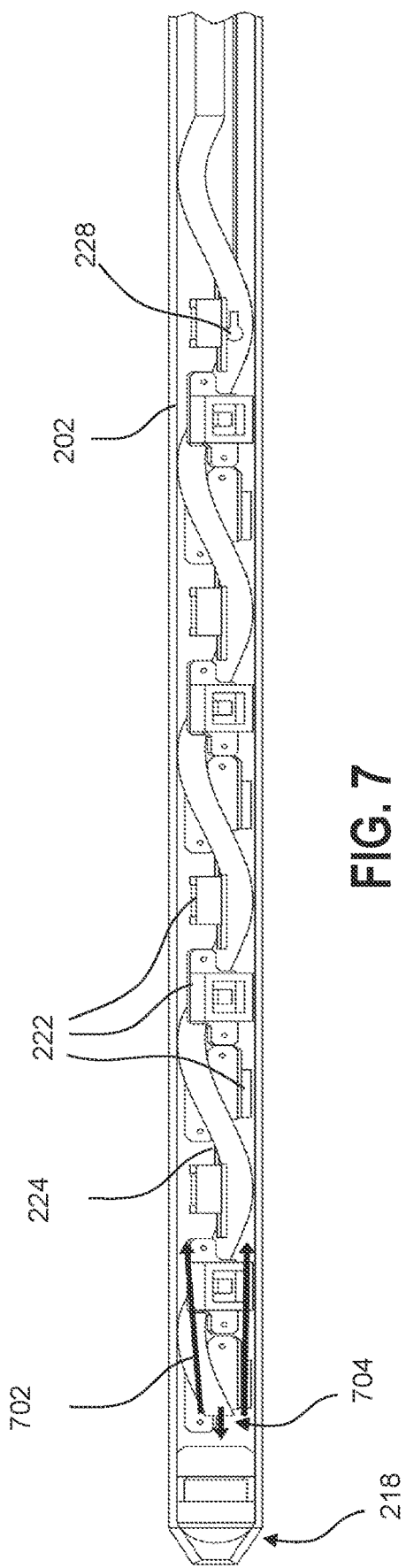
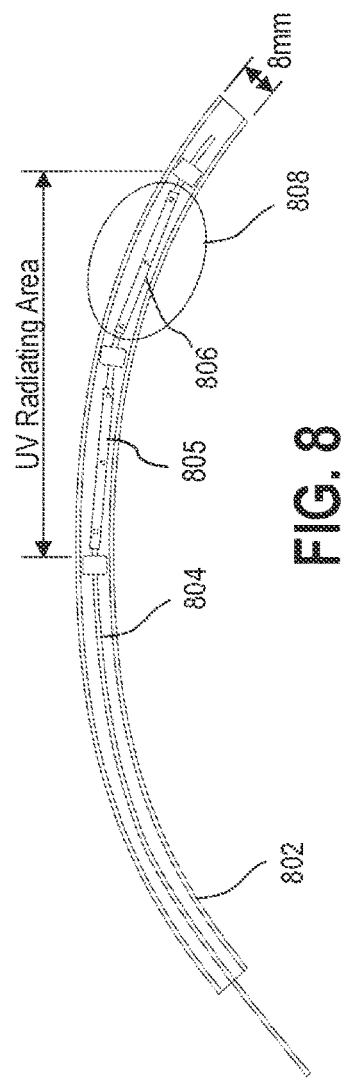
FIG. 7
FIG. 8

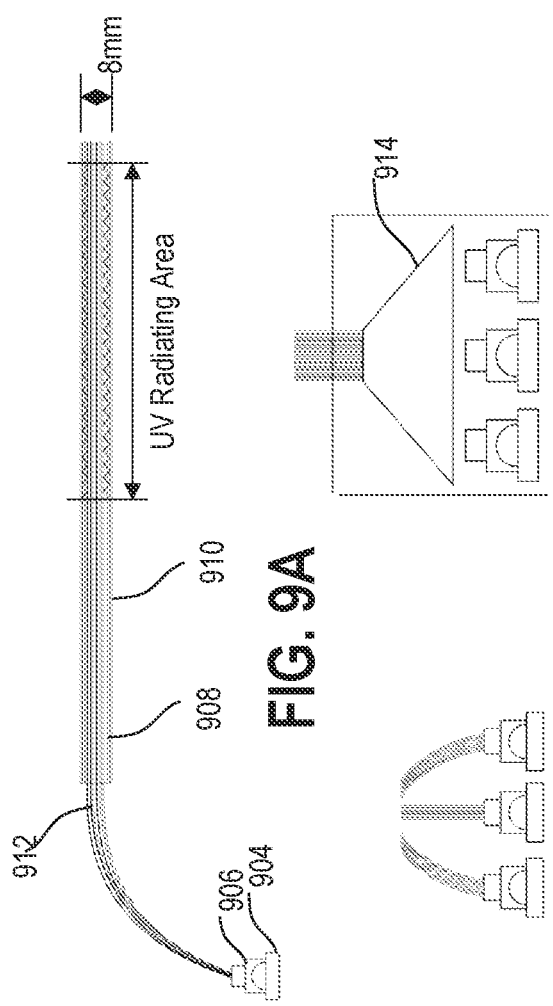

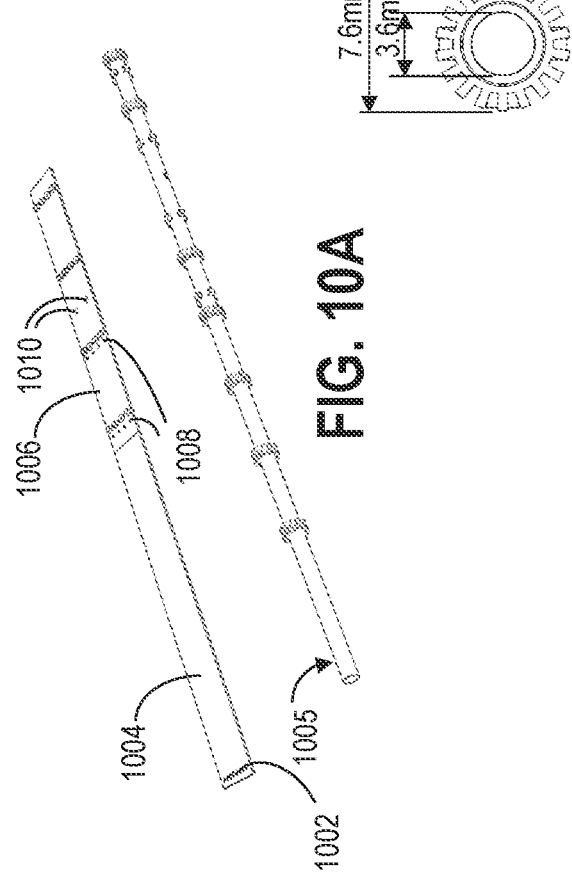

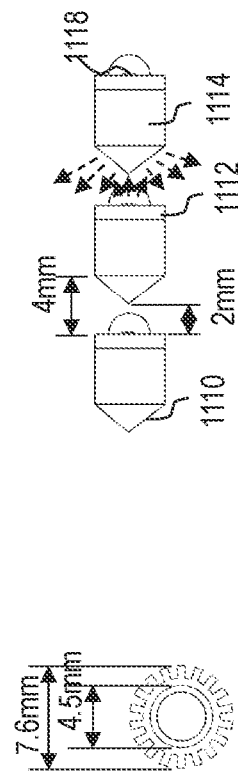
FIG. 11A
FIG. 11B
FIG. 11C

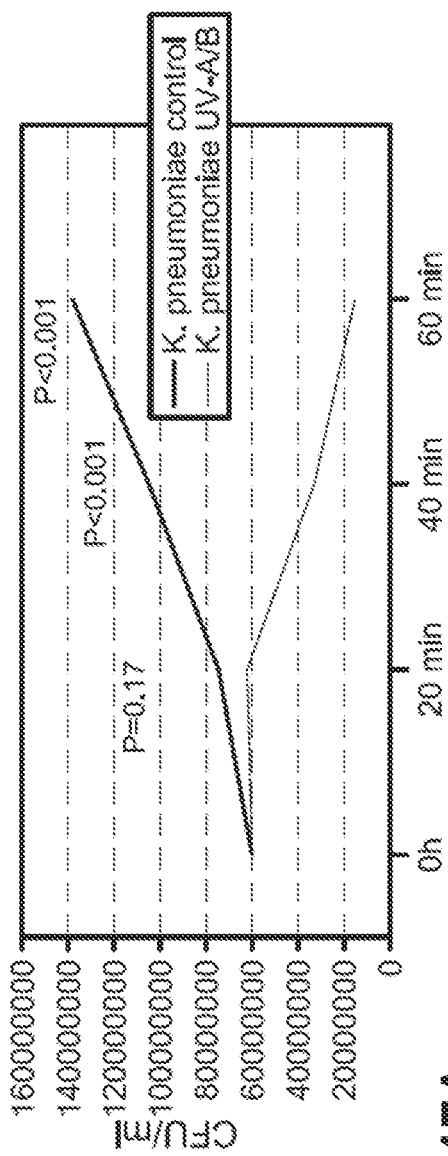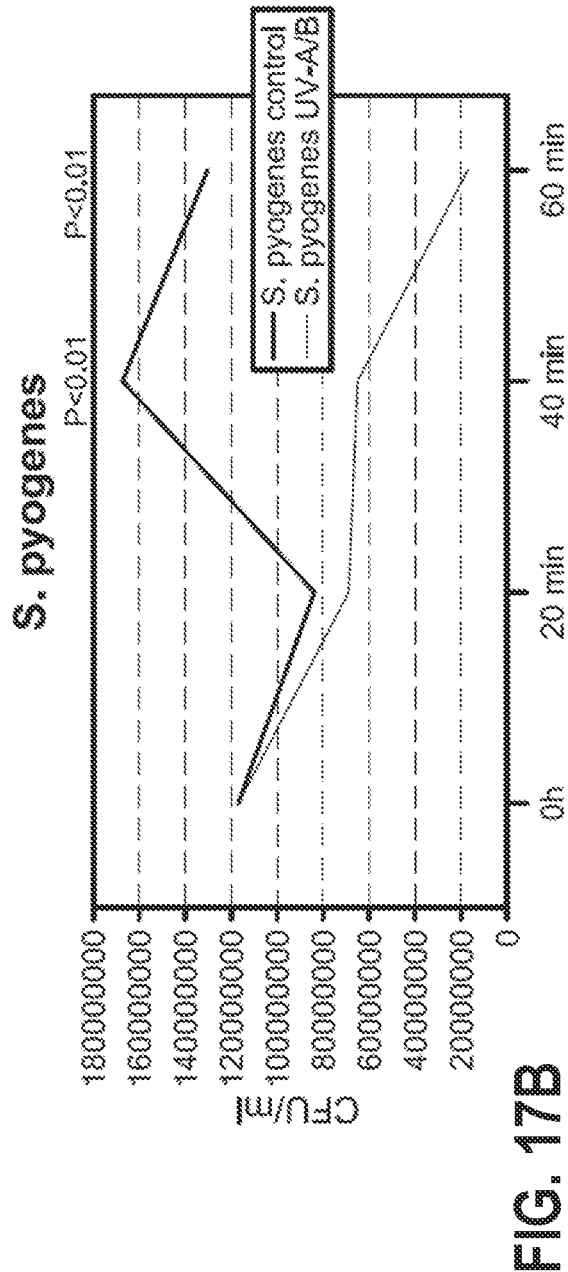
FIG. 17A
FIG. 17B

FIG. 22

| Microbial strains | Liquid broth | Solid Medium (agar-based plates) | Temperature of incubation °C | Atmosphere | Time of incubation Initial (hour) | Time of incubation prior UVA exposure (hour) | Intensity of UVA light (µW/cm²) | Time of UVA exposure (minutes) |
|---|---|---|---|---|---|---|---|---|
| *Candida albicans* (Robin) Berkhout ATCC® 10231™ | Sabouraud Dextrose | Sabouraud Dextrose | 24 to 26 | Aerobic | 16 to 24 | 4 to 6 | 1700 | 20, 40 and 60 |
| *Clostridioides difficile* (Prevot) Lawson et al. ATCC® 700057™ | Brain Heart Infusion | Reinforced Clostridial | 36 to 37 | Anaerobic | 24 to 48 | 6 to 8 | 2000 | 20, 40 and 60 |
| *Enterococcus faecalis* ATCC® 29212™ | Brain Heart Infusion | Trypticase Soy Agar with 5% Sheep Blood | 36 to 37 | Aerobic | 18 to 24 | 4 to 6 | 2400 | 20, 40 and 60 |
| *Escherichia coli* GFP ATCC® 25922 GFP™ | Luria Bertani | Luria Bertani | 36 to 37 | Aerobic | 16 to 24 | 2 to 3 | 1300 | 20, 40 and 60 |
| *Escherichia coli* - clinical isolate | Luria Bertani | Luria Bertani | 36 to 37 | Aerobic | 16 to 24 | 2 to 3 | 1100 to 1300 | 20, 40, 60, and 80 |
| *Klebsiella pneumoniae* ATCC® BAA-1705™ | Luria Bertani | Luria Bertani | 36 to 37 | Aerobic | 16 to 24 | 2 to 3 | 1300 | 20, 40 and 60 |
| *Proteus mirabilis* ATCC® 29906™ | Luria Bertani | Hectoen Enteric | 36 to 37 | Aerobic | 16 to 24 | 2 to 3 | 2400 | 20, 40 and 60 |
| *Pseudomonas aeruginosa* ATCC® 15442™ | Luria Bertani | Luria Bertani | 36 to 37 | Aerobic | 16 to 24 | 2 to 3 | 3500 | 20, 40 and 60 |
| *Staphylococcus epidermidis* (Winslow and Winslow) Evans ATCC® 14990™ | Tryptic Soy Broth | Trypticase Soy Agar with 5% Sheep Blood | 36 to 37 | Aerobic | 24 to 48 | 3 to 5 | 2150 | 20, 40 and 60 |
| *Streptococcus pyogenes* Rosenbach ATCC® 19615™ | Tryptic Soy Broth | Trypticase Soy Agar with 5% Sheep Blood | 36 to 37 | Anaerobic | 24 to 48 | 3 to 5 | 1800 | 20, 40 and 60 |

| Microorganism | UVA intensity (μW/cm²) | Group | Baseline CFUx10⁷/mL | 20 min CFU X 10⁷/mL | P value | 40 min CFU X 10⁷/mL | P value | 60 min CFU X 10⁷/mL | P Value |
|---|---|---|---|---|---|---|---|---|---|
| Clostridioides difficile | 2,000 | Exposed | 0.1 | 0.08 | 0.01 | 0.01 | 0.003 | 0.0031 | 0.01 |
| | | Control | 0.1 | 0.13 | | 0.17 | | 0.39 | |
| Candida albicans | 1,700 | Exposed | 0.14 | 0.09 | 0.007 | 0.03 | 0.001 | 0.032 | 0.001 |
| | | Control | 0.14 | 0.17 | | 0.2 | | 0.16 | |
| Pseudomonas aeruginosa | 3,500 | Exposed | 0.81 | 0.07 | <0.001 | No growth | <0.001 | No growth | <0.001 |
| | | Control | 0.81 | 0.61 | | 0.93 | | 0.85 | |
| Klebsiella pneumoniae | 1,300 | Exposed | 5.9 | 6.34 | 0.17 | 3.34 | <0.001 | 1.53 | <0.001 |
| | | Control | 5.9 | 7.49 | | 10.5 | | 13.81 | |
| Escherichia coli | 1,300 | Exposed | 1.25 | 0.41 | <0.001 | 0.21 | 0.001 | 0.03 | <0.001 |
| | | Control | 1.25 | 3.31 | | 4.2 | | 5.52 | |
| Enterococcus faecalis | 2,400 | Exposed | 9.21 | 2.99 | 0.1 | 0.61 | 0.01 | 0.08 | 0.01 |
| | | Control | 9.21 | 10.6 | | 14.72 | | 17.74 | |
| Streptococcus pyogenes | 1,800 | Exposed | 1.17 | 0.68 | 0.64 | 0.64 | 0.001 | 0.17 | 0.004 |
| | | Control | 1.17 | 0.83 | | 1.68 | | 1.31 | |
| Proteus mirabilis | 2,400 | Exposed | 0.62 | No growth | <0.001 | No growth | <0.001 | No growth | <0.001 |
| | | Control | 0.62 | 0.59 | | 0.49 | | 0.54 | |
| Staphylococcus epidermidis | 2,150 | Exposed | 0.57 | 0.43 | 0.01 | 0.03 | <0.001 | 0.000117 | <0.001 |
| | | Control | 0.57 | 0.59 | | 0.69 | | 0.7 | |

FIG. 23

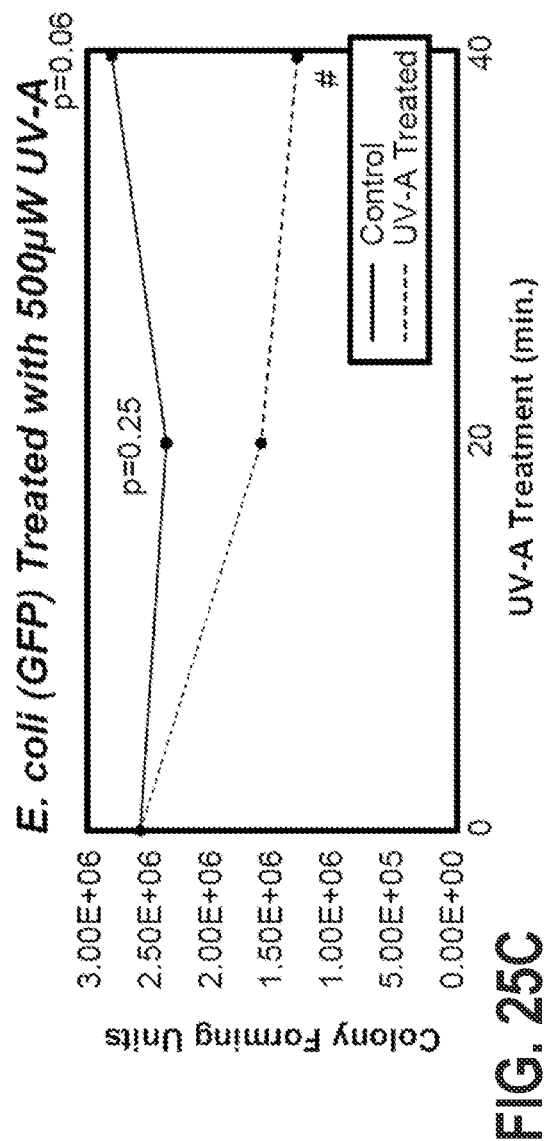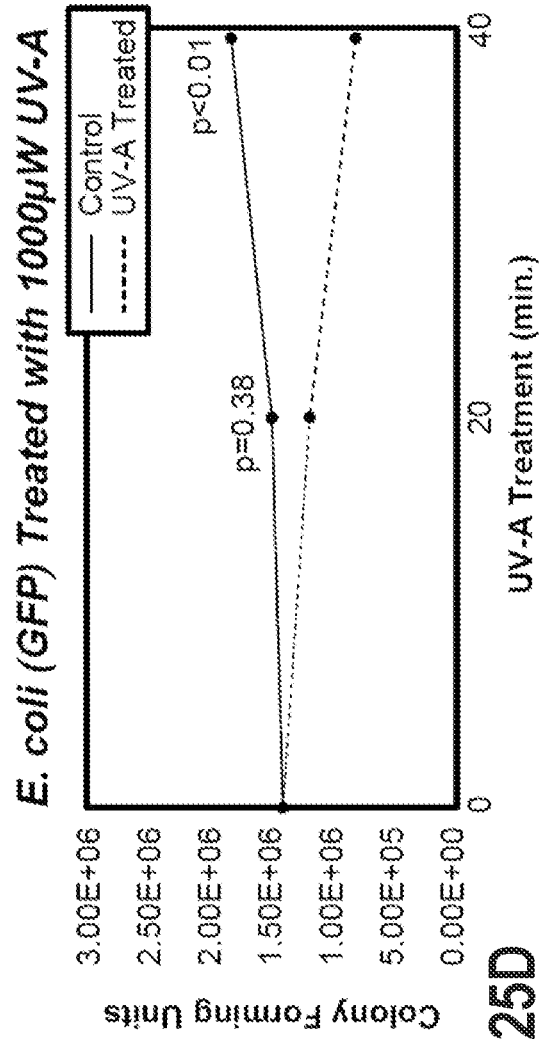

INTERNAL ULTRAVIOLET THERAPY

CROSS-REFERENCE TO RELATED APPLICATIONS

This application is a national phase of International Application No. PCT/US2021/046011, filed Aug. 13, 2021, which designated the U.S. and that International Application was published under PCT Article 21 (2) in English, which claims priority to U.S. Provisional Application No. 63/065,167, filed Aug. 13, 2020 titled INTERNAL ULTRAVIOLET THERAPY, the contents of which are incorporated herein by reference.

FIELD OF THE DISCLOSURE

The present invention is directed to systems and methods for ultraviolet therapy to treat patients, including for use with treatment of inflammatory diseases.

BACKGROUND OF THE DISCLOSURE

The following description includes information that may be useful in understanding the present invention. It is not an admission that any of the information provided herein is prior art or relevant to the presently claimed invention, or that any publication specifically or implicitly referenced is prior art.

Gastrointestinal (GI) disorders include diseases of the esophagus, stomach, small intestine, colon, and rectum. Although GI disorders are some of the most prevalent disorders, their symptoms are not effectively managed and in some cases, effective treatment options are not available. Among the disorders affecting the GI tract, one of most common condition includes Inflammatory Bowel Disease (IBD).

Inflammatory Bowel Disease (IBD) is thought to arise from an aberrant host immune response to intraluminal commensal flora in a genetically-susceptible individual. There are two major forms of IBD, which include ulcerative colitis (UC) and Crohn's disease (CD). Patients suffering from 1IBD may face morbidity and heavy productivity losses. Current trends indicate an increase in the rate of incidence and prevalence of IBD; however, effective long-term treatment options and/or cure have not been identified. As a result, IBD causes substantial financial burden to the healthcare system worldwide.

UC, one of the forms of IBD, involves inflammation of the colon epithelium in a continuous fashion, involving the rectum and varying anatomic involvement of the colon. Among people with UC, about 35% have involvement of the rectum and sigmoid colon, 40% have involvement of the entire left colon, and 25% have extensive inflammation affecting more proximal parts of the colon as well. Symptoms of UC include diarrhea, rectal bleeding, and abdominal pain, and is associated with significant morbidity, cost, and impact on quality of life.

Current approved therapies for UC involve mesalamine for mild disease, and immune suppression or immune modulation via broad or targeted approaches for those with moderate to severe disease with biologics and small molecules. These treatments have potential adverse effects including systemic infection, lymphoma, and immune-mediated reactions. Clinical trials for therapeutics in mild as well as moderate to severe UC show that the majority of patients do not achieve remission even with optimized dosing of biologic therapy in combination with immune-modulators. Currently approved therapies for moderate to severe ulcerative colitis are only effective in a minority of patients, and (depending on the class of drug) are associated with risks of infection, malignancy, thrombosis and immune-mediated reactions.

Thus, there is a significant unmet need for safe and effective treatment of GI tract disorders, such as IBD, for patients with mild as well as moderate-to-severe disease progression.

SUMMARY OF THE DISCLOSURE

Inventors herein have identified that manipulation of the microbial flora using UV-A light emitted at wavelengths in a UV-A range may provide an effective and safe treatment for IBD. Further, the inventors have identified that the UV-A light may be administered intraluminally along any length of the GI tract in a safe and effective manner. Therefore, the UV-A light may be used for effective microbiome-modulation and/or anti-inflammatory light treatment for various infectious and/or inflammatory conditions of the GI tract, including IBD.

As disclosed herein, application of UV-A light has significant antimicrobial effects, against a wide range of bacteria, viruses and other organisms. Further, the UV-A light emitted at wavelengths in a range between 335 nm and 348 nm provides a unique therapeutic window, wherein the wavelengths in the range between 335 nm and 348 nm targets extracellular microbes providing extracellular antimicrobial treatment (against microbes that attach to the cell surface). Further, the UV-A light emitted in the 335-349 nm range penetrates intracellularly, into the cytoplasm of the cells to cause an effective intracellular anti-microbial response (against microbes that invade the cells or are internalized into the cytoplasm) without causing UV-induced DNA damage. Therefore, UV-A light emitted at wavelengths between 335 nm and 348 nm can be safely and effectively used to treat, ameliorate, and/or prevent diseases affecting the GI tract by modulating intestinal microbiome (that is, providing extracellular and intracellular antimicrobial effect) and/or reducing inflammation within the lumen of the GI tract.

Accordingly, in one example, a light delivery device for performing intra-luminal light therapy comprises: a delivery tube comprising a light emitting portion, the light emitting portion including a plurality of light sources configured to emit narrow-band light at wavelengths in an ultraviolet A (UV-A) range between 335 nm and 349 nm; a plurality of distendable balloons connected to the delivery tube at the light emitting portion, each of the plurality of distendable balloons in fluid communication with a respective inflation port; wherein each of the plurality of distendable balloons is composed of a UV transparent material.

In this way, by using the plurality of balloons, the delivery device may be stabilized in place during UV light administration, which provides consistent UV exposure to treatment areas within the lumen. Further, the balloons may increase uniformity of light distribution to the treatment site. As a result, the balloons increase irradiance distribution at the treatment site.

Further, when utilized for treatment within a GI tract, the balloons in their inflated state may stretch out one or more folds and haustra of a colon, thereby increasing surface area of the colon during treatment. As a result, the balloons increase an amount of light exposure uniformly across the surface of the colon which improves efficiency and effectiveness of UV-light treatment. Further, the balloon inflation also pushes away obstructing stool/debris between the light source and the colon epithelium. Furthermore, the balloons may help diffuse extraneous debris/biofilm that may act as a barrier between the delivery device and the colonic epithelium. Further still, the balloons also prevent stool from descending into the treatment segment. That is, the balloons do not allow proximal debris and feces to move antegrade and block the emission of UV to colon mucosa. At least through these above-mentioned effects, the balloons improve irradiance as well as irradiance distribution to the colon epithelium, thereby increasing efficiency and effectiveness of UV-light treatment.

Further still, the multi-balloon approach may allow for flexibility of the device when traversing the hepatic and splenic flexures, as well as a customized way of delivering light to just those segments exhibiting inflammation, and reducing exposure to non-inflamed segments, for example, through selective illumination of the ballooned segments correlating with the individual's extent of disease.

Accordingly, a multi-balloon internal UV-A phototherapy could provide a safe and effective alternative to anti-inflammatory and immunosuppressive therapies for IBD and other gastrointestinal tract disorders as disclosed herein. Therefore, the antimicrobial and/or anti-inflammatory properties of UV-A light are utilized to manipulate the intestinal microbiome and/or reduce inflammation in patients with IBD, while the plurality of balloons are used to improve UV light distribution, irradiance, reduce disruption caused by stool and biofilm formation, and stabilize the GI track as well as stabilize the delivery device during the UV-A light treatment.

As will be described in the Detailed Description section below, in vitro and in vivo safety data show that UV-A can be safely applied even at close distance to various human cell types, with no evidence of DNA damage, cell growth inhibition, or histologic inflammation.

Additional features and advantages of the disclosure will be set forth in the description that follows, and in part, will be obvious from the description; or can be learned by practice of the principles disclosed herein. The features and advantages of the disclosure can be realized and obtained by means of the instruments and combinations particularly pointed out in the appended claims. These and other features of the disclosure will become fully apparent from the following description and appended claims, or can be learned by the practice of the principles set forth herein.

BRIEF DESCRIPTION OF THE DRAWINGS

In order to describe the manner in which the above-recited disclosure and its advantages and features can be obtained, a more particular description of the principles described above will be rendered by reference to specific examples illustrated in the appended drawings. These drawings depict only example aspects of the disclosure, and are therefore not to be considered as limiting of its scope. These principles are described and explained with additional specificity and detail through the use of the following drawings:

FIGS. 3A and 3B shows schematic illustrations of a light catheter assembly with a plurality of balloons in a deflated condition and in an inflated condition respectively, according to an embodiment of the present disclosure;

FIG. 7 shows a schematic of an enlarged portion of the UV light catheter of FIG. 2A;

FIG. 8 shows a schematic of an example UV light catheter comprising one or more Chip on Board (COB) mini bars included within a delivery tube, in accordance with an embodiment of the present disclosure;

FIG. 9A shows a schematic of a fiber optic system coupled to a UV LED light source, in accordance with an embodiment of the present disclosure;

FIGS. 9B and 9C shows schematic illustrations of multiple UV LED light sources for implantation with the fiber optic system, in accordance with an embodiment of the present disclosure;

FIG. 10A shows a flat configuration and a tubular configuration of a flexible printed circuit board (PCB) utilized in conjunction with one or more UV LED light sources, in accordance with an embodiment of the present disclosure;

FIG. 10B shows a schematic illustration of an example heat sink implemented in a UV light catheter, in accordance with an embodiment of the present disclosure;

FIG. 11A shows a schematic illustration of an example configuration of a plurality of LEDs and a plurality of linear reflectors, in accordance with an embodiment of the present disclosure;

FIG. 11B shows a schematic illustration of an example heat sink implemented in a UV light catheter, in accordance with an embodiment of the present disclosure;

FIG. 11C shows a schematic illustration of an example light distribution in an example UV LED light source including a plurality of LEDs and a plurality of linear reflectors, in accordance with an embodiment of the present disclosure;

FIGS. 17A and 17B show growth curves of liquid culture containing E. coli when implementing an exemplary narrow band UV-A emitting device;

FIG. 22 shows a table showing the intensities and exposure durations of narrow band UV-A light applied to bacterial cultures in one example;

FIG. 23 shows a table showing bacterial counts over time during narrow band UV-A light exposure in one example;

FIGS. 25C-25F show growth curves showing E. coli bacterial counts over time exposed to various intensities of UV light using an exemplary system;

Figure 1A:
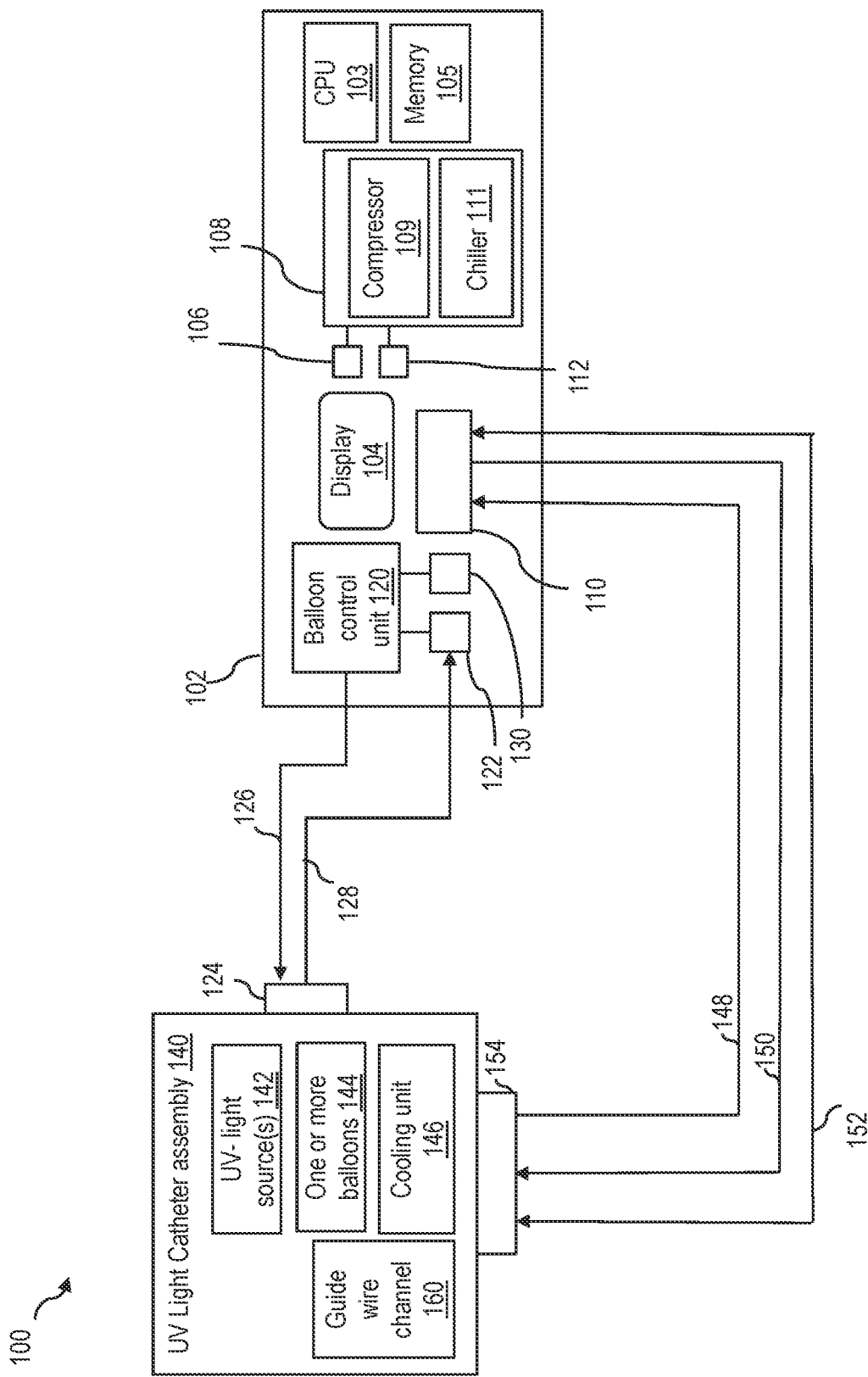
FIG. 1A shows a schematic block diagram depicting an overview of a light treatment system, in accordance with an embodiment of the present disclosure.

As used herein, the term "LED" refers to a light emitting diode that is a semiconductor light source that emits light across various visible and non-visible light spectrums. LEDs typically have an emission spectrum that includes a set of wavelengths that vary in intensity over their emission spectrum range, and typically follow a bell or similar shaped intensity curve over that wavelength range. Specific LEDs are typically described using their wavelength of peak emission intensity, or the wavelength at which the LED emits its highest intensity of radiation.

Accordingly, LEDs typically emit light across a range of wavelengths, and specific LEDs may also be described using the range of wavelengths it emits over a threshold intensity (in some examples, a percentage of the LEDs maximum intensity). For instance, a given LED may emit light with at least 10% of its maximum emission intensity only between the wavelengths of 335 nm and 345 nm. Below 335 nm and above 345 nm, that LED's intensity of emission may be less than 10% of that LED's peak intensity emission wavelength ("peak wavelength" herein), and in some cases too low to be therapeutically relevant. Therefore, for many treatment applications, only the wavelengths between 335 nm and 345 nm would have an impact on treatment for that specific LED.

Accordingly, the range of wavelengths described herein may be the range of wavelengths that is therapeutically effective or significant for a particular treatment application, duration, and intensity of emission delivered by the LED to the treatment site (or based on power of emission emitted by the LED). In some examples, the range of wavelengths may be the range of wavelengths emitted by the LEDs that have an intensity that is at least 1, 2, 3, 4, 5, 6, 7, 8, 9, 10, 11, 12, 13, 14, 15, 16, 17, 18, 19, or 20% of the peak emission intensity.

Accordingly, disclosed herein are emission spectrum ranges for various LED light sources which correspond to the ranges for which the LED emits a threshold intensity percentage of its maximum intensity. Examples of various LED spectrum emission ranges and peak intensity wavelengths of emission of commercially available LEDs are described in Filippo, et al, "LEDs: Sources and Intrinsically Bandwidth-Limited Detectors," the content of which is incorporated by reference in its entirety.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Overview

Figure 1B:
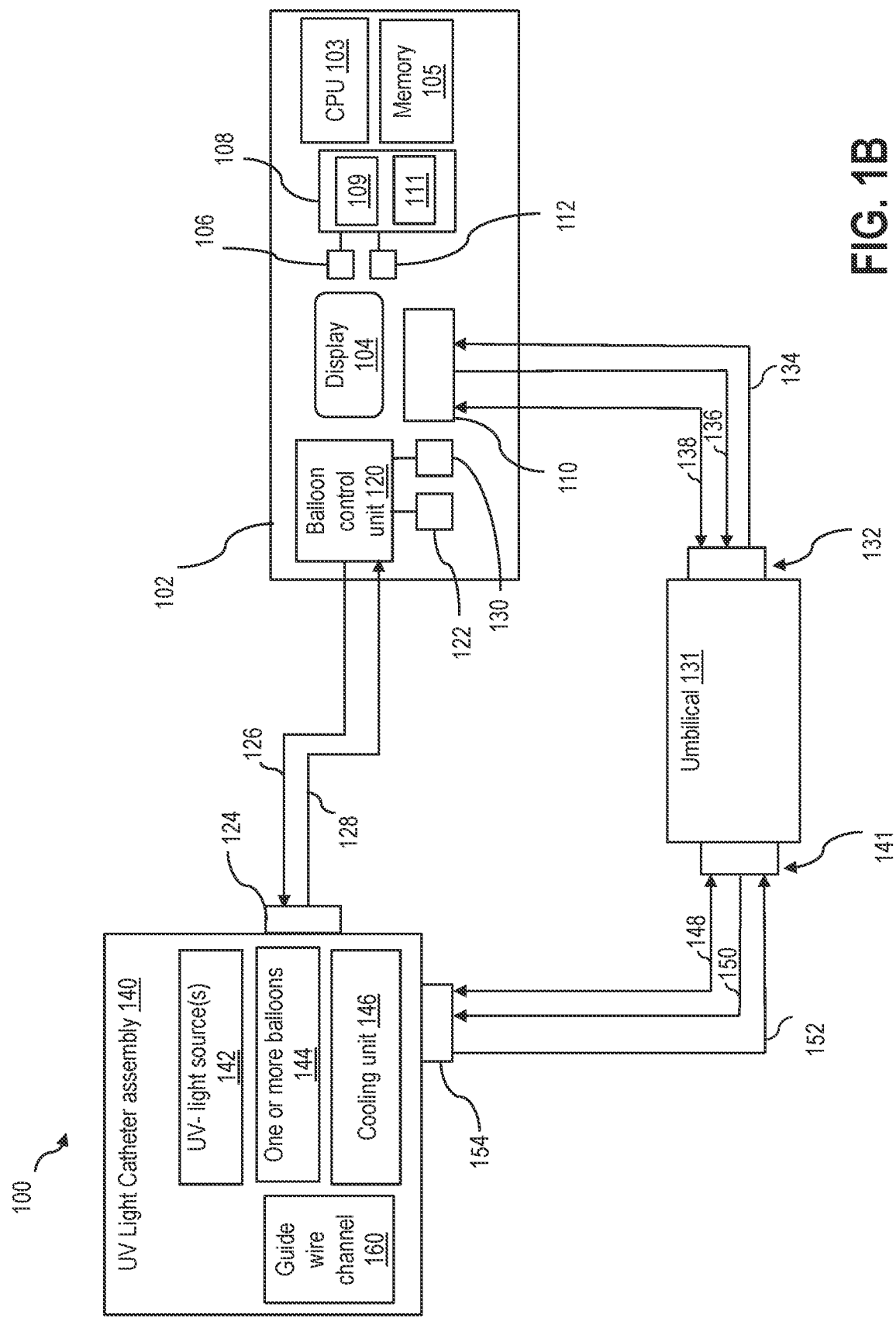
FIG. 1B shows a schematic block diagram of the light treatment system of FIG. 1A, in accordance with another embodiment of the present disclosure.
Figure 2A:
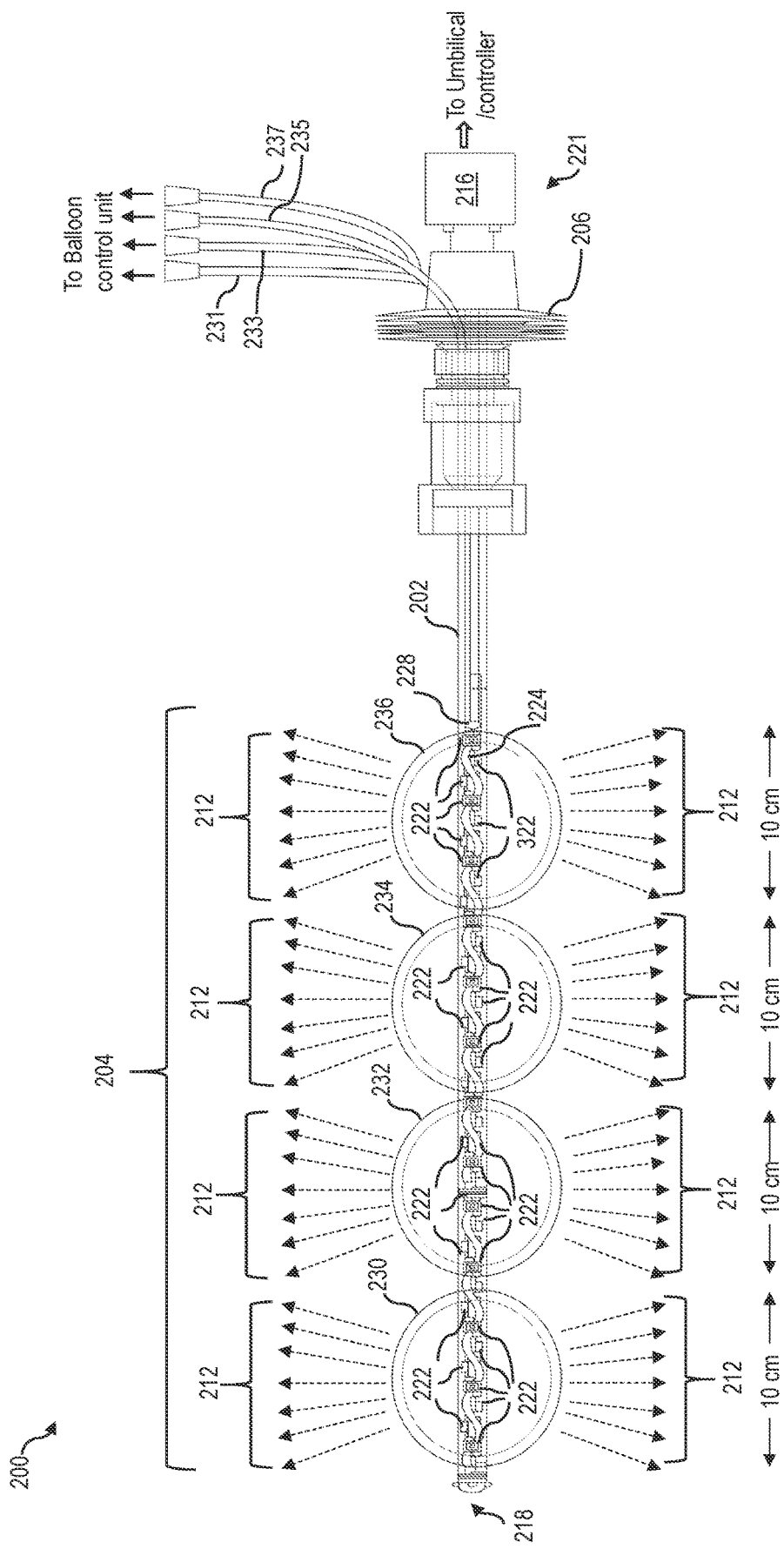
FIG. 2A shows a schematic illustration of a light catheter assembly comprising a plurality of balloons, according to an embodiment of the present disclosure.
Figure 2B:
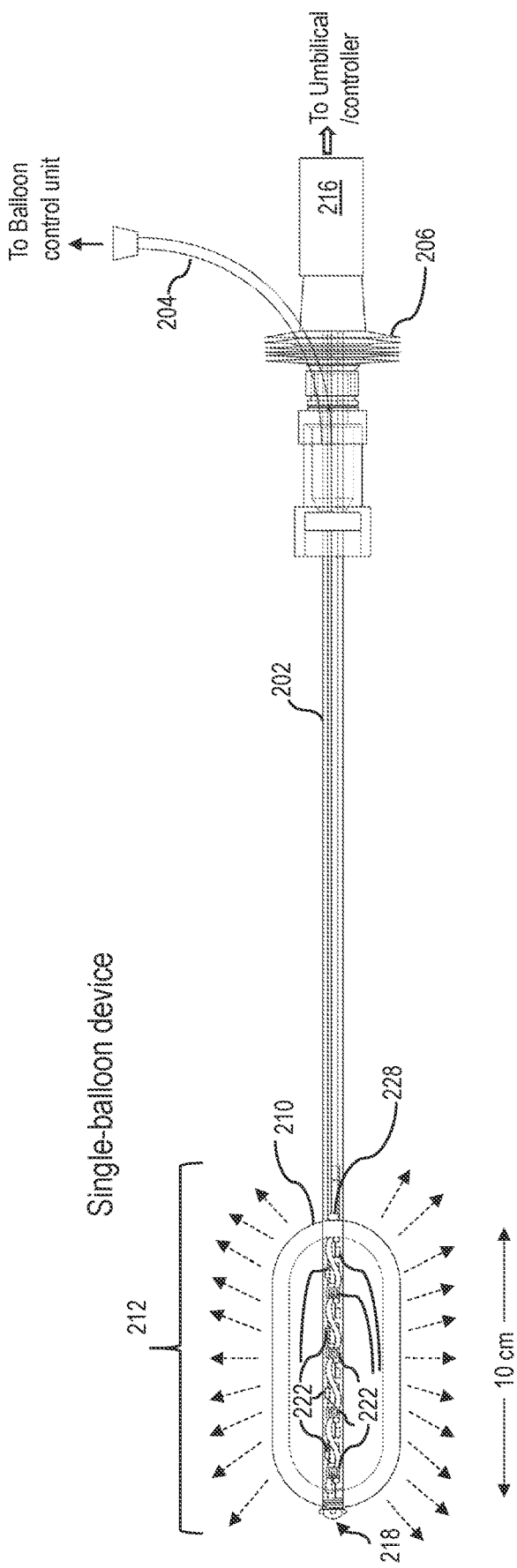
FIG. 2B shows a schematic illustration of a light catheter assembly comprising a light emitting portion within a single balloon, according to an embodiment of the present disclosure.
Figure 4A:
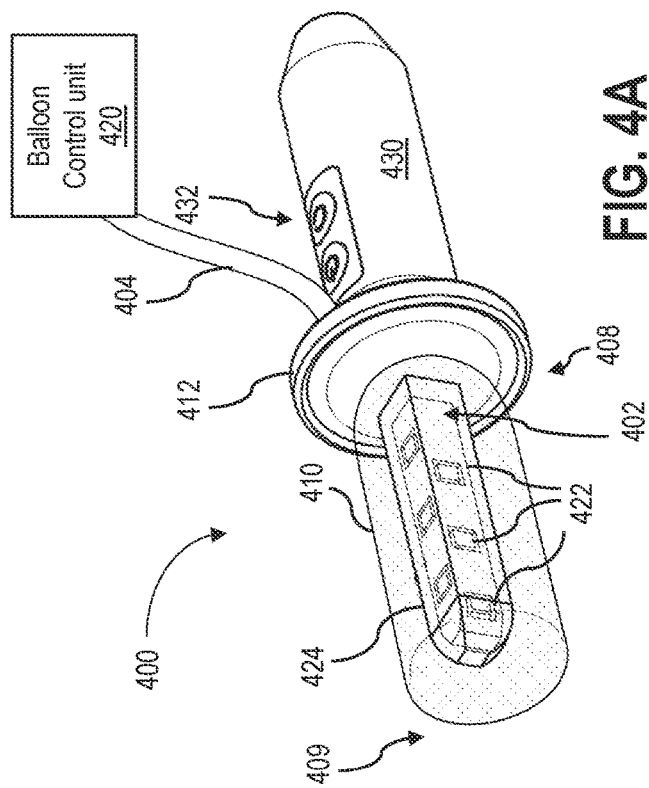
FIG. 4A shows a schematic illustration of an exemplary UV emitting device with a single balloon element, in accordance with an embodiment of the present disclosure.
Figure 4B:
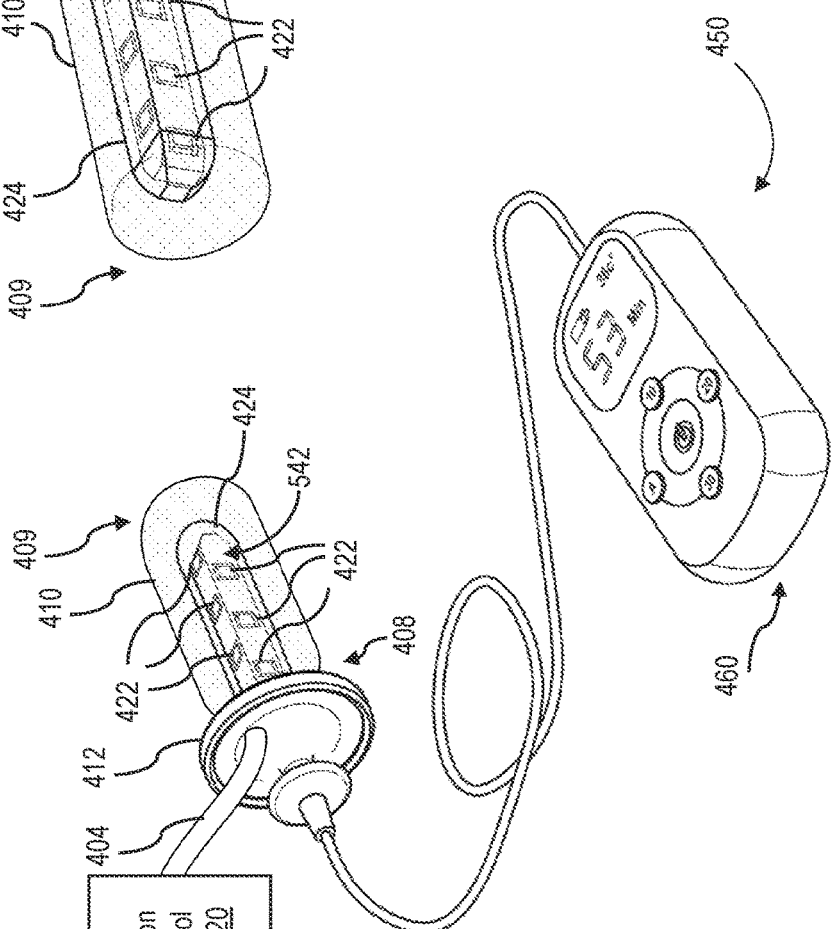
FIG. 4B shows a schematic illustration of an exemplary UV emitting device with a single balloon, in accordance with another embodiment of the present disclosure.
Figure 5A:
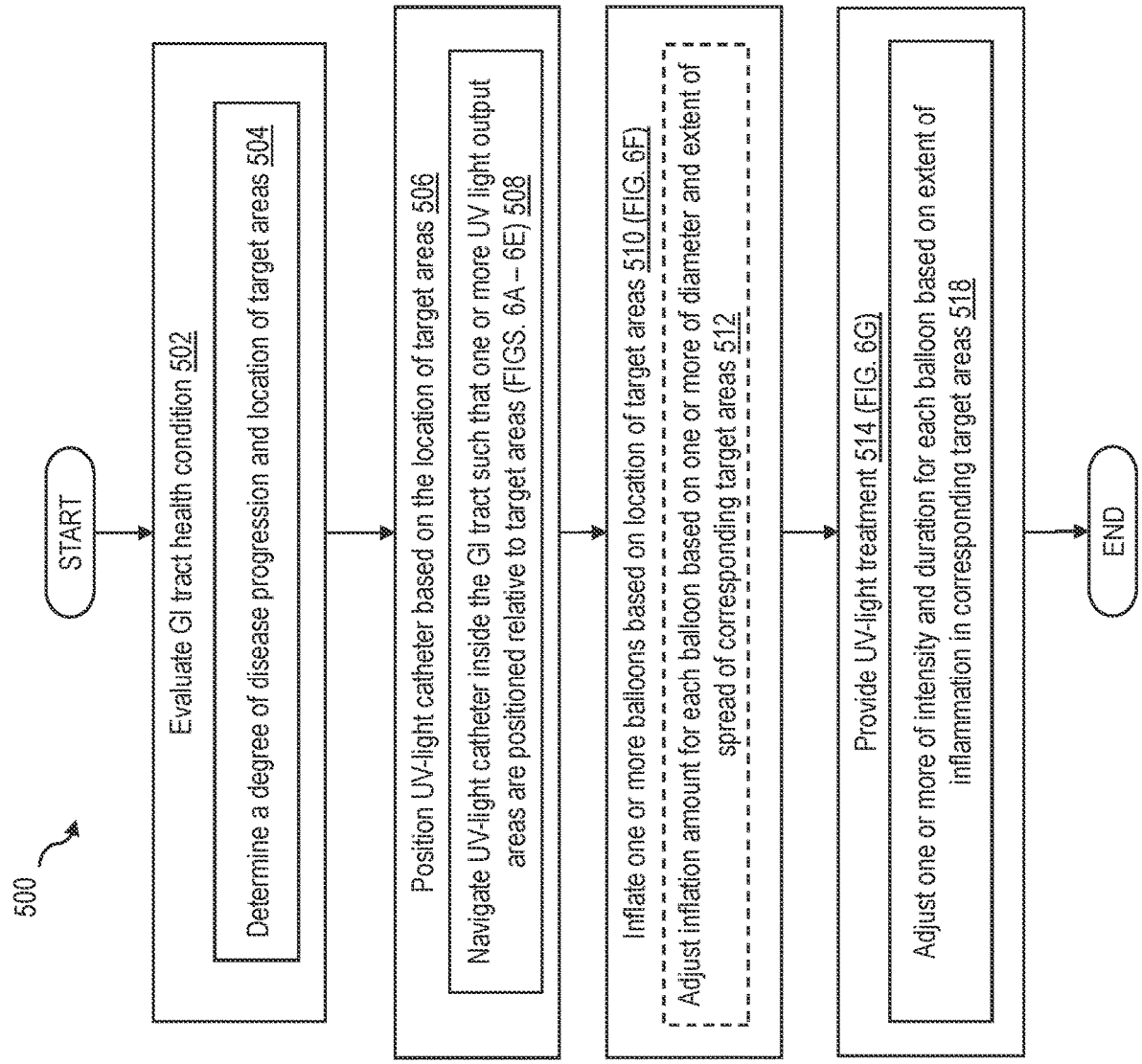
FIG. 5A shows a flow chart illustrating an example method for treating, ameliorating, and/or preventing a GI tract disease using a delivery device comprising a plurality of balloons, in accordance with an embodiment of the present disclosure.
Figure 5B:
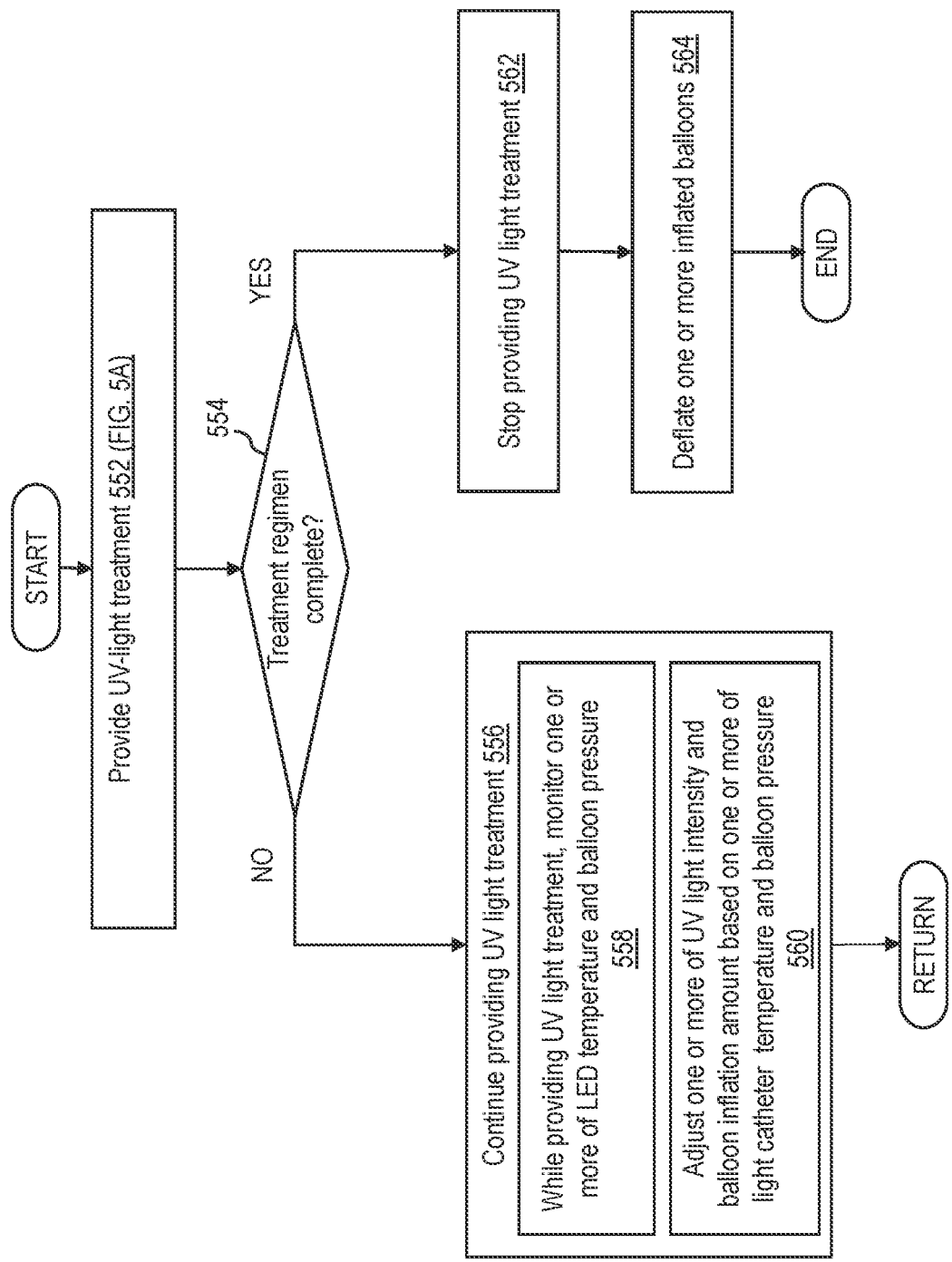
FIG. 5B shows a flow chart illustrating an example method for adjusting operation of one or more of balloon and UV LEDs while administering UV light using a delivery device comprising a plurality of balloons; in accordance with an embodiment of the present disclosure.

Methods and systems are provided for treating, ameliorating, and/or preventing inflammatory and/or infectious diseases affecting the gastrointestinal tract. In particular, methods and systems are provided for improving effectiveness and safety in treating, ameliorating, and/or preventing inflammatory and/or infectious diseases affecting the gastrointestinal tract using narrow-band light emitted at wavelengths in the an ultraviolet A (UV-A) range. In some examples, methods and systems described herein may be applied for treating vaginal infections and/or inflammations. Example UV light treatment systems including a UV light catheter assembly comprising a plurality of UV light sources and a plurality of distendable balloons are shown at FIG. 1A and FIG. 1B. Examples of the UV light catheter assembly comprising a delivery tube having a light emitting portion including a plurality of light emitting diodes (LEDs) and a plurality of distendable balloons are shown at FIGS. 2A, 3A, and 3B. Further, a single balloon device comprising a single balloon coupled to a light emitting portion is shown at FIG. 2B. Further examples of the single balloon device are shown at FIGS. 4A and 4B. FIG. 5A describes an example method for treating, ameliorating and/or preventing infectious and/or inflammatory conditions of the GI tract using a delivery device comprising a plurality of balloons. Further, FIG. 5B shows an example method for controlling balloon operation and delivery device operation during UV light treatment. FIGS. 6A-6G illustrate example positioning and deployment of a multi-balloon UV light delivery device within a lumen of a large intestine. FIGS. 7-11C show example UV light sources that may be included in the delivery device for providing UV light treatment. FIGS. 12A-33 shows experimental data showing antimicrobial effectiveness and safety of UV-A light against various microbes.

A technical advantage of using one or more balloons coupled to the UV light delivery device includes improvement in effectiveness of UV light treatment by improving UV light distribution, uniformity of light distribution, and irradiance at the treatment site through the one or more of increasing surface area of the treatment sire by stretching out folds and haustra at the areas of contact between the balloons and colonic epithelium at the treatment site, uniformity of distance to the UV light source, displacing obstructing stool and/or debris (e.g., biofilms) at the treatment site, and preventing proximal stool and/or debris from descending to the treatment site. Another technical advantage of using the delivery device including the one or more balloons includes selective treatment based on a number of treatment areas and/or location of the treatment areas. Using one or more balloons, the UV light therapy may be customized through selective operation and/or adjustment of the balloons depending on one or more of location, severity, and extent and pattern of spread of infection and/or inflammation. Further, the one or more balloons when inflated to be in contact with the colonic epithelium, may stabilize the walls of the colon as well as stabilize the delivery device within the lumen and therefore, reduce injuries caused during the deployment of the delivery device and during treatment. Further, the one or more balloons maintain a constant distance between the treatment site and the UV light source during light treatment, thereby providing uniform light delivery over the duration of the treatment. Further, the delivery device including one or more balloons may be efficiently navigated through the lumen of the GI tract (e.g., through hepatic and/or splenic flexures), thereby allowing UV light to be delivered to any location within the GI tract.

UV Light Treatment System

FIG. 1A shows an overview of an example UV light treatment system 100. The UV light treatment system 100 may be configured for delivering UV light to one or more portions of gastrointestinal (GI) tract for treating, ameliorating, reducing, and/or preventing infection and/or inflammation conditions. For example, the UV light treatment system may be configured to administer UV light intraluminally to the one or more portions of the GI tract. The one or more portions of the GI tract may include, but not limited to one or more areas of the large intestine (e.g., rectum, sigmoid colon, descending colon, transverse colon, ascending colon), one or more areas of small intestine (e.g., duodenum, jejunum, ileum), one or more areas of the stomach, and/or one or more areas within the esophagus. In some embodiments, as discussed at FIGS. 4A and 4B, the UV light treatment system 100 may be configured to treat vaginal infections and/or inflammation. Further, the UV light treatment system 100 may be configured to administer UV light evenly over target areas of the GI tract (that is, even distribution of UV light on the target areas) and improve irradiance and irradiance distribution at the target area. The target areas are alternately referred to herein as treatment areas, and include areas within the GI tract that are affected by a GI tract disease condition. In some examples, when UV light treatment may be applied for preventative purposes, and thus the target areas may include areas that are more susceptible to infection and/or inflammation (e.g., areas that are immediately adjacent to the infected and/or inflamed areas) or areas that are suspected as having infection and/or inflammation. In some other examples, the UV light treatment may be applied to areas that have been treated and cured, in order to prevent re-occurrence of infection and/or inflammation. The target areas may include an intraluminal area within the GI tract, one or more adjacent intraluminal areas within the GI tract, or one or more non-adjacent intraluminal areas within the GI tract.

Furthermore, the UV light treatment system 100 may be configured to administer UV therapy selectively within the one or more portions of the GI tract. As a non-limiting example, the UV light treatment system 100 may be configured to deliver UV light to a portion of sigmoid colon or all of sigmoid colon. In another non-limiting example, the UV light treatment system 100 may deliver UV light to a portion of descending colon and a portion of sigmoid colon. In yet another example, the UV light treatment system 100 may selectively deliver UV light simultaneously to non-adjacent areas of the large intestine (e.g., a portion of sigmoid colon and a portion of transverse colon). Thus, the UV light treatment system 100 may be configured so as to customize UV treatment based on the target areas (that is, infected and/or inflamed areas), which may be a single area, one or more adjacent areas, one or more non-adjacent areas, or a combination thereof. Further, in some examples, when multiple target areas are treated, the UV therapy may be administered simultaneously in order to improve efficiency and speed of UV light treatment.

The UV light treatment system 100 includes a UV light catheter assembly 140 comprising one or more UV light sources 142, one or more balloons 144, and a cooling unit 146 configured to maintain the UV light catheter assembly within a desired temperature range and reduce over-heating. In one example, the one or more UV light sources 142 and the cooling unit 146 may be positioned within a delivery tube (e.g., a cylindrical flexible tube) while the one or more balloons may be disposed on the delivery tube along a length of the delivery tube. The delivery tube is also referred to herein as a catheter or a light catheter. In another example, the one or more light sources 142 and the one or more balloons 144 may be positioned on the delivery tube while the cooling unit is located within the housing catheter. In yet another example, the cooling unit 146 may be positioned in a handle portion that is attached to the delivery catheter including the one or more light sources 142 positioned within, on, or embedded in the housing catheter. In this example, the one or more balloons 144 may be positioned on the delivery tube.

In one embodiment, a single balloon may be positioned at a distal portion of the housing catheter (e.g., the distal portion opposite to a proximal portion that connects to a control unit 102 discussed below). A non-limiting example of a UV light catheter assembly including a single expandable balloon is shown at FIG. 2B. In some examples, UV-light catheter assembly for vaginal or rectal UV administration, such as example devices shown at FIGS. 4A and 4B may have a single balloon that may be deployed upon positioning in vivo.

In another example, the one or more balloons 144 may be positioned along a length of the delivery tube to treat infections at various locations throughout the length of the infected area (e.g., throughout the length of the colon). The one or more balloons 144 are configured as UV-transparent balloons to allow transmission of UV light from the UV light sources 142 to the respective target sites. The balloons may be constructed using materials that provide 100% UV transparency (that is, 100% UV transmittance through the material) or any material or combination of materials that provide UV transparency in a range between 100% and 80% (that is, UV transmittance in a range between 100% and 80%). In one example, the UV-transparent balloons may be made out of polyether block amide (PEBA). PEBA is partially UV transparent (that is, ~15% loss of intensity). In another example, the UV-transparent balloons may be constructed out of Cyclic olefin copolymer (COC), which is 100% UV transparent. In yet another example, the UV-transparent balloons may be composed of silicone. Further, the UV-transparent materials used for constructing the one or more balloons 144 may be medical grade materials. Furthermore, the UV-transparent materials (that is, UV transmitting materials) may also be UV-stable.

The one or more balloons 144 may be utilized to secure the device in place during light administration, and thereby, reduce unwanted movement of the housing catheter. Further, the one or more balloons 144 may be utilized to stretch out folds in the GI tract, and provide more uniform light exposure to targeted areas. Furthermore, the one or more balloons 144 may be utilized to diffuse extraneous debris/biofilm that may act as a barrier between the light catheter assembly 140 and the epithelium. Further still, the one or more balloons 144 may prevent stool from descending into the treatment segment, thereby improving effectiveness, efficiency, evenness, and consistency of the UV light treatment provided via the UV light treatment device.

In one example, the one or more balloons 144 may be inflatable through one or more corresponding ports coupled to a fluid source (e.g., air pump), and thus, may be inflated upon navigating the UV light catheter assembly to a desired position in vivo prior to powering up the UV-light sources. Further, the one or more balloons 144 may be configured such that the positions of the one or more balloons may be adjusted. For example, the one or more balloons may have a modular configuration and thus, a number of balloons and positioning of the number of balloons may be customized based on one or more of the disease condition (e.g., ulcerative colitis, Crohn's disease), location of the disease condition (e.g., based on which areas of the colon are affected), and degree of progression of the disease condition in the affected areas. Further, as will be discussed below at FIG. 2A, in some embodiments, an extent of inflation of each of the one or more balloons may be adjusted based on the disease condition, location of the disease condition, diameter of the target area, and/or degree of inflammation and/or infection of the areas affected due to the identified diseased condition. For example, a first target area may have a smaller diameter than a second target area. That is, the first target area may be narrower (e.g., due to colonic strictures) than the second target area. Accordingly, a first inflation amount of a first balloon used for delivering light to the first area may be lesser than a second inflation amount of a second balloon used for delivering light to the second target area with greater diameter.

The one or more UV light sources 142 may be configured to deliver narrow bandwidth UV light having wavelengths in the UV-A region. The light having wavelengths in the UV-A region have effective antimicrobial properties and are safe for internal administration within the patient's body over a large area (e.g., entire sigmoid colon or any large area within the patient's body). Further, the inventors have identified that certain wavelengths in the UV-A region penetrate intracellularly to activate antimicrobial response without cause UV-induced DNA damage. In one example, the wavelengths in the UV-A region may be in a range between 335 nm and 349 nm. Further, the wavelengths in the UV-A region may have a peak wavelength between 335 and 349 nm, or between 339 nm and 346 nm or between 338 and 342 nm, or between 338 nm and 346 nm.

In another example, the one or more light sources 142 may emit light with wavelengths in the UV-A region between 338 nm and 342 nm or between 339 nm and 346 nm. Accordingly, the wavelengths may have a peak wavelength between 338 nm and 342 nm or between 339 nm and 346 nm. In some examples, the one or more light sources 142 may emit light with one or more peak wavelengths between 335 nm and 349 nm or between 338 nm and 342 nm or between 339 nm and 346 nm or between 338 nm and 346 nm.

In one example, the one or more light source may be a plurality of light emitting diodes (LEDs), wherein each LED is configured to emit a narrow bandwidth light having wavelengths in the UV-A region. As mentioned above, the narrow bandwidth light may have wavelengths between 335 nm and 349 nm, between 338 nm and 346 nm, or between 338 nm and 342 nm, or between 339 nm and 346 nm.

In various embodiments, other types of light sources other than LED may be used. Example light sources are described with respect to FIGS. 8-12.

The UV light catheter assembly 140 may be coupled to a control unit 102. In one example, the control unit 102 includes a cooling system 108 for providing coolant flow through the cooling unit 146 within the UV light catheter assembly 140 for regulating a temperature of the UV light assembly. The cooling system 108 includes a compressor 109 (e.g., a medical grade compressor), an air chiller 111 (e.g., medical grade air chiller), a flow sensor (not shown) for return air form the cooling unit 146, a valve 106, and a pressure regulator 112 for initiating and/or stopping coolant flow, and/or for adjusting a coolant flow rate through the cooling tube.

The control unit 102 includes a connector 110 that provides a connection interface (between the control unit 102 and the UV light assembly via one or more connectors or umbilical, discussed below) for coupling with one or more of a warm coolant connector 148, a cold coolant connector 150, and an electrical connector 152. The warm coolant connector 148 may be a tubing for flowing warm coolant from the UV light catheter assembly to the control unit 102, the cold coolant connector 150 may be a second tubing through which cold coolant from the cooling system may flow to the UV light catheter assembly, and the electrical connector 152 may provide electrical coupling between the UV light catheter assembly and the control unit 102. In one example, the connector 152 may be a wired connection or a wireless connection or a combination thereof. In one example, the connector 152 may be used to send electrical signals from the control unit 102 for powering on or powering off the one or more light sources 142. In some examples, an intensity of the one or more light sources 142 and/or a duration of one or more light sources 142 may be controlled via the connector 152.

In some examples, the UV light catheter assembly 140 may include one or more light segments, each light segment comprising a plurality of light sources. In some examples, operation of each light segment (power ON time, power OFF time, adjusting intensity, duration of operation, etc.) may be adjusted independently via the control unit 102. Accordingly, the control unit 102 may include one or more light segment control units (not shown) for adjusting the various operations of corresponding light segments. In some examples, operation of all the light segments may be adjusted in a synchronized manner (e.g., power ON time, power OFF time, duration of operation, intensity, etc.). In some example, some operations (e.g., power ON time) may be synchronized while some other operations (e.g., intensity, power OFF time, duration, etc.) may be independently adjusted. As a non-limiting example, a first intensity of a first light segment delivering light to a first target area may be different from a second intensity of a second light segment delivering light to a second target area, where the first target area has a different degree of infection and/or inflammation compared to the second target area.

The control unit 102 further includes a balloon control unit 120 for adjusting inflation and deflation of the one or more balloons 144. The balloon control unit 120 may be communicatively coupled to one or more pressure sensor(s) 122, which are in fluid communication with the one or more balloons 146. In one example, each of the one or more balloons may be coupled to a corresponding pressure sensor, and pressure inside each balloon may be individually monitored, via a controller of the balloon control unit 120 and/or a controller 103 of the control unit 102. Further, pressure fluctuations within each balloon may be monitored via the controller in order to evaluate one or more of a leak condition and a temperature of the UV-light assembly.

In some examples, the balloon control unit 120 further includes a reservoir 130 for storing an inflation fluid (e.g., air) that may be used to pressurize the one or more balloons 142 to a desired pressure and a desired balloon volume during deployment of the UV light therapy device 100. In one example, the one or more balloons 146 may be selectively pressurized using fluid from the reservoir via the balloon control unit 120. Accordingly, in one example, each of the one or more balloons may be fluidly coupled to one or more balloon inflation ports 124. Each balloon inflation port may be coupled to the reservoir 130 via the balloon control unit 120. Thus, during pressurization of a selected balloon, fluid may flow from the reservoir 130 to the respective balloon inflation port, pass through a channel or passage in the UV light catheter assembly (between the balloon inflation port and the balloon) and subsequently enter the selected balloon.

Further, the balloon control unit 120 may be used to selectively depressurize the one or more balloons. For example, while the UV light treatment assembly is positioned within the patient's colon, upon completion of a treatment duration, the inflated balloons may be deflated prior to removing the UV light treatment assembly from the patient. In some examples, the balloon inflation port and passage may also be used to remove the fluid from the balloon during depressurization. In some other examples, a separate balloon deflation port and passage may be provided to deflate the balloon. Similar to pressurization, the one or more balloons may be selectively depressurized or all the inflated (that is, pressurized) balloons may be simultaneously deflated (that is, depressurized). Further, the balloon control unit may include one or more valves (not shown) for switching between pressurization and depressurization of each balloon. In some embodiments, the balloon control unit 120 may include one or more pumps (not shown) for pressurizing and/or depressurizing the one or more balloons 144. In some examples, the one or more pumps may be coupled to the atmosphere and thus, may use atmospheric air for pressurizing the balloons. Similarly, during depressurization, the air from the balloons may be released into the atmosphere. In some other embodiments, one or more filters may be provided (e.g., at an air intake of a pump) for filtering the air provided for pressurizing the balloons.

Further, one or more pressure sensors 130 may be coupled to the one or more balloon inflation ports to monitor and/or maintain a desired pressure within each of the one or more balloons 144. For example, during inflation, a selected balloon may be inflated via its respective balloon inflation port and a pressure inside the selected balloon may be monitored via a respective pressure sensor fluidly coupled to the respective balloon inflation port. The pressure sensor may transmit pressure signals to the balloon control unit 120. The control unit 120 may monitor pressure signals within each balloon based on signals from respective pressure sensors during operation of the UV light treatment system 100, and automatically adjust pressurization and/or depressurization of the one or more balloons based on a desired pressure. In one non-limiting example, the user may specify the respective desired pressure for each balloon via the control unit 120. Accordingly, one or more of inflation amount, inflation rate, and deflation rate may be individually adjusted. In some examples, one or more of inflation rate, inflation amount, and deflation rate may be adjusted in a synchronized manner for all the balloons under operation (that is, for a number of balloons operated which may be less than or equal to a total number of balloons on the delivery device). Example fluid flow for pressurizing one or more balloons is indicated by 126 and example pressure signals via one or more pressure sensors 122 is indicated by 128. While shown separately, it will be appreciated that each pressure sensor may be coupled to the respective balloon inflation port for monitoring pressure within the respective balloon.

In one example, a therapeutic distance between a target area and the light source may be adjusted based on an amount of pressurization of a balloon deployed in the target area. Said another way, in some examples, an amount of inflation of a given balloon may be adjusted based on a diameter of the lumen, which may be based on native GI tract anatomical features (e.g., small intestine versus large intestine), type of disease, and/or severity of disease affecting the target area. For example, when a target area has a larger diameter, the balloon may be pressurized to a first higher pressure to make contact with the target area and ensure consistent contact throughout the outer side curved surface of the balloon with the target area, which in turn increases one or more of irradiation of UV light administered (e.g., by displacing stools, debris, biofilms, preventing proximal stool descent to the target area, spreading out folds and increasing surface area) while improving irradiation distribution of UV light over the target area. Further, if the target area has a higher degree of inflammation and/or infection which causes narrowing of the lumen, the balloon may be pressurized accordingly (e.g., inflated to a lower volume) so as to make necessary contact with the epithelium and improve irradiance and/or irradiance distribution as discussed above. Further, in some examples, additionally, the light source parameters may be changed (e.g., adjusting current to increase or decrease intensity) based on the diseased condition for selective light treatment.

While FIGS. 1A and 1B show the balloon control unit 120 and the reservoir 130 integrated with the control unit 102, it will be appreciated that the balloon control unit 120 and/or the reservoir 130 may be separate from the control unit 102. Similarly, the cooling system 108 may be integrated (as shown) or separate from the control unit 102.

The inflation fluid may be a UV-transparent fluid that allows the UV light from the one or more light sources 142 to pass through effectively. Further, the one or more balloons 144 may be constructed using a UV-transparent material that allows transmission of UV-A light emitted at wavelengths in a range from 335 nm to 350 nm from the one or more light sources 142 through the balloons 144 and reach the target tissue. Example UV-transparent materials that may be used include, but not limited to, polyether block amide (PEBA), Cyclic olefin copolymer (COC), and silicone.

In some embodiments, as shown in FIG. 1B an umbilical assembly 131 may be utilized to couple the control unit 102 with the UV light catheter assembly 140. For example, the connector 110 may be used to couple one or more of a warm coolant connector 134, a cold coolant connector 136, and an electrical connector 138 of the umbilical tube assembly 131 (at a controller side 132 of the umbilical assembly 131).

The umbilical tube assembly 131 connects the control unit 102 with the UV light catheter assembly 140. The umbilical tube assembly 131 includes an outer sheath within which one or more electrical connection wires for LEDS within the UV light catheter assembly 140, electrical connection wires to a thermistor of the UV light catheter assembly, and warm and cold coolant tubings are disposed. The electrical connection wires and the cold and warm coolant tubings traverse along a length of the outer sheath. In some examples, the cold coolant tubing may include additional insulation to reduce heat transfer from the environment.

At a UV light catheter side 141 of the umbilical tube assembly 131, warm and cold coolant tubings and the one or more electrical connection wires (to the thermistor and the LEDs of the UV catheter assembly) exit as warm coolant connector 152, cold coolant connector 150, and electrical connector 148, which are coupled to corresponding warm coolant, cold coolant, and electrical connectors of the UV light catheter assembly 140 via a catheter-umbilical connection interface 141.

In one example, an umbilical tube assembly 131 may include one or more air passageways (e.g., warm coolant tubing for returning warm air from a light catheter assembly, a cold coolant tubing for providing cooled coolant to the light catheter assembly) and one or more electrical conductors (e.g., a power supply conductor for providing power supply to the light catheter assembly and/or a thermistor of the light catheter assembly). Further, the one or more electrical conductors may also provide an indication of a temperature of the light catheter assembly from the thermistor to the control unit. In response to the temperature, the control unit 102 may regulate one or more of an operation of the light catheter assembly and coolant flow to the light catheter assembly. The umbilical tube assembly may further include a light catheter connector configured to connect to the light catheter assembly and a control unit connector (or a compressor connector) configured to connect to the control unit (or a compressor system).

The umbilical tube assembly 131 may be approximately 4, 5, or 6 feet long or other suitable lengths to connect the UV light catheter assembly 140 to the control unit 102. The umbilical tube assembly 131 may be long enough to reach from a bedside cart containing the control unit 102 to the patient. As discussed above, the umbilical tube assembly 131 may include the electrical wires for the LEDs, wires for the thermistor, and tubings for the cooling air to the light catheter assembly 140 and/or tubings for warm air return from the light catheter assembly 140. Accordingly, in one example, the umbilical tube assembly 131 may connect the light catheter assembly 140 with the control unit 102 by functioning as a single hybrid connector for transmitting both gaseous coolant and electricity. For instance, a central passageway(s) may transmit air (e.g. cooling air down to the light catheter assembly 140, and if applicable, return, warm air up to the control unit 102 along a second passageway). Further, one or more electrical connectors/wires may be spaced around the periphery, or any configuration with respect to the air passageways.

In one example, the coolant is air. Accordingly, cooled air from the cooling unit 108 may flow through the cold coolant connector 136, the cold coolant tubing within the umbilical sheath, the cold coolant connector 150, and enter the UV light catheter assembly 140. In one example, air from the compressor 109 may be cooled by the chiller 111 (e.g., a thermoelectric cooler), and flowed in to the cold coolant connector 136. Further, warmed air from the UV light catheter is then routed back via the warm coolant connector 152, the warm coolant tubing within the umbilical 131, and the warm coolant connector 134, and from there on to the control unit 102 for recycling, monitoring flow rate, monitoring leaks, and/or expelling to the atmosphere. In some examples, the warm air may be expelled at a connection interface between the umbilical assembly 131 and the light catheter assembly 140 or via a valve regulated opening within the umbilical assembly. Details of coolant flow when the UV light catheter is deployed within a GI tract lumen is further described below at FIG. 7. In some examples, other gaseous coolants may be used and are within the scope of the disclosure.

The control unit 102 may include at least one processor (CPU) 103 and at least one memory 105 such as read-only memory ROM and/or random-access memory RAM, which comprise computer-readable media that may be operatively coupled to the processor. Thus, the at least one memory 105 may include system instructions that, when executed by the processor performs one or more of the operations described herein, such as one or more of cooling of the UV light catheter during operation of the UV light catheter, operation of the one or more balloons, and controlling operation of UV light and/or one or more balloons according to a temperature of the UV light catheter and/or balloon pressure. Processor 103 can receive one or more input signals from various sensory components (e.g., a thermistor coupled within the UV light catheter, a respective pressure sensor configured to sense pressure within each balloon) and can output one or more control signals to the various control components described herein (e.g., to the cooling system 108 within the control unit for regulating flow of coolant through a cooling tube of the UV light catheter, to a power supply coupled to the UV light catheter, to a pump of the balloon control unit 120 to adjust pressurization of the one or more balloons, etc.). The present example shows an example configuration of the control unit 102, but it will be appreciated that the control unit 102 may be implemented with other configurations.

In one non-limiting example, the control unit 102 may contain a medical grade air compressor such the Timeter PCS-414 by Allied, and may output 14 LPM of air at 50 psi or other suitable ranges. As discussed above, the control unit 102 may include a digital readout 104, a connector to the umbilical tube (that may be a hybrid connector), and user controls and status indicators. Additionally, the cooling system 108 may contain an air valve and pressure regulator. The control unit 102 may also contain pressure sensors and flow controls for the cooling air, and flow sensors. In some examples the control unit 102 may provide a closed feedback loop from the thermistors to determine the temperature and/or flow rate of cooling air delivered to the light catheter and through the cooling tube.

Referring to FIG. 2A, it shows a schematic illustration of a UV light catheter assembly 200 that may be coupled to an umbilical assembly, such as the umbilical 131 of FIG. 1B, of a UV light treatment system, such as the UV light treatment system 100 of FIG. 1B, and a control unit, such as control unit 102 of FIG. 1B, or coupled to the control unit without the umbilical assembly, as shown in FIG. 1A. Further, the UV light catheter assembly 200 may be an example of the UV light catheter assembly 140 shown at FIGS. 1A and 1B. In this example, the UV light catheter assembly 200 is shown in a released positon, not housed within a protective sleeve 126. Prior to deployment (that is, when the assembly 200 is not being prepared for deployment or being deployed), the UV light catheter assembly 200 may be housed within the protective sleeve 126.

The UV light catheter assembly 200 includes a delivery tube 202 (also referred to herein as housing catheter) comprising a light emitting portion 204. The light emitting portion 204 includes a plurality of LEDs 222. Further, the delivery tube 202 includes a plurality of balloons 230, 232, 234, and 236 at the light emitting portion 204. While the present example shows four balloons, the UV light catheter assembly may include fewer or more balloons. For example, a number of balloons may be 1, 2, 3, 4, 5, 6, or more. In some embodiments, the number of balloons may be more than two. That is, a minimum number of balloons may be three. For example, in a delivery device configured for administering UV light intraluminally in a large intestine, three or more balloons may be utilized.

In some examples, the number of balloons may be based on one or more of a total length of the UV light emitting portion, a total length of the delivery tube, and a length of an axis of each balloon that lies along the length of the light catheter (e.g., major axis when the balloon is shaped as an ellipsoid or a diameter of the balloon when the balloon is spherical).

In some examples, each balloon 230, 232, 234, and 236 may be positioned only on the light emitting portion 204, while the areas of the delivery tube 202 without the light emitting portion 206 (that is, without the UV LEDs) may not include any balloons. Thus, each balloon may cover a light emitting segment of the light emitting portion 206. The present example shows each light emitting segment having a length of 10 cm. In various embodiments, the light emitting segment covered by each balloon may be 5, 6, 7, 9, 10, 11, 12, 13, 14, or 15 cm, or other suitable lengths of the light catheter.

In some examples, as shown in FIG. 2A, the balloons may be positioned back-to-back with a minimal distance between a distal end of a first balloon 230 and a proximal end of a second balloon 232 immediately adjacent to the first balloon. However, in some examples, the UV light catheter assembly 200 may be configured such that relative spacing between the balloons on the delivery tube 202 may be adjusted. For example, a user may change the position of balloon 236 and/or balloon 234 as such that a distance between the balloon 234 and 236 increases. Thus, in some examples, some light emitting portions 206 may not be covered by the balloons. This adjustment of the spacing between the balloons may enable the user adjust balloon positioning to target specific areas for treatment. In particular, the spacing between the balloons may be adjusted before inserting in to a body cavity of the patient and navigating to the target site. In other words, the balloon position may be adjusted prior to deployment and not during deployment while the delivery tube is within the lumen.

As a non-limiting example, if an inflammation and/or an infectious condition is not continuous and is present in a first area and a second area of a large intestine separated by healthy tissue, the user may adjust balloon positioning such that when the delivery tube 202 is deployed within the lumen of the large intestine, the first balloon may align with the first area and the second balloon may align with the second area. For example, the first target area, the second target area, and the separation between the first and the second target areas may be identified by endoscopy. Subsequently, the balloon position may be adjusted on the UV light emitting portion. Further, a portion of the light emitting portion 206 of the delivery tube between the first and the second balloons may not be enveloped by any balloon. Accordingly, when the UV LEDs are powered ON, the first area and the second area that are infected and/or inflamed are treated with greater irradiance and irradiance distribution than the normal tissue in between. As discussed above, when inflated, an outer curved surface of the balloon may be in contact with the luminal epithelium, and facilitate removal of stool, debris, and/or a biofilm on the epithelium and further help stretch any folds and/or haustra, and prevent any stool and/or debris outside the treatment area from interfering with the treatment. Thus, the balloons may improve UV light distribution and an irradiance amount on the target tissues (that is, the first and the second areas in this example). As such, the when the UV LEDs are powered on, the first area and the second area (that is, the inflamed and/or infected areas) may receive UV light emitted from the UV LEDs through the balloons, and through the balloons, the first and the second areas may receive UV light with increased irradiance and irradiance distribution than the healthy tissues in between. In this way, the balloons further improve antimicrobial and/or anti-inflammatory effect provided by the UV light.

Furthermore, in some examples, the UV light catheter assembly may be configured such that only the UV LEDs that are present within the balloon areas are selectively powered ON during treatment, while the UV LEDs that do not are enveloped by the balloons may not be powered ON. In this way, the balloons may be utilized to not only provide uniform distribution and uniform intensity over the target areas, but also to provide selective treatment within the GI tract lumen.

In addition to adjusting positions of the balloons, an amount of pressurization of the balloons may be adjusted to provide selective treatment based on disease affected areas and/or extent of progression of the disease. For example, if a moderate ulcerative colitis is observed only in the sigmoid colon, the balloons 230, 232, 234, and 236 may be positioned with minimal spacing between them and after navigating the delivery tube 224 to the desired target area (e.g., such that the light delivery portion 206 and the balloons align with the desired target area), all the balloons may be pressurized to the desired pressure and the UV LEDs may be electrically powered at a desired intensity and for a desired duration to treat the desired target area for moderate ulcerative colitis. However, during some conditions, each balloon may be adjusted to a respective desired pressure based on one or more parameters of the target areas including a diameter of the lumen in the target area and/or extent of spread (that is area affected by the infection in the target area). The luminal diameter, in some examples, may be based on a degree of inflammation and/or infection in the target area.

Further, in some examples, as shown in FIGS. 3A and 3B, the areas between two balloons may not include LEDs. Turning to FIGS. 3A and 3B, they show a delivery tube 324 with light emitting segments 330, 332, 334, and 336 within the balloons 230, 232, 234, and 236. FIG. 3A shows the balloons 230, 232, 234, and 236 in a depressurized (that is, deflated) condition, and FIG. 3B shows the delivery tube 324 with the balloons 230, 232, 234, and 236 in a fully pressurized (that is, fully inflated) condition. In between the balloons, one or more areas 310 correspond to non-illuminating areas where no LEDs are positioned.

Further, as discussed above with respect to FIG. 1A, each of the balloons 230, 232, 234, and 236 may be pressurized to a desired pressure via a balloon control unit (e.g., balloon control unit 120 at FIG. 1A or FIG. 1B), which may be a pressure between a deflated pressure at the depressurized condition and a fully inflated pressure at the fully pressurized condition. The desired pressure may be set based on a diameter of the lumen in the target areas, and extent of spread of the infection and/or inflammation in the target area, for example. Further, in some examples, the desired pressure may be different for each balloon based on one or more parameters of the target areas as discussed above including the diameter of the target area and the extent of spread of the inflammation and/or infection. Further, in some other examples, the desired pressure may be set to the same pressure for all the balloons (e.g., similar diameter and similar target area).

Returning to FIG. 2A, the balloons 230, 232, 234, and 236 provide uniform distribution of UV light emitted by the UV LEDs 222 on the respective target areas, as indicated by broken arrows 212. Further, a proximal end 218 of the light catheter is not encased within the balloon. In some examples, as shown in FIGS. 3A and 3B, the proximal end 218 of the light catheter may be positioned within the proximal balloon 230.

Further, referring back to FIG. 2A, each balloon 230, 232, 234, and 236 may be fluidly coupled to respective inflation ports 231, 233, 235, and 237, which are coupled to a balloon control unit, such as the balloon control unit 120 discussed at FIG. 1A or FIG. 1B. This allows selective inflation, deflation, inflation rate, deflation rate, and/or pressure adjustment for each balloon during deployment.

Further, a distal end 221 of the light catheter assembly 200 is coupled to warm coolant, cold coolant, and electrical connectors of an umbilical (e.g., umbilical 131) via a connection port 216, which may be an example of connection port 154, to a catheter warm coolant connector (e.g., connector 152), a catheter cold coolant connector (e.g., connector 150), and a catheter electrical connector (e.g., 148) respectively. In this way, the umbilical brings in cooling coolant, power supply to a plurality of LEDs and power supply to a thermistor 228 of the UV light catheter assembly (via electrical connector 148). At the proximal portion, the UV light catheter assembly 200 includes the light emitting portion 206, which is shown enlarged at FIG. 7 and described further below.

Referring next to FIG. 2B, it shows a single balloon embodiment of the UV light catheter assembly. In this example, a single balloon 210 envelopes the light emitting portion comprising a plurality of LEDs 222. In some examples, the single balloon device may be utilized for treating gynecological conditions, including but not limited to bacterial or fungal vaginosis, rectovaginal/colovesical fistula, and/or cancers to mucosa and submucosa. In further examples, the single balloon device may be coupled a non-illuminating portion of a delivery tube, and depending on a total length of the delivery tube, the single balloon device may be navigated to a distal target site, such as rectum. The single balloon device may be used for ease of navigation to distal target (e.g., rectum or vagina) without the requirement for colonoscopy or sedation and may be administered in the physician office. In some other examples, a single balloon device with sufficient length of non-illuminating portion may be used to navigate to a single proximal target site, such as ascending colon, and treat infections and/or inflammation that are localized further away from a distal insertion site.

Further, as discussed above with respect to FIG. 2A where the delivery tube includes a plurality of balloons, an amount of pressure inside the single balloon 210 may be adjusted via balloon inflation port 204 which may be coupled to a balloon control unit, such as the balloon control unit 120 at FIG. 1A.

Other examples of single balloon devices are shown at FIGS. 4A and 4B. In particular, FIGS. 4A and 4B illustrate exemplary UV emitting devices 400 and 450 respectively that in some examples may be utilized for vaginal or rectal delivery of UV light. Referring to both FIGS. 4A and 4B, the UV emitting devices 400, 450 can include a delivery tube/rod 402. In some examples, the delivery tube/rod 402 includes a four-sided elongated body that includes UV light sources 422 (e.g., UV LEDs) on each of the four sides. In some other examples, the delivery tube/rod 402 may have a cylindrical body, and the UV light sources 422 may be positioned on the curved surface of the cylindrical body so as to deliver UV light along a circumference of the delivery tube for an entire length of the delivery tube. When the delivery tube is configured as the four-sided elongated body, the UV light sources 422 may be staggered on each side of the delivery tube/rod 100. While the example devices 400 and 450 show the delivery tube having four sides, the number of sides may be 3, 5, 6, 7 or 8. In some embodiments, the UV light sources 422 are distributed along the entire length of the delivery tube/rod 100, and at the distal end 410 to achieve a broader application of the UV light source 422.

In some embodiments, the delivery tube/rod 402 is configured such that the entire delivery tube/rod 402 glows and transmits UV light homogenously. In some embodiments, the delivery tube/rod 100 is configured to emit light waves in the UV-A range only, and not in the UV-B or UV-C or visible range. For example, the UV light sources 422 may be configured to emit narrow bandwidth UV light between 335 nm and 349 nm, between 338 nm and 342 nm, or between 339 nm and 346 nm. Further, a peak wavelength of the UV light sources 422 can include 340 nm and may lie within the ranges between 335 nm and 349 nm, or 338 nm and 342 nm, or 339 nm and 346 nm. In other broader embodiments, the light sources 422 may be configured to deliver UV light having wavelengths between 320 nm-410 nm. In some embodiments, the vertical illuminated length extends between 8-10 cm around the delivery tube/rod 100.

The delivery tube/rod 402 may be made of any suitable construction (e.g., rigid or flexible), including various polymers that are biocompatible or have a biocompatible coating. In some embodiments, the delivery tube/rod 402 can include an outer layer of UV transparent material 424 to allow the UV light from the light sources 422 to radiate outward from the delivery tube/rod 422. In some embodiments, the delivery tube/rod 402 may include an outer surface made from, e.g., silicon, silica, polyurethane, polyethylene, Teflon/PTFE, borosilicate, or other suitable materials. In some embodiments, the delivery tube/rod 402 is constructed using copper with a borosilicate outer layer. For optimal cooling, area of exposure, and uniformity, the delivery tube/rod 402 can include multiple light emitting diodes (LEDs) staggered on a copper bar. The spacing of the light sources 422 enables an optimal vertical illuminated length. By manufacturing the body of the delivery tube/rod 422 using copper, the delivery tube/rod 402 is able to withstand reaching elevated levels in temperature. The copper serves as a heat sink, preventing the delivery tube/rod 402 from reaching uncomfortable temperatures. In some examples, the light sources 422 may be operated at specific currents to optimize the temperature of the delivery tube/rod 402. In some examples, the light sources 422 are operated within the range of 60-100 mA. Within this range, the temperature of the delivery tube/rod 402 may not raise above 40° C., therefore achieving the goal of implementing a proper cooling solution. In some examples, additionally or alternatively, the base 412 and/or the handle 430 may be configured to include one or more fans to dissipate heat from the delivery tube/rod.

Further, the UV light emitting devices 400, 450 may each include an inflatable balloon 410 over an entire length of the delivery rod/tube 402. The balloon 410 when inflated may provide more uniform distribution of the UV light over a target area within the patient. Further, in some examples, the balloon 410 may increase irradiance as well as provide a more uniform irradiance distribution at the target area. Further, the balloon may facilitate disruption of extraneous debris/biofilm that may act as a barrier between the light catheter and the epithelial layer, thereby improving UV light irradiation and irradiation distribution at the target tissues. The balloon 410 may be made of any suitable material that is expandable and UV-transparent and improves UV-irradiation distribution, and in some examples, the material may increase irradiance at the target area. Example materials may be composed of PEBA, COC, or silicone.

The balloon 410 may be coupled to an inflation port 404 which is coupled to a balloon control unit 420. The balloon control unit 420 may be configured to pressurize and depressurize the balloon during deployment. The balloon control unit 420 is similar to the balloon control unit 120 described at FIG. 1A, and its description will not be repeated for the sake of brevity. Briefly, the balloon control unit 420 may include a pressure sensor for monitoring a pressure within the balloon 410. Further, the balloon control unit 420 may include a pump system (e.g., a syringe-based pump system or a motorized pump system) to pressurize and depressurize the balloon. Further, the balloon control unit 420 may be used to maintain the balloon 410 at constant or nearly constant pressure and volume during deployment of the delivery rod within the patient and during delivery of the UV light treatment. Further, the balloon control unit 420, using input from the pressure sensor, may not allow pressurization of the balloon 410 beyond a threshold limit. In some examples, prior to insertion and positioning within the patient, the balloon 410 may be inflated, via the balloon control unit 420, to a first lower volume, which may facilitate insertion and positional adjustment of the delivery rod/tube 402. Upon navigating to the desired position within the patient, the balloon 410 may be inflated to a second higher volume allowing the balloon to expand further. Subsequently, the UV light sources 422 may be powered ON to deliver UV light. During treatment when the UV light is being delivered to the patient, the balloon volume and pressure may be maintained constant by the balloon control unit 420. Thus, via the balloon control unit 420, one or more balloon parameters, including volume, pressure, and temperature, may be monitored and adjusted to maintain desired expansion.

The delivery tube/rod 402 includes a proximal end 408 and a distal end 410. The four sides of the elongated body 402 converge into a rounded surface 104 towards the distal end 409. The distal end 409 of the delivery tube/rod 402 is configured for insertion into a patient, as discussed above. In contrast, the opposing proximal end 408 is configured for maneuverability of the delivery tube/rod 402 via a gripping element. In one example, the proximal end of the delivery tube/rod 402 may be coupled to the gripping element that is configured as a handle 430 (FIG. 4A). Referring to FIG. 4A, the handle 430 may be attached to the delivery tube/rod 402 at the proximal end 408 via a base 412. The handle 430 may be configured to be ergonomically sufficient for a physician or a medical provider. The handle 430 may also include one or more input components 432 (e.g., power ON/OFF button, intensity selection button, duration selection button etc.) configured to receive a user's inputs. The input components 432 can be connected to an internal processor that alters the functionality of the delivery tube/rod 402 and the UV light sources 422. In some embodiments, the delivery tube/rod 402 includes between 2 and 20 UV light sources. The delivery tube/rod 402 illustrated herein includes three UV light sources 422 on each side of the four sides, for a total of twelve (12) UV light sources 422. It should be understood that other configurations are feasible incorporating the features disclosed herein.

In some embodiments, the handle 430 may include a rotating base (not shown) at its proximal end opposite to the delivery tube/rod coupling end. The rotating base can enable rotation of the delivery tube/rod 402 such that light emitted from the UV light sources 422 is uniform. When treating a patient with a rotating delivery tube/rod 422 the uniform UV emittance is likely to assist in treating microbial growth. In some examples, the delivery tube/rod 402 or the rotating base may also include a stepper motor to enable the rotation of the rotating base.

Referring to FIG. 4B, the example UV light delivery system 450 includes a controller 460 coupled to the base 412. In this example, the base 412 may be configured to function as a handle. The controller 460 may include one or more processors, memory, and a battery or other power source. The memory may contain instructions with various therapy regimens that may be applied using various intensities and/or durations as disclosed herein. For instance, the memory may contain data structures that when executed by a processor, provide power to the light sources 422 with a given intensity or timing. The controller may be utilized for any of the embodiments disclosed herein, including the vaginal, and GI tract based UV light delivery device.

Next, FIG. 5A shows a flow chart illustrating a high level method 500 for treating, preventing, and/or ameliorating an infectious and/or inflammation condition using a UV light catheter assembly. In particular, method 500 may be performed using a UV light treatment system, such as the UV light treatment system 100 described at FIG. 1A or 1B, the UV light catheter assembly described at FIG. 2A, 2B, 3A, or 3B, or the UV light emitting device described at FIG. 4A or 4B. While the method 500 will be described with respect to FIG. 1A, FIG. 1B, FIG. 2A, FIG. 2B, FIG. 3A, or FIG. 3B, it will be appreciated that the method 500 may be applied to other similar UV light treatment systems without departing from the scope of the disclosure.

At 502, the method 500 includes evaluating a GI tract health condition. Evaluating the GI tract health condition may be performed by a health care provider based on one or more of symptoms, an endoscopic procedure, such as colonoscopy with or without biopsy, blood analysis, and stool analysis, among other diagnostic procedures.

Evaluating the GI tract health condition may include determining a type of GI tract inflammatory and/or infectious condition. Example GI tract inflammatory and/or infectious condition may include ulcerative colitis, Crohn' disease, and other chronic inflammatory diseases, non-IBD related proctitis, IBD or non-IBD related fistula, inflammatory strictures, microscopic colitis, infectious diarrhea, refractory *Helicobacter pylori* and MALT lymphoma, esophageal lichen planus and pemphigus vulgaris, refractory *Clostridium difficile*, colonic inertia, tropical sprue, celiac disease, small intestinal bacterial overgrowth, typhlitis post-bone marrow transplant infections, pseudopolyps (similar to nasal polyps) and radiation enteritis, Barrett's esophagus with or without dysplasia, hepatic encephalopathy, blind loop syndrome in Roux-en-Y, perianal fistulas, gastrointestinal cancers, hepatobiliary infections, inflammation and cancers.

Further, the method 500 will be described further below with respect to ulcerative colitis and Crohn's disease forms of inflammatory bowel diseases (IBD); however, it will be appreciated that the method 500 may be performed to treat, ameliorate, and/or prevent any inflammation and/or infectious condition of the GI tract without departing from the scope of the disclosure. In some examples, the method 500 may be applied to reduce a rate of infection associated with percutaneous feeding or suction tubes. In some other example, the method 500 may be performed using a UV light emitting device configured for vaginal and/or rectal applications, such as the example systems shown at FIGS. 5A and 5B.

Further, evaluating the GI tract health condition may include determining a degree of progression of the inflammatory and/or infectious condition. For example, the degree of progression may be determined based on a suitable scale (e.g. mild, moderate, severe etc.) based on the disease. In some examples, evaluating the GI tract health condition may further include determining which layer of the GI tract tissue is affected. For example, when a large intestine of a patient is evaluated, the method 500 may include determining if the inflammatory and/or infectious condition is at one or more of mucosal layer, submucosal layer, muscular layer, and serosa layer.

Further, at 504, the method 500 includes identifying one or more target areas that require UV light treatment. For example, when evaluating a large intestine for ulcerative colitis, an imaging approach, such as colonoscopy may be used to identify which areas of the intestine are affected. In some examples, based on the symptoms and one or more non-invasive or minimally invasive tests, a portion of the colon (e.g., via sigmoidoscopy for examining rectum and lower portion of the large intestine) or the entire colon (e.g., via colonoscopy) may be evaluated.

Next, at 506, the method 500 includes positioning a delivery tube of a UV light catheter assembly comprising a plurality of light sources (e.g. UV-LEDs) and a plurality of balloons, such the delivery tube 202 at FIG. 2A or the delivery tube 324 at FIG. 3A, in order to treat the one or more target areas with UV light. An example method for positioning the delivery tube within a large intestine is illustrated and described with respect to FIGS. 6A-6G. In one example, deployment of the delivery tube may be performed via colonoscopy using a guidewire based on Seldinger technique.

Figure 6A:
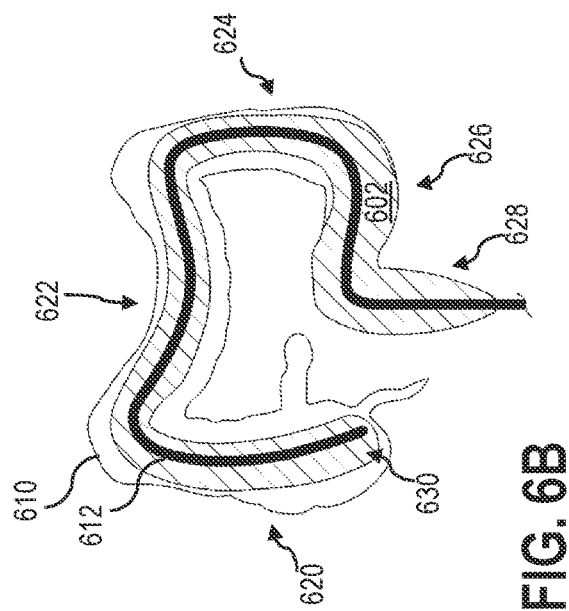
FIGS. 6A-6G shows schematic illustrations depicting deployment of an example delivery device including a plurality of LEDs and a plurality of distendable balloons within a lumen of a large intestine, according to an embodiment of the present disclosure.
Figure 6B:
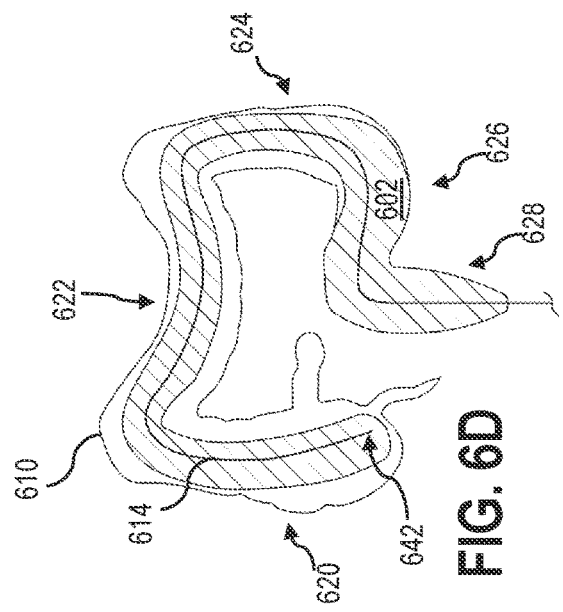

Turning to FIGS. 6A-6G, the figures depict schematic illustrations showing cross-sections of a large intestine 610 during various stages of deployment of a delivery tube of a UV light catheter assembly. FIG. 6A shows the large intestine 610, including a lumen 602, prior to initiating the deployment procedure. FIG. 6B shows the insertion of a colonoscope 614 to an ascending colon 620 of the large intestine 610. For example, during deployment of the delivery tube, prior to inserting and positioning the delivery tube, the colonoscope 614 is inserted through the lumen of the large intestine 610 up to a desired location within the lumen of the large intestine for viewing the large intestine and subsequently positioning a guide wire. While FIG. 6B shows insertion of the colonoscope 614 in to the lumen of the ascending colon 620 up to a proximal region 630 of the ascending colon 620, the colonoscope may be inserted up to any location within the lumen of the large intestine 610, such as to any location within the ascending colon 620, the transverse colon 622, the descending colon 624, the sigmoid colon 626, or rectum 628.

Figure 6C:
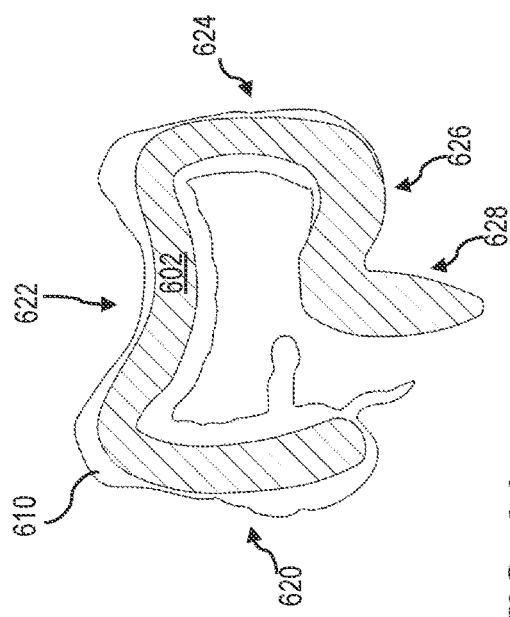
Figure 6D:
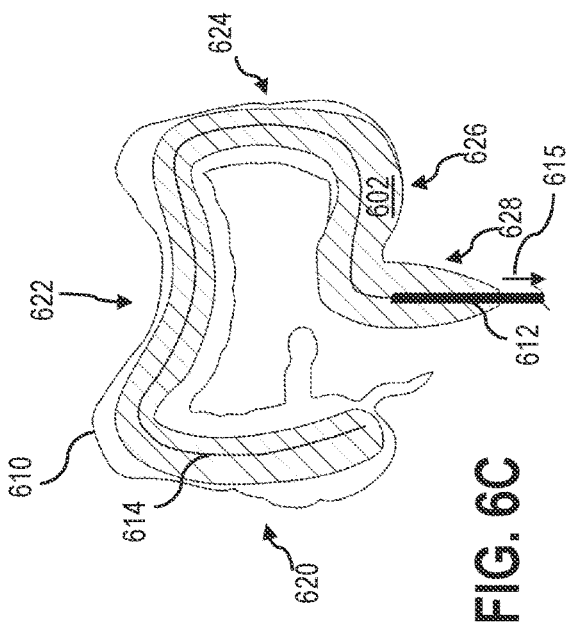

Next, upon inserting and positioning the colonoscope 612, a guide wire 614 is inserted through a channel of the colonoscope 612 (FIG. 6C). The guide wire 614 traverses through the channel of the colonoscope 612 and exits from an opening at an end portion of the colonoscope 612 that is located in the ascending colon in this example. Thus, the colonoscope is used to view the lumen as well as position the guide wire 614 to the desired location to facilitate final positioning of the UV light catheter. Upon inserting the guide wire 614, the colonoscope 612 is withdrawn (indicated by arrow 615) from the lumen as shown at FIG. 6C. In this way, the colonoscope 612 is utilized to position the guide wire 614 within the lumen of the large intestine 610. In this example shown at FIG. 6C, the colonoscope is used to the guide wire 614 are position the guide wire 614 in to the ascending colon 620. It will be appreciated that the guide wire 614 may be positioned anywhere within the lumen of the large intestine 610. FIG. 6D shows the guide wire 614 positioned in the lumen of the large intestine 610 through the colonoscope 612 such that a proximal end 642 of the guide wire is positioned in the ascending colon 620. As discussed above, the guide wire 614 may be positioned anywhere within the lumen of the large intestine 610 based on the location and/or extent of spread of the infection and/or inflammation. As a non-limiting example, if a patient is diagnosed with ulcerative colitis in the left semicolon (left-sided colitis), the guide wire 614 may be positioned such that the proximal end 642 of the guide wire 614 may be positioned at a beginning portion of the transverse colon 622 (the beginning portion adjacent to the descending colon) or at an end portion of the descending colon 624 (the end portion of the descending colon adjacent to the transverse colon). As another non-limiting example, for a patient diagnosed with pockets of inflammation separated by healthy tissue, including inflammation in a portion of the transverse colon and a portion of the descending colon, the guide wire 614 may be positioned such that the guide wire 614 traverses through the rectum, the descending colon and the transverse colon and proximal end of the guide wire 614 ends at or downstream (downstream in the direction from descending to ascending colon) beyond the inflammation region in the transverse colon.

Figure 6E:
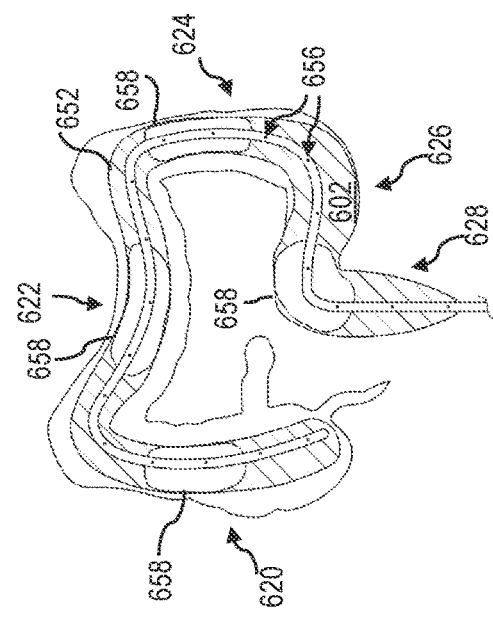

Upon positioning the guide wire 614 and retracting the colonoscope, a delivery tube 652 of a UV light catheter assembly is inserted into to the lumen of the intestine using the guide wire 614. FIG. 6E shows the delivery tube 652 positioned over the guide wire 614 (not shown in FIG. 6E). The delivery tube 652 is an example of the delivery tube 202 or delivery tube 324 described above. The delivery tube 652 may include a guide wire channel (e.g., guide wire channel 160 at FIG. 1A) for the guide wire to pass through. After positioning the guide wire 614, the delivery tube 652 comprising a plurality of UV LEDs 656 and a plurality of balloons 658 is navigated through the lumen of the large intestine 610 by passing the guide wire channel of the delivery tube over the guide wire 614 positioned in the large intestine 610. In one example, all of the plurality of balloons, such as balloons 232, may be in a deflated condition while navigating the delivery tube in the lumen. In some examples, a first balloon that is at an end of the delivery tube 652 (entering the lumen first) may be partially inflated its respective balloon inflation port coupled to a control unit 660 to facilitate movement of the delivery tube 652 while the remaining balloons remain in the deflated condition while navigating the delivery tube 652. As a non-limiting example, when the delivery tube 652 is to be navigated through a majority of the colon and an end positioned at the ascending colon (e.g., to treat and/or ameliorate extensive colitis throughout the colon), first balloon at or near the end 659 of the delivery tube 652 may be partially inflated while the remaining balloons are in the deflated condition during navigation and positioning. In some examples, more than one balloon may be partially inflated during deployment, for example to facilitate traversing the hepatic and/or the splenic fixtures.

The control unit 660 may be an example of control unit 102 discussed at FIG. 1A, and thus may include a balloon control unit for monitoring and/or adjusting pressurization and depressurization of the plurality of balloons 658. Also as discussed with respect to FIG. 1A, the control unit 660 may adjust operation of the UV LEDs 656 (e.g., power on/off, selective powering of one or more segments of UV LEDs corresponding to treatment areas and/or balloon deployment, UV light intensity adjustment, UV light intensity cycling, etc.) and provide temperature control of the delivery tube 654 during deployment and treatment (e.g., temperature adjustment based on UV LED temperature from one or more thermistors positioned within the light emitting portion and using coolant flow from the compressor of the control unit into a cooling tube within the delivery tube).

While the above example illustrates using a colonoscope and a guide wire to deploy the delivery device, in some examples, the delivery tube may be configured as an endoscope (e.g., colonoscope) comprising one or more cameras for visualizing the interior of the lumen.

Retuning to FIG. 5A, after positioning the delivery tube (that is, the UV light catheter) within the lumen such that one or more balloons align with the treatment site, the method 500 proceeds to 510. At 510, the method 500 includes inflating the one or more balloons. In one example, a number of balloons inflated may be based on the treatment areas. For example, only the balloons that align with infected and/or inflamed areas that require UV light treatment may be inflated while the other balloons that align with normal tissue may not be inflated. However, in some examples, depending on the extent of insertion of the delivery device into the colon, one or more additional balloons that align with normal tissue may be inflated to stabilize the colon and potentially reduce any unwanted reflex movements of the colon, as well as to stabilize the delivery device, thereby reducing unwanted movements of the delivery device. For example, when the delivery device with plurality of balloons is navigated to the ascending colon and the treatment site is at the ascending colon and the transverse colon, in addition to inflating the balloons that align with the treatment site at the ascending colon and the transverse colon, if additional stabilization of the delivery device is desired, one or more balloons that align with normal tissue may be inflated. In such cases, the amount of inflation may be reduced (e.g., less that the amount of inflation in the balloon aligning with the normal healthy tissue areas)

In one example, inflating the one or more distendable balloon includes pressurizing each of the one or more distendable balloons to a threshold pressure at which each of the one or more distendable balloons is in direct contact with a desired surface area of an epithelial layer of the lumen. In one example, the threshold pressure may be based on a diameter of the lumen at the target site. In one example, the desired surface area is based on an extent or spread of infection. In one example, the threshold pressure is sufficient to dislodge one or more of debris, stool, and biofilm on the surface of the epithelial layer of the lumen.

In some examples, in addition to selectively inflating one or more balloons, the method 500 may include selectively adjusting an intensity of light (discussed below at 514) within each balloon based on an extent of disease progression at the treatment areas. In particular, as a severity of infection and/or inflammation of the treatment site increases, intensity of UV light emitted may be increased. As a result, an irradiance amount at the target site is increased with increasing disease severity.

Figure 6F:
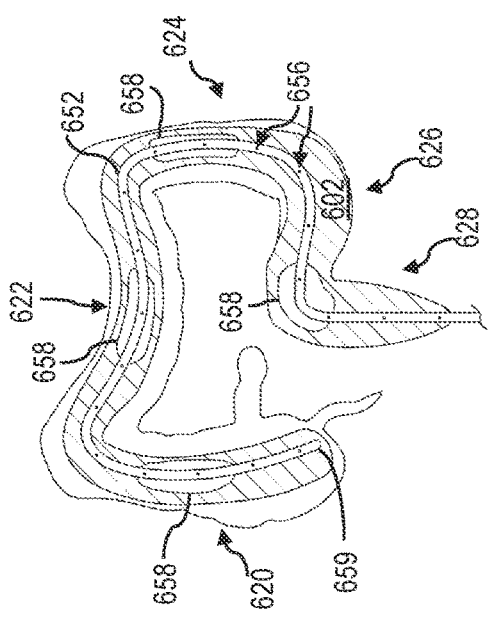

Turning to FIG. 6F, it shows all the balloons 658 after inflation. In particular, upon positioning the delivery tube 652 over the guide wire, the plurality of balloons 658 are inflated by providing inflation fluid (e.g., air) to the balloons 658 via their respective balloon inflation ports and the balloon control unit 660. While the present example at FIG. 6F shows all the balloons inflated, in some examples, one or more balloons 658 may be selectively inflated based on treatment areas. As a non-limiting example, if the treatment areas are in the ascending colon and the transverse colon, but not the descending colon, the first balloon in the ascending colon 620 and the second balloon in the transverse colon 622 may be inflated while the third balloon in the descending colon 624 and the fourth balloon in the sigmoid colon 626 may not be inflated or inflated to a lesser amount (e.g., for delivery device stabilization) than the first and the second balloons.

Further, in some examples, as shown at FIG. 6F, all the balloon 658 are inflated to a same amount of pressure via respective balloon inflation ports (not shown) and using the balloon control unit 660.

In some other examples, an amount of inflation may be adjusted independently for each balloon. In one example, the amount of inflation may be based on a diameter and/or extent of spread of infection and/or inflammation of the treatment area.

Taken together, one or more balloons may be selectively pressurized (that is, one or more balloons are pressurized while the remaining balloons are not pressurized) based on a number of treatment areas and/or location of the treatment areas. Additionally or alternatively, when inflated, an amount of expansion in each of the inflated balloons (whether all of the balloons are inflated or one or more balloons are selectively inflated) may be selectively adjusted (e.g., by adjusting an amount of inflation via the balloon control unit) based on one or more of diameter and extent of treatment area. Further, in addition to selective balloon inflation, one or more UV light parameters may be adjusted during deployment as discussed further below. In this way, UV light therapy may be customized through selective operation and/or adjustment of the balloons depending on one or more of location, severity, and extent and pattern of spread of infection and/or inflammation.

Referring back to FIG. 5A, at 514, the method 500 includes providing UV light treatment after inflating the one or more balloons. Providing the UV light treatment includes adjusting one or more of an intensity of the UV light emitted from the UV LEDs within the delivery device, and a duration of the UV light emitted from the UV LEDs. In one example, adjusting one or more of an intensity and a duration of the UV light emitted from the UV LEDs may include adjusting one or more of intensity and duration for each balloon based on an extent and/or severity of inflammation and/or infection at the corresponding treatment areas (step 516). For example, duration and/or intensity of light output from UV LEDs may be increased in one or more segments of the delivery device that treat more severe conditions compared to segments that treat less severe infections and/or inflammations. The intensity and duration adjustment may be performed in addition to or alternative to adjusting an amount of inflation in the corresponding balloon over the segment delivering UV light to the treatment area.

In some examples, all of the LEDs in the light emitting portion may be operated at the same intensity and/or duration based on an overall severity of the disease condition.

In some examples, the UV wavelengths that provide sufficient antimicrobial effect without causing UV-related DNA damage may include one or more of the following: 335, 336, 337, 338, 339, 340, 341, 342, 342, 344, 345, 346, 347, 348, 349, or 350 nm. Accordingly, the UV LEDs as disclosed herein may emit light with one or more of the preceding wavelengths at intensities that are therapeutically significant. Further, by using the balloon for improving UV light distribution and increasing irradiance at the target areas, effectiveness of the UV light treatment is further improved while being safe for treatment over a broad area (e.g., entire colon) within the GI tract of the patient.

In some examples, a length of GI tract lumen treated using the UV light catheter assembly may be in a range between 5 cm to 45 cm. In some examples, treatment sites having lengths greater than 40 cm may be treated using the delivery device.

In some examples, the delivery tube with LEDs emitting light having wavelengths of maximum emission intensity centered around 339, 340, 341, 342, 343, 344, 345, 346, 347, 348 or 349 nm may be energized for at least 15, 16, 17, 18, 19, 20, 21, 22, 23, 24, 25, 26, 27, 28 29, 30, 40, 60, 80, or 90 minutes. Repetition of the treatment may be based on disease progression, symptoms, and/or other evaluations performed by the health care provider. The intensity applied may be 1500, 1600, 1700, 1800, 1900, 2000, 2100, 2200, 2300, 2400, 2500, 2600, 2700, 2800, 2900, 3000, 3100, 3200, 3300 uW/cm$^2$, or other suitable intensities between these ranges based on a severity of infection.

In some examples, each of the plurality of UV LEDs may emit a peak wavelength of 335 nm, 336 nm, 337 nm, 338 nm, 339 nm, 340 nm, 341 nm, 342 nm, 343 nm, 344 nm, 345 nm, 346 nm, 347 nm, 348 nm, 349 nm, 350 nm, 351 nm, 352 nm, 353 nm 354 nm, 355 nm. In some examples, the LEDs may emit light with significant intensity in a range of +/−2, 3, 4, 5, or 6 nm around its peak intensity emission wavelength.

In some examples, each of the LEDs may emit light with a beam angle between 100 and 150 degrees. In one example, each of the LEDs may emit light with a beam angle between 120 and 135 degrees.

In other examples, the light therapy may be delivered by a caregiver for 10 minutes, 15, minutes, 18 minutes, 19 minutes, 20 minutes, 21 minutes, 22 minutes, 23, minutes, 24 minutes, 25 minutes, 26, minutes 27 minutes, 28 minutes, 29 minutes, 30 minutes, 60 minutes, 90 minutes, 120 minutes, or 160 minutes, any range of minutes between 10 and 160 minutes or other suitable times. In addition, methods of the invention can include administering therapy for a threshold duration of at least 10 minutes, 15, minutes, 18 minutes, 19 minutes, 20 minutes, 21 minutes, 22 minutes, 23, minutes, 24 minutes, 25 minutes, 26, minutes 27 minutes, 28 minutes, 29 minutes, 30 minutes, or 60 minutes. The light source intensity may be at least 1,000 microWatt/cm$^2$, 1,100 microWatt/cm$^2$. 2,000 microWatt/cm$^2$. 2,100 microWatt/cm$^2$, 2,200 microWatt/cm$^2$. 2,300 microWatt/cm$^2$, 2,400 microWatt/cm$^2$, 2,500 microWatt/cm$^2$. 2,600 microWatt/cm$^2$, 2,700 microWatt/cm$^2$. 2,800 microWatt/cm$^2$. 2,900 microWatt/cm$^2$, 3,100 microWatt/cm$^2$, 3100 microWatt/cm$^2$, 3,200 microWatt/cm$^2$. 1,000-5,000 microWatt/cm$^2$ or other suitable intensities depending on the application and other factors relevant to the treatment effectiveness. The inventors have confirmed that application of UV-A light is safe at intensities of up to 5,000 microWatt/cm$^2$. In some examples, the light will be delivered continuously and in other examples it will be incorporated into pulse therapy.

Example operation of providing UV light within the lumen of the large intestine is described below with respect to FIG. 6G.

Figure 6G:
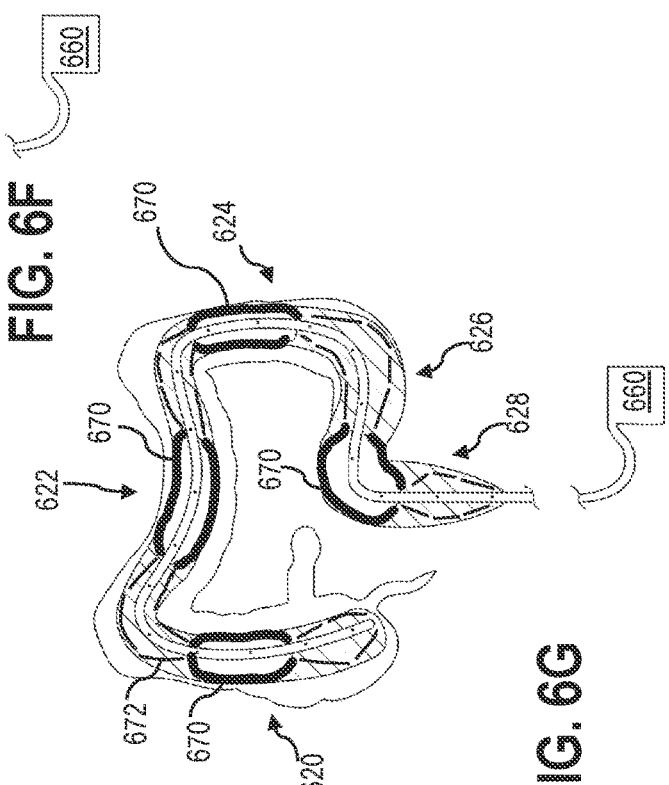

FIG. 6G shows the delivery tube 654 including the plurality of UV LEDs powered ON. Prior to initiating UV light treatment, upon inflating the one or more balloons, the guide wire is removed. Next, upon inflating one or more balloons 658, the UV LEDs are powered ON illuminating the treatment sites through the corresponding balloons. Additionally, in some examples, the UV LEDs that are not covered by the balloons may also be powered ON thereby illuminating the balloon adjacent areas. The UV light emitted by the UV LEDs is transmitted through the inflated balloons 658 on to the treatment site. As shown by thicker lines 670, the balloon increases the irradiance at the treatment site and additionally, improves UV light distribution at the treatment site. Further, the plurality of balloons 658, when inflated and in contact with the mucosa, may reduce folds, and facilitate diffusing any potential biofilm or extraneous debris formed on the colonic epithelium and reduce any barriers that may prevent UV light from effectively reaching the colonic epithelium. Furthermore, the plurality of balloons 658 may reduce stool from descending on to the treatment area.

In this way, the UV light catheter assembly with the balloons improves efficiency and effectiveness of the UV light treatment with the GI tract. Further still, the plurality of balloons 658 when inflated to be in contact with the colonic epithelium, may stabilize the walls of the colon as well as the delivery device within the lumen and reduce injuries caused during the deployment of the delivery device and during treatment.

FIG. 5B shows a high-level flow chart illustrating an example method 550 for adjusting one or more of a balloon inflation amount and UV light intensity during UV light treatment delivered within a lumen of a GI tract of a patient using a UV light catheter assembly such as the UV light catheter assembly discussed at FIG. 1A, 2A, or 3A. In some examples, upon energizing the UV LEDs within the UV light catheter assembly, the method 550 may be executed by a controller, such as controller 103, based on executable instructions stored in a memory, such as non-transitory memory 105, of a control unit, such as control unit 102, in conjunction with a balloon control unit, such as the balloon control unit 120, and one or more sensors (e.g., thermistor) coupled to the UV light catheter assembly.

At 552, the method 500 includes providing UV light treatment to the patient, as discussed above at FIG. 5A. Next, at 554, the method 500 includes determining whether the treatment regimen is complete. For example, a user may set a treatment regimen that includes providing a UV light treatment for 20 minutes at a desired intensity of UV light emitted from the plurality of LEDs (e.g., LEDs 222 at FIG. 2A). The controller may monitor the duration of light treatment, and the treatment may be determined to be complete responsive to a timer monitoring the duration reaching a zero value. If the treatment regimen is complete, the method 550 proceeds to 562. At 562, the method 550 includes stopping electrical power supply to the LEDs, and subsequently at 564, the method 550 includes deflating one or more balloons that were inflated. In one example, the one or more balloons may be completely deflated. In another examples, such as when the delivery tube is to be navigated through hepatic and/or splenic flextures during removal of the delivery tube from the patient, the one or more inflated balloons may be partially deflated to maintain a lesser volume of the one or more balloons, in order to facilitate traversal of the delivery tube through the lumen of the GI tract, and to reduce contact of the delivery tube with the colonic epithelium, thereby reducing potential injuries due to the delivery tube providing the light treatment. Upon deflating the one or more balloons (either partially or fully), the user may remove the delivery tube from the lumen.

Returning to 554, if the answer at 554 is NO, the UV light treatment is ongoing and the method 550 proceeds to 556 to continue providing UV light. This includes, at 558, monitoring one or more of a delivery tube temperature and a pressure within each of the one or more balloons. The temperature of the delivery tube may be monitored based on signals from a thermistor, such as thermistor 228, positioned within the delivery tube and outputting delivery tube temperature. In one example, as shown at FIG. 2A, the thermistor 228 may be positioned at an end of the light emitting portion; however, it will be appreciated that the thermistor 228 may be positioned at any location within the light emitting portion of the delivery tube. In some examples, each light emitting segment (of the light emitting portion) coupled to a balloon may include a thermistor to monitor temperature corresponding to each light emitting segment enveloped by the balloon. For example, each light emitting segment 330, 332, 334, 336, at FIG. 3A may each include a thermistor in order to monitor temperature within respective light emitting segments that lie within balloons 230, 232, 234, and 236.

Further, a pressure within each balloon may be monitored via a pressure sensor in fluid communication with respective inflation ports. That is, each balloon inflation port is fluidly connected to a respective pressure sensor, and pressure signals from each pressure sensor may be received and monitored via the balloon control unit and/or the controller. Through the pressure sensor, the controller may monitor leakage from the balloon. Further, in some examples, in conjunction with the thermistor, pressure sensor may be used to monitor temperature in individual light segments corresponding to the balloon.

Further, at 560, method 550 include adjusting one or more of UV light intensity, duration, and/or a balloon inflation amount based on one or more of the delivery tube temperature and the respective pressure within each balloon. For example, when a temperature within a balloon increases, due to expansion of air resulting from the temperature increase, a pressure within the balloon may increase. Responsive one or more of a temperature increase above a threshold and a pressure increase above a threshold pressure, the controller may adjust an actuator to increase coolant flow and/or depressurize such that the pressure within the balloon is within the threshold pressure (e.g., to ensure desired contact of the balloon with the epithelium without exerting excessive pressure). In some examples, the threshold pressure may be different for balloons treating different diameters of treatment areas. For example, threshold pressure may be higher for balloons treating target areas with larger diameter.

In some examples, additionally or alternatively, the UV light intensity or duration may be adjusted via the controller.

The method 550 then returns to 554.

In one non-limiting example, the narrow-band UV light treatment through the one or more balloons is provided to treat inflammatory and/or infectious conditions affecting only the mucosal layer and/or the submucosal layer of the gastrointestinal tract. In another example, additionally or alternatively to mucosal and/or submucosal layers, the narrow-band UV light treatment through the one or more balloons is provided to treat inflammatory and/or infectious conditions affecting one or more deeper layers further away from the intestinal lumen than the mucosa and/or submucosa. The one or more deeper layers may include the muscularis propia and/or the serosa.

Turning to FIG. 7, it shows a schematic illustration of the light emitting portion 206 of the delivery tube including example positioning of the LEDs 222 and the cooling tube 224 within the delivery tube 202 along with coolant flow indications. The balloons are not shown in this example. In particular, the light emitting portion 206 includes the plurality of LEDs 222 disposed inside the delivery tube 202, and the cooling tube 224 also disposed inside the delivery tube 202. In one example, as shown, the LEDs 222 are positioned rotated 90 degrees from each other and facing the delivery tube 202 such that when the LEDs 222 are electrically powered, the LEDs 222 emit light in a 360 degree pattern outward from the delivery tube 202 along a length of the delivery tube 202. Further, in this example, each adjacent LED is rotated 90 degrees. For example, a first LED is at a reference angle of zero degrees, a second LED positioned adjacent to the first LED (that is, the second LED immediately next to the first LED) along a length of the delivery tube 202 is rotated 90 degrees from the first LED. Further, a third LED adjacent to the second LED along the length of the delivery tube 202 is rotated 90 degrees with respect to the second LED (which is, 180 degrees with respect to the first LED), and so on such that a Nth LED adjacent to a (N−1)th LED is rotated 90 degrees with respect to the Nth LED, where N is any number depending on a desired length of light emission along the delivery tube 202.

In some examples, the LEDs may be arranged in a circumferential configuration. For example, 4 LEDs may be arranged at 90 degrees from each other such that a first LED and a third LED are positioned back-to-back and a second and a fourth LED are back-to-back, the second LED between the first and the third LED, and the fourth LED between the third and the first LED, and the 4 LEDs are not staggered and when electrically powered, the 4 LEDs emit a light at 360 degrees around a circumference of the delivery tube 202. Another set of 4 LEDs may be positioned at a small distance from the 4 LEDs to provide continuous substantially uniform illumination over a desired length of the delivery tube 202. In this way a plurality of sets of LEDs may be positioned to cover a desired length of the catheter tube for illumination. Other configurations of the LEDs that cover 360-degree illumination along a desired length of the catheter tube are possible, and are within the scope of the disclosure. For example, when LEDs with a wider beam angle are used, fewer than 4 LEDs may be used to provide 360-degree illumination. As a non-limiting example, 3 LEDs, each rotated 120 degrees from each other, arranged in a staggered manner (that is, adjacently positioned along a length of the tube) or in a circumferential manner (that is, adjacently around a circumference of the cooling tube) may be utilized. In this way, sets of 3 LEDs may provide 360-degree illumination.

Further, the cooling tube 224 is positioned within the delivery tube 202 and brings in cooling air to the delivery tube 202. The delivery tube 202 has an open end 704 towards the proximal end 218 of the catheter tube through which cooling air exits from the cooling tube and circulates back towards the LEDs to cool the LEDs (cooling air flow is shown by arrows 702). The cooling tube 224 may be configured to receive cooling air from a compressor, such as compressor 108 at FIG. 1A. The cooling tube 224 is positioned centrally with respect to the LEDs 222. In particular, the LEDs 222 are positioned such that a portion of each LED is in contact with the cooling tube 224. For example, the LEDs 222 are arranged such that a back portion (e.g., a portion of a LED substrate) is in contact with the cooling tube 224. In some examples, the LEDs 222 may be positioned on an inner tube (e.g., tube 324 at FIGS. 3A and 3B) that may include one or more cooling tubes within the inner tube.

Further, the cooling tube 224 is flexible and winds through the back portions of each LED, which allows for the LEDs to be arranged in a compact manner. In some examples, one or more additional openings may be provided for the cooling tube to allow cooling air to exit from one or more additional exit points.

FIGS. 8, 9A-9C, 10A-10B, 11A-11C, and 12 illustrate a few different embodiments that may be employed for a light emitting portion of a delivery tube which may be coupled to one or more balloons. This may include, as shown in FIG. 8, one or more Chip on Board (COB) mini bars that could be connected to a delivery tube 802. The delivery tube may include a balloon 808 which may improve UV distribution and increase irradiance at the target tissue. The whole system could be connected to a flexible metal rod 804 which may be coupled to a power supply unit (not shown). The present example with one or more COB mini bars shows a UV irradiating area having a length of 10 cm. It will be appreciated that the length may be less than 10 cm or more than 10 cm depending on the application. In some example, one or more additional COB mini bars may be included in addition to mini bars 805 and 806 to cover a greater length of the delivery tube 802.

An example fiber optic solution with a COB light engine 902, that could be integrated with delivery tube to spread out the light therapy is shown at FIGS. 9A-9C. In this example, a single LED (904 in FIG. 9A) or multiple LEDs (FIGS. 9B and 9C) are connected (e.g., via coupling 906) to fiber optic cables 908 which transmit the light to the UV radiating area, and the fiber optics are constructed or treated so that they radiate light in that portion of the tube. Further, in some examples, as shown at FIG. 9C, collimating lens 914 may be utilized to focus and direct light through the fiber optic cables 908. As discussed above, the fiber optic cables 908 may be configured to emit light over a desired length of the delivery tube.

FIGS. 10A-10B illustrate an example of a flexible printed circuit board (PCB) 1004 with a heatsink (FIG. 10B) that includes LEDs 1010. In one example, the flexible PCB may be formed into a tube 1005 such that the LEDs 1010 are positioned around a circumference of the tube 1005. This embodiment is helpful for dissipating heat due to large surface area of the flexible PCB. Further, one or more air holes 1008 may be provided to enable improved cooling of the flexible PCB tube.

FIGS. 11A-11C illustrates various components of another embodiment of a delivery tube including a series of linear reflector and LEDs. As shown in FIG. 11B, the delivery tube includes a string of LED units aimed at reflectors nearby. Each LED unit includes an LED 1108, a reflector 1110, and a substrate 1114. An example distance between two LEDs 1108 may be 9 mm and a distance between LED 1108 and an end of the reflector 1110 receiving light from an LED may be 2 mm. For example, the distance between an LED and an end of the reflector may be sufficiently small so as to enable the reflector receive and spread the light out. In this way, greater light distribution is achieved while improving evenness of the delivery tube. FIG. 11B shows an example heat sink that may be implemented with the embodiment of FIG. 1*l* A. Further, an example beam angle of a narrow band (e.g. 343-345 nm) LED that may be utilized in the delivery tube shown at FIG. 11A may be 135 degrees.

The following set of experimental data is provided to better illustrate the claimed invention and is not intended to be interpreted as limiting the scope.

Example 1: *E. coli*

Figure 12A:
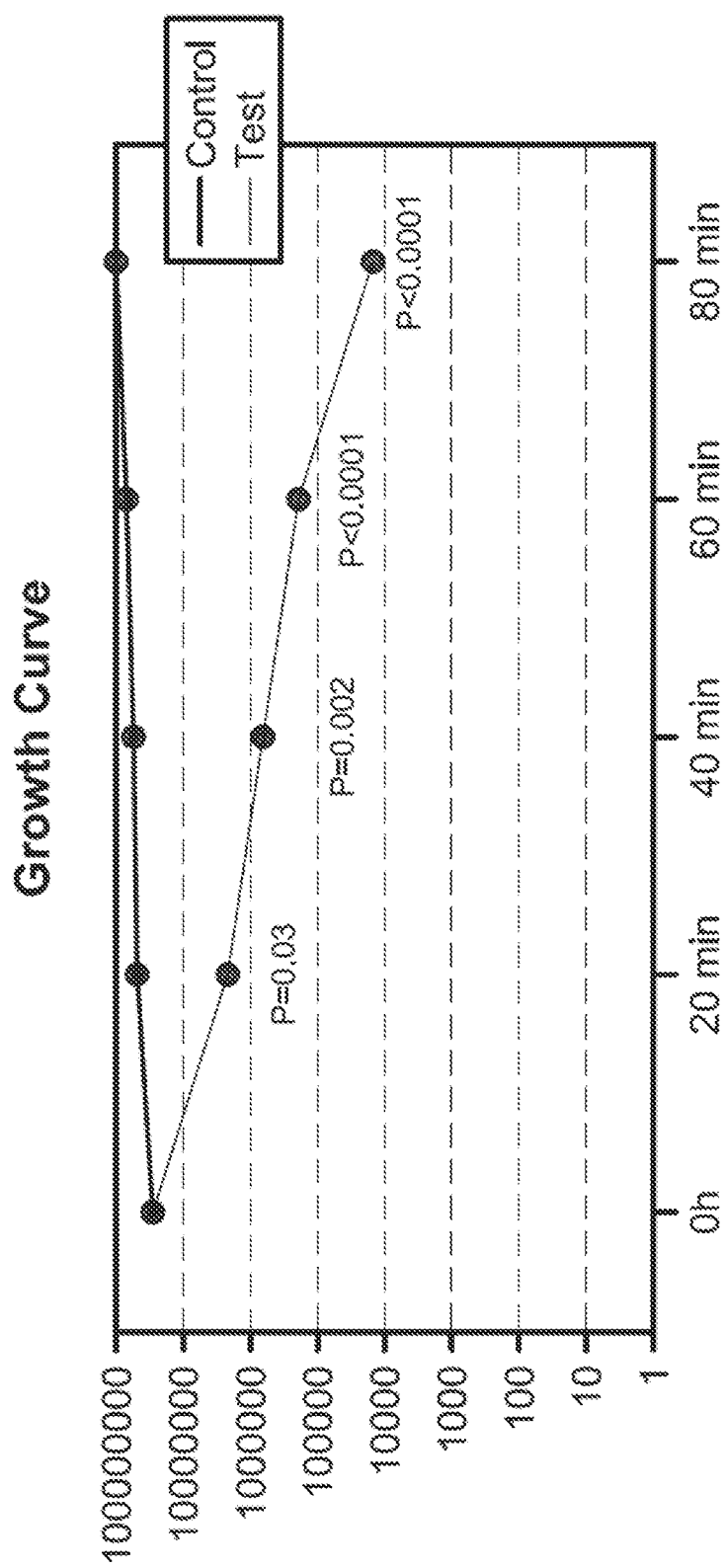
FIG. 12A shows a growth curve of *E. coli* when implementing an exemplary UV emitting device.
Figure 12B:
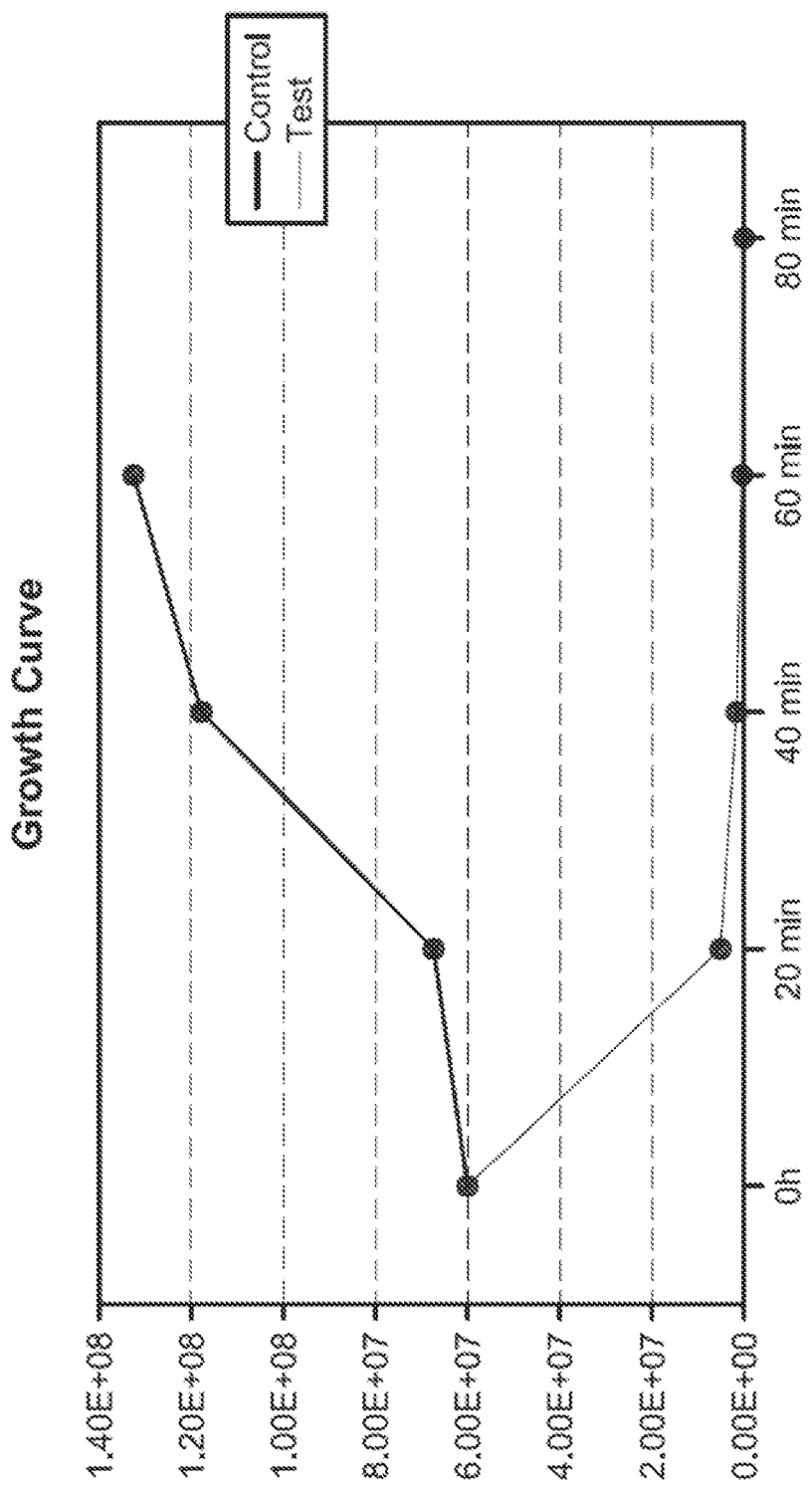
FIG. 12B shows a growth curve of *E. coli* when implementing an exemplary UV emitting device of the present disclosure.
Figure 13:
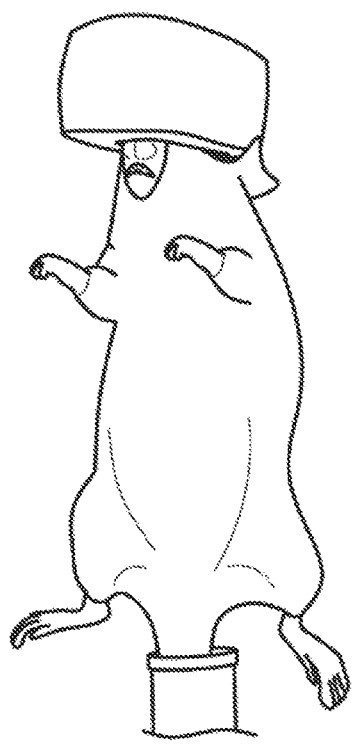
FIG. 13 shows a schematic of an exemplary UVA emitting device implemented in the colon of a mouse, in accordance with the principles of the present disclosure.
Figure 14B:
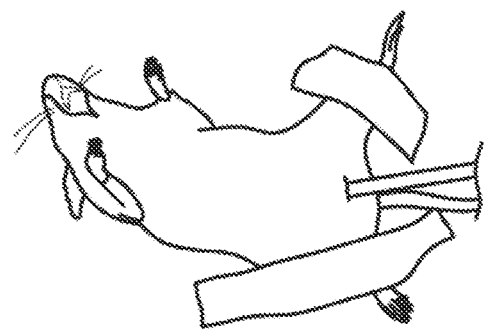
FIGS. 14A and 14B show schematic illustrations of an exemplary UVA emitting device of the present disclosure inserted into the vaginal canal of a rat, in accordance with the principles of the present disclosure.
Figure 14A:
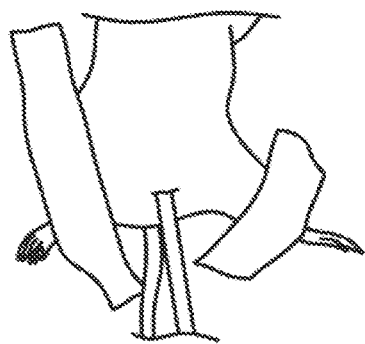

FIGS. 12A and 12B illustrate experimental data showing an example of a UV emitting device of the present disclosure being used to prevent *E. coli* from proliferating. As shown, the control group where the UV light was not applied continued to grow, whereas the test group that had UV light applied through the UV emitting device showed continuous decrease in *E. coli* count over time. The UV light is shown to both prevent *E. coli* from proliferating and also kill the bacteria over time.

Figure 15A:
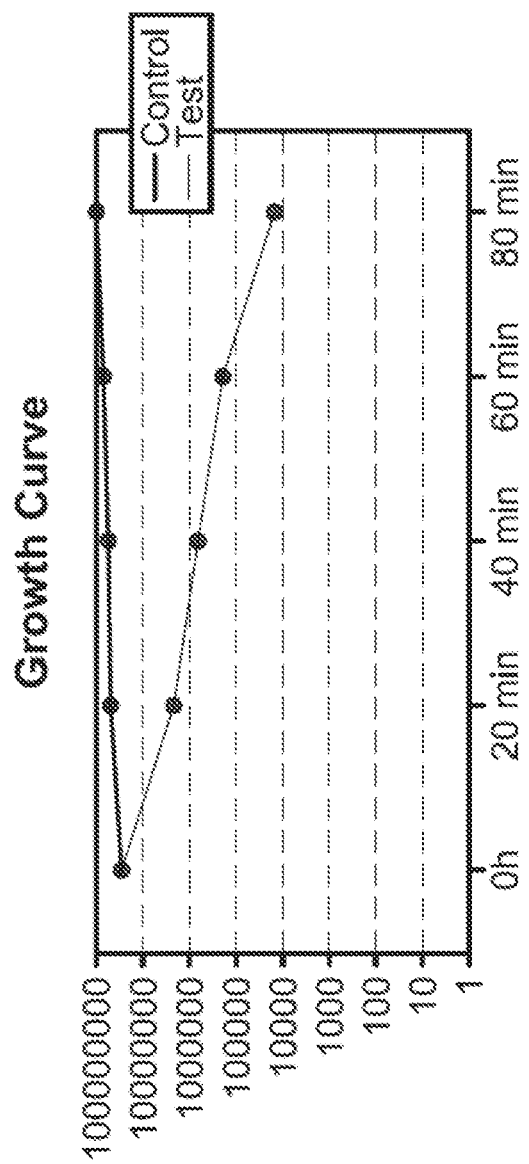
FIG. 15A shows a growth curve of liquid culture containing E. coli when implementing an exemplary narrow band UVA emitting device.
Figure 15B:
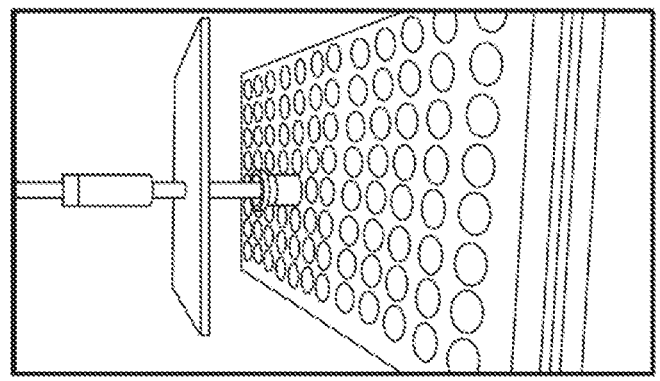
FIG. 15B shows an exemplary narrow band UV-A emitting device implemented on a liquid culture containing E. coli.
Figure 16:
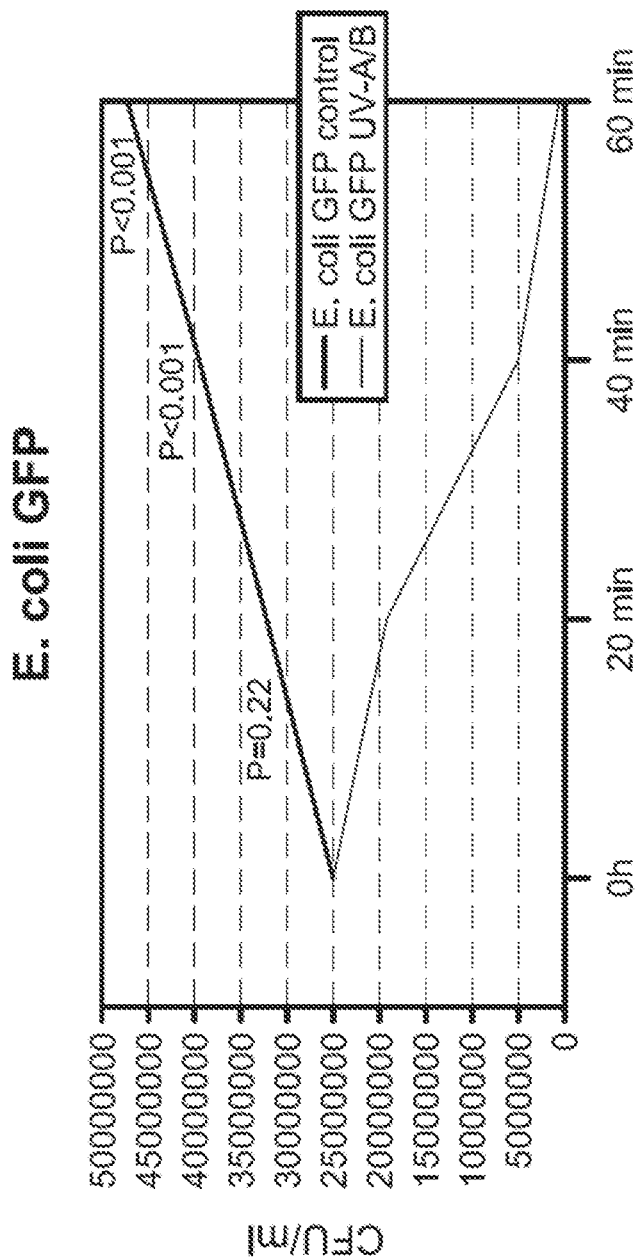
FIG. 16 shows a growth curve of liquid culture containing E. coli when implementing an exemplary narrow band UV-A emitting device.
Figure 18:
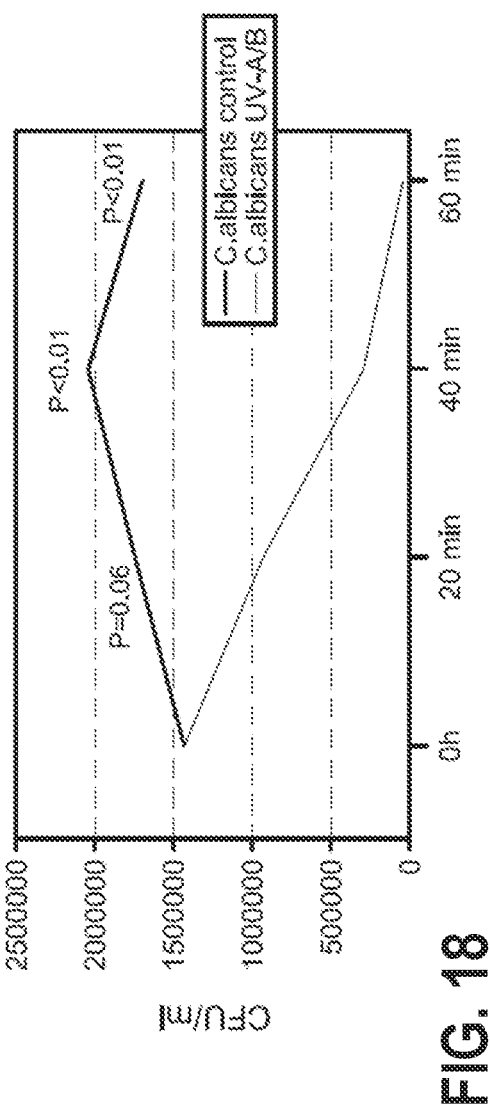
FIG. 18 shows a growth curve of liquid culture containing F. coli when implementing an exemplary UV emitting device.
Figure 19:
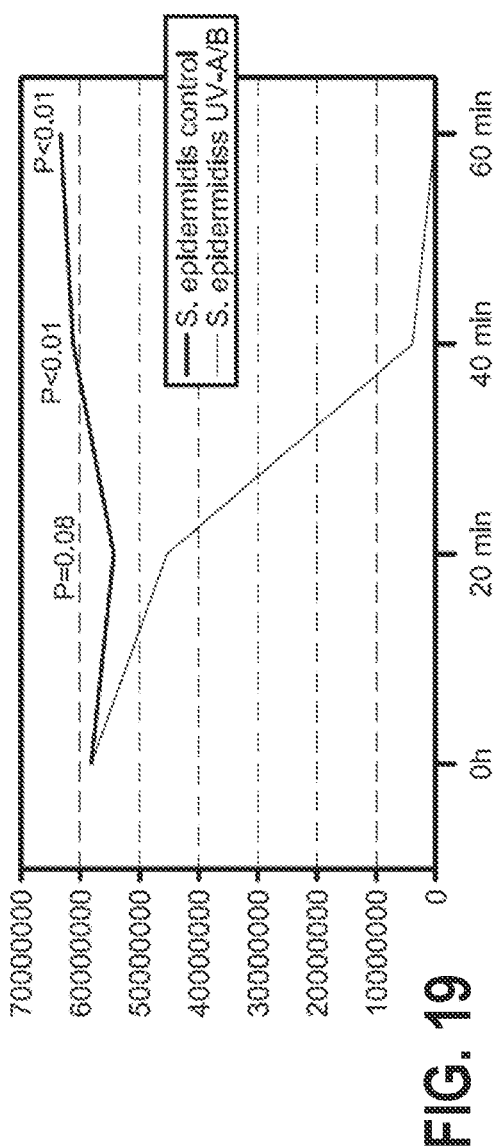
FIG. 19 shows a growth curve of liquid culture containing E. coli when implementing an exemplary UV emitting device.
Figure 20:
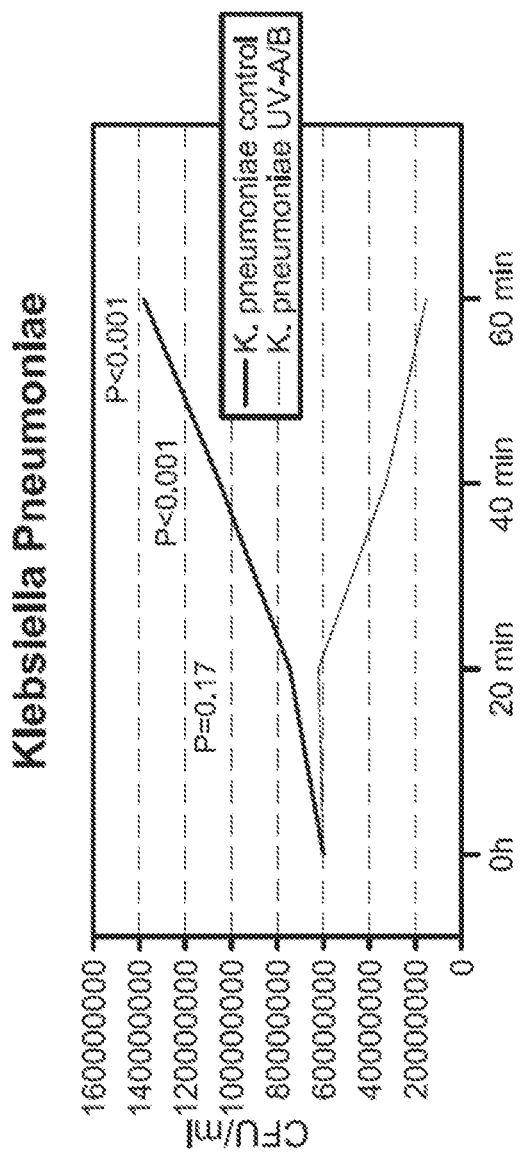
FIG. 20 shows a growth curve of liquid culture containing E. coli when implementing an exemplary UV emitting device.
Figure 21A:
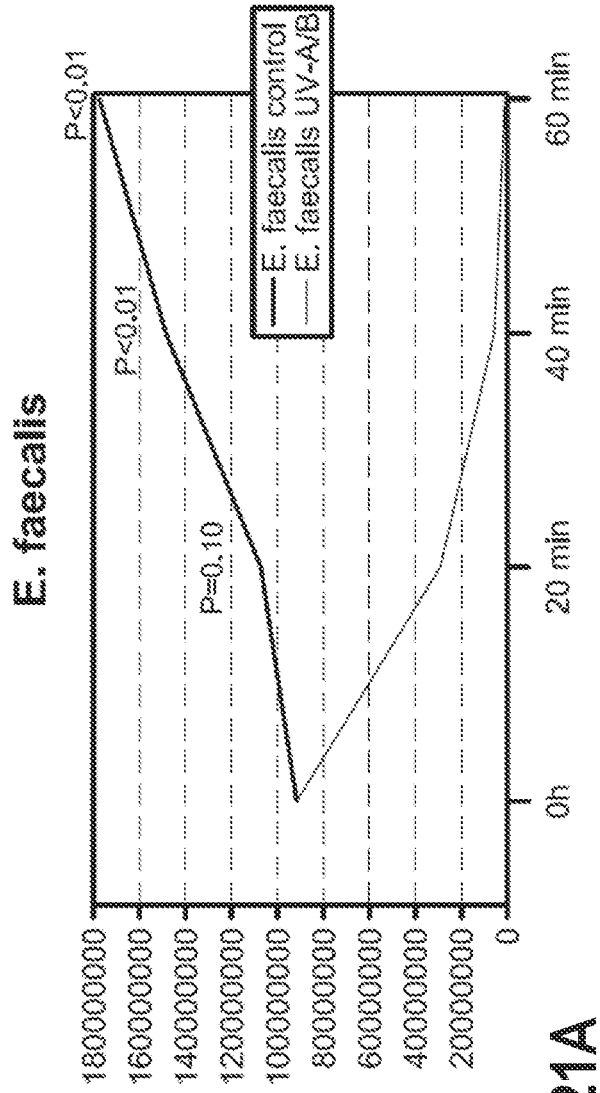
FIGS. 21A and 21B show growth curves of liquid culture containing E. coli when implementing an exemplary UV emitting device.
Figure 21B:
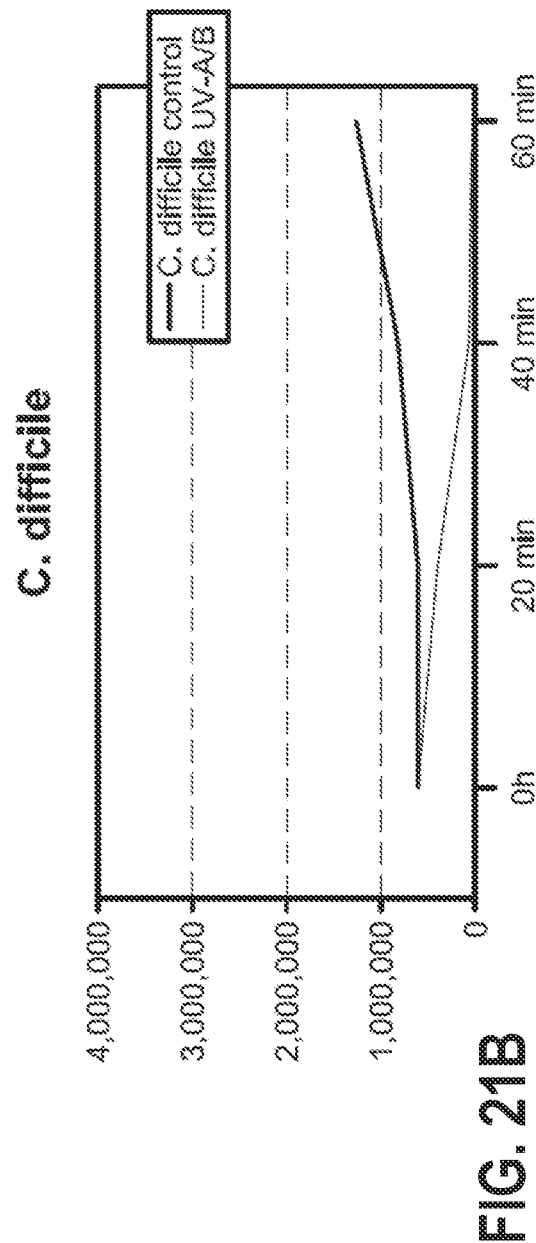

FIG. 15B illustrates an example of a UV emitting device of the present disclosure being used on a liquid culture containing *E. coli*. The results of this experiment and similar experiments with other bacteria and a fungus, *C. albicans* are shown in, e.g., FIGS. 15A, and 16, 17A-17B, 18-20, 21A, and 21B. All of the results illustrate a significant reduction in the growth of *E. coli* and other infectious agents in liquid samples where UV-A and UV-B lights were emitted by the UV emitting device of the present disclosure onto the liquid samples.

Example 2: Bacteria

In another example, two exemplary devices according to the present disclosure were used in UVA experiments to treat bacteria. The first device was a borosilicate rod (outer diameter 3 mm) repeatedly etched with a mixture of diluted sulfuric acid, sodium bifluoride, barium sulfate and ammonium bifluoride, with a reflective coating added to the end of the rod through which UVA was side-emitted. This process resulted in a side glowing rod of UVA (peak wavelength of 345 nm) as confirmed by spectrometer (Ocean Optics; Extech). The second device incorporated narrow band LEDs with a peak wavelength of (345 nm).

The UVA rod was inserted into liquid media. A mercury vapor lamp served as light source (Asahi Max 303, Asahi Spectra Co., Tokyo, Japan). The second UVA light-emitting device was a miniature light-emitting diode (LED) array (peak wavelength 345 nm) mounted on a heatsink (Seoul Viosys, Gyeonggi-Do, Korea). This device was used for the plated experiments noted below.

Stock cultures of *Escherichia coli*, *Escherichia coli* GFP, *Pseudomonas aeruginosa*, *Streptococcus pyogenes*, *Staphylococcus epidermis*, *Klebsiella pneumoniae*, *Enterococcus faecalis*, *Proteus mirabilis*, *Clostridioides difficile* and *Candida albicans* were grown in appropriate liquid culture media and conditions as illustrated in the table shown in FIG. 22. The American Type Culture Collection (ATCC) strains and one clinical isolate were grown in appropriate solid and liquid media following instructions suggested by the ATCC for each microorganism (Manassas, VA, USA). Using sterile techniques, the vial containing the microbial strain was opened and the entire pellet was rehydrated with approximately 500 μL of liquid broth.

Aseptically, the resuspended pellet was transferred to a tube containing 5-6 mL of the same liquid broth used to resuspend the cells. Several drops of the primary broth tube were used to inoculate a solid microbial agar and isolate single colony forming units (CFU). The liquid and solid cultures were incubated at specific temperatures, atmospheric conditions and times described in FIG. 22.

Initially, a liquid culture was prepared from a single CFU of each microbe to guarantee the purity of the strain during the UVA therapy. Only new pure liquid cultures were used during the experiments. One single colony was added to a 10 mL sterile tube containing 5 mL of liquid medium followed by thorough vortexing to homogenize the microbial cells. The liquid cultures shown in FIG. 22 were incubated until they reached the McFarland standard of 0.5. After meeting the standard turbidity, microbial cultures were mixed thoroughly for one minute and 1000 μL of the liquid culture were transferred into two 1.7 mL micro-centrifuge sterile tubes to be used as the treatment and control. An aliquot of 100 μL of each tube was serially diluted and plated on solid microbial medium to determine the number of CFU/mL at baseline as shown in FIG. 23.

Prior to UVA light therapy, several sterile 1.7 mL tube caps were prepared by creating a small hole through the top using a heated glass rod. The hole had the shape and size of the rod used to transmit UVA light.

Aseptically, the original caps from the liquid cultures in 1.7 mL tubes were replaced with the sterile caps with the hole. The UV light transmitter rod (sterilized with 70% ethanol) was placed into the hole created on the top of each cap. An identical rod was also placed into control-tubes. The light was transmitted through the glass rod inserted into the tube using the MAX-303 Xenon Light Source (Asahi Spectra USA, Inc., Torrance, CA). UV band width and irradiance peaks were assessed (Flame UV-VIS Fiber Optic Spectrometer, Ocean Optics). UV intensity was measured with SDL470 and UV510 UV light meters (Extech, NH, USA) Extech). Absence of UVC was confirmed using SDL470 UV light meter (Extech NH, USA). FIG. 22 describes the intensities and exposure durations of UVA light applied to the bacterial cultures.

After the end of the treatment time, the rods were removed from the treated and control tubes and a new sterile cap without a hole was used to close the liquid cultures. Both the treated and control groups were homogenized by vortexing. An aliquot of 100 μL of each tube was then serially diluted and plated on solid microbial medium to determine the number of CFU/mL after UVA treatment as shown in the table depicted in FIG. 23. This process was repeated until all time-points described in FIG. 23 were accomplished.

After each time point (baseline and post UVA treatment), 100 μL of the liquid microbial cultures (treated and controls) were serially diluted into sterile 1×PBS (EMD Millipore, Billerica, MA). The final serial dilution factors were 1:10 (100 μL of microbial culture and 900 μL of sterile 1×PBS), 1:100, 1:1000, 1:10,000 and 1:100,000. 100 μL of each dilution were plated in duplicates onto solid agar plates and incubated at time, temperature and atmospheric conditions described in FIG. 22. After incubation, the colonies were counted using a Scan 300 automatic colony counter (Interscience, Woburn, MA, USA), and the numbers of CFU/mL were defined after correcting for volume and the dilution factor.

The second device utilized in these experiments incorporated a miniature light-emitting diode (LED) array (peak wavelength 345 nm, bandwidth 10 nm) mounted on an aluminum heatsink (Seoul Viosys, Gyeonggi-Do, Korea). In the first experiment, this system was placed at 1 cm from the surface of a culture plate with a thick lawn of $E.$ $coli$ at approximately 2000 μW/cm$^2$ for 20 minutes. Subsequently, this light source was applied to liquid culture of 10$^2$ CFU/mL of $E.$ $coli$ and $P.$ $Aeruginosa$ in separate experiments.

For both conditions, UVA was tested in separate sets of experiments at intensities of 500, 1000, 2000 and 3000 μW/cm$^2$ for 20 and 40 minutes at 1 cm to produce a dose response curve. After incubation, the colonies were counted and colony sizes were measured using a Scan 300 automatic colony counter (Interscience), and the numbers of CFU/mL were defined after correcting for volume and the dilution factor.

Results

Exposure to UVA was associated with a significant reduction of various pathogenic microbes, including $Candida$ $albicans$ (P=0.007) and $Clostridium$ $difficile$ (P=0.01) as illustrated in the table depicted in FIG. 23. A UVA light exposure time of 20 min (intensity ranging 1300 to 3500 μW/cm$^2$) was the minimum effective duration to observe reductions for most microorganisms tested when compared to controls (P<0.05), except $Klebsiella$ $pneumoniae$ (P=0.17), $Enterococcus$ $faecalis$ (P=0.1), and $Streptococcus$ $pyogenes$ (P=0.64). The UVA light exposure times of 40 and 60 min were effective against all microorganisms tested when compared to untreated controls (P<0.05, FIG. 33). Notably, the bactericidal and fungicidal effects exhibited a dose-dependent response to UVA light, with greater microbial reductions associated with longer exposure times as illustrated in FIG. 23.

Figure 24:
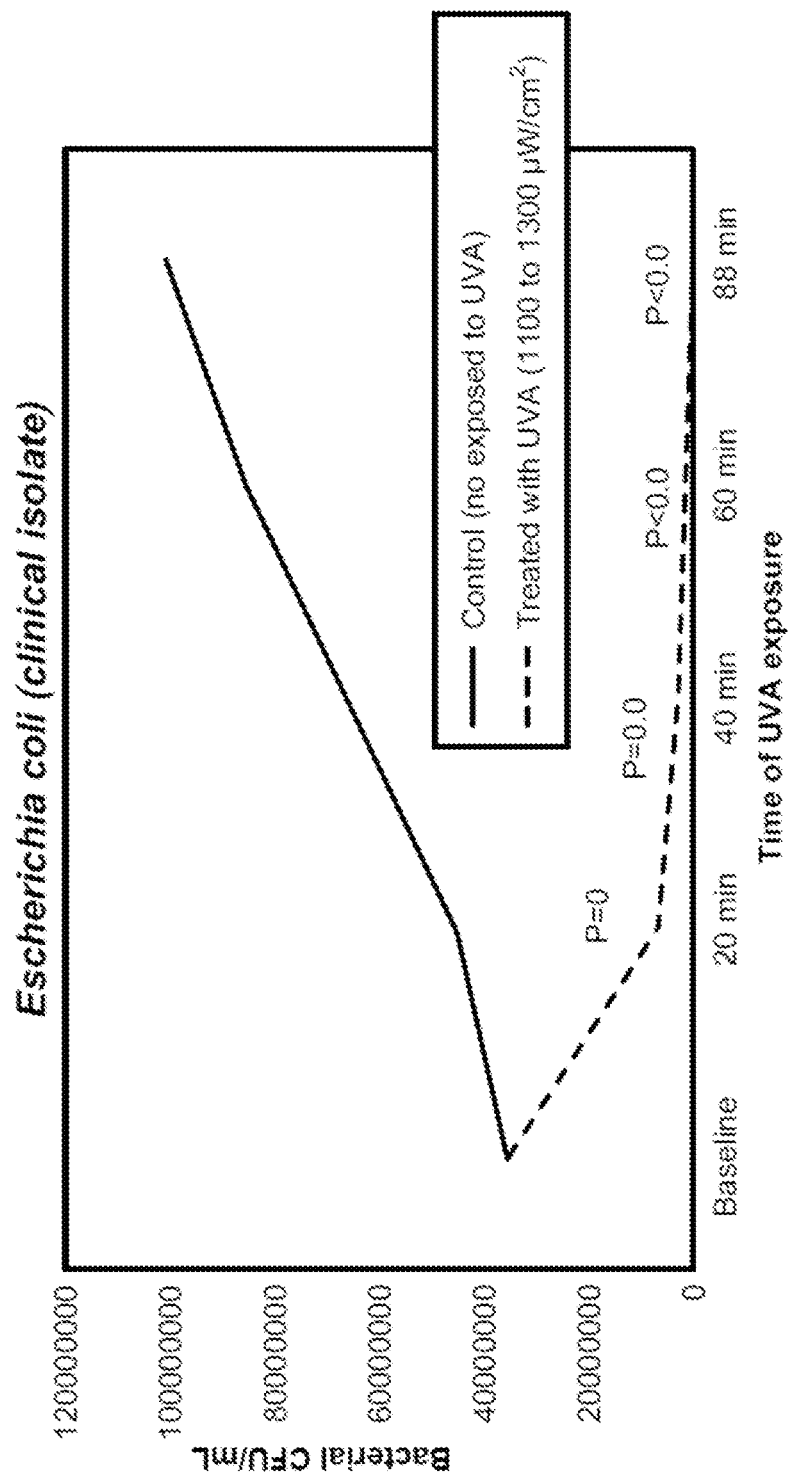
FIG. 24 shows a growth curve showing bacterial counts over time during narrow band UV-A light exposure using an exemplary system.

UVA light treatment was also applied to a clinically isolated $Escherichia$ $coli$ strain obtained from a human urinary tract. UVA light was tested in a set of five consecutive experiments, exposing this bacterial culture to 20, 40, 60 and 80 minutes of UVA, 1100 to 1300 μW/cm$^2$. Compared to baseline, the number of CFU/mL observed in bacterial cultures exposed to UVA light decreased at all-time points evaluated, including 20 min (P=0.03), 40 min (P=0.0002), 60 min (P<0.0001) and 80 min (P<0.0001) as shown in FIG. 24.

Figure 25A:
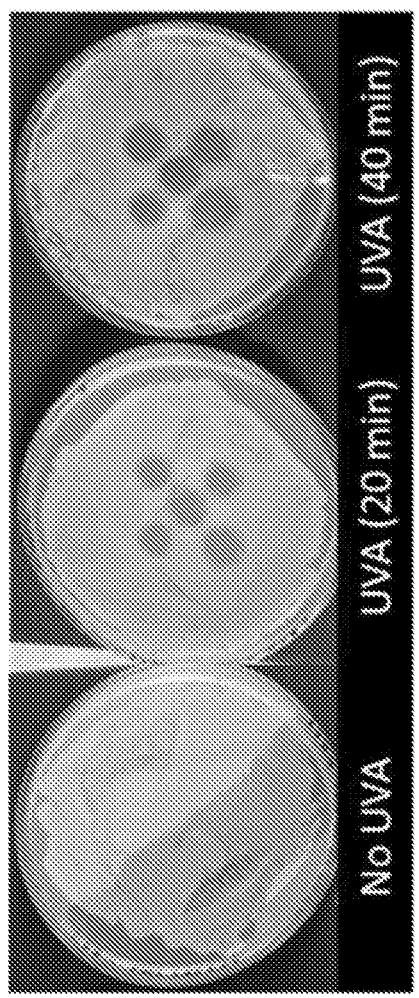
FIG. 25A shows images of petri dishes containing bacteria exposed to narrow band UV-A light over time compared to control.
Figure 25B:
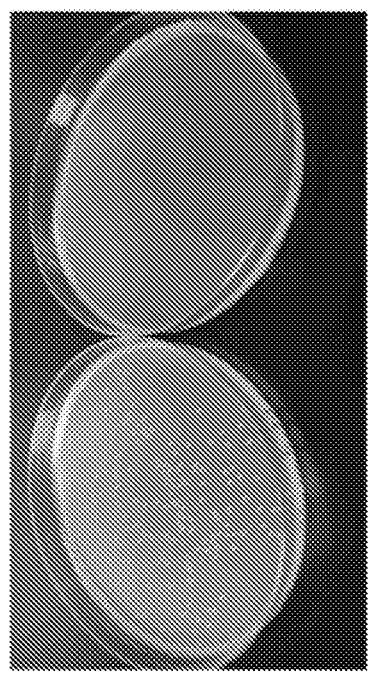
FIG. 25B shows images of petri dishes showing effects of narrow band UV-A treatment of E. coli liquid cultures when subsequently plated.
Figure 25E:
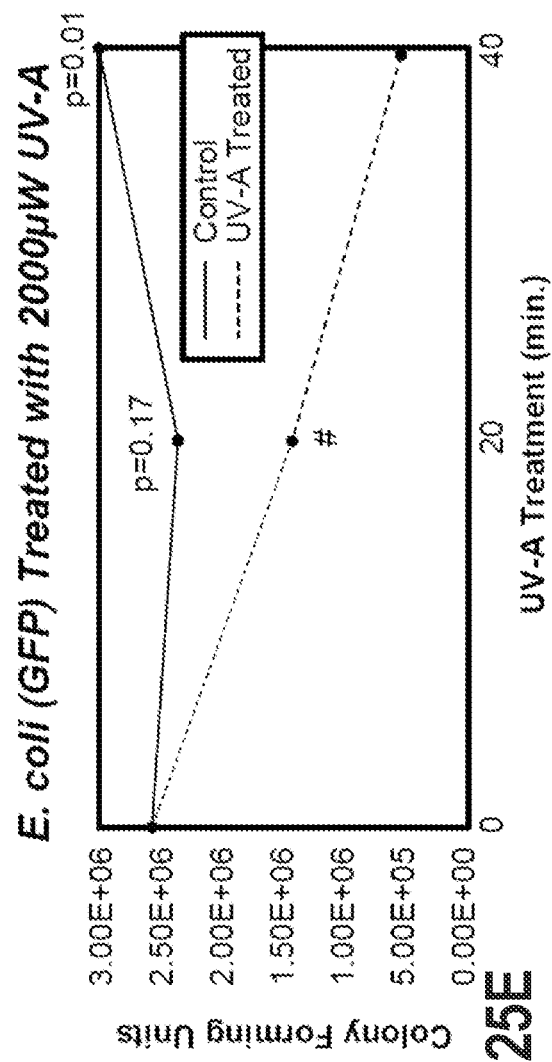

Finally, experiments were conducted to test the effects of LED narrowband UVA (345 nm peak wavelength) on $E.$ $coli$ and $Pseudomonas$ $aeruginosa$. In these experiments, this specific wavelength of UVA resulted in a significant reduction in bacterial cells as shown in FIGS. 25A-25N. For instance, FIG. 25A illustrates a picture of a bacterial colonies in petri dishes, and the pattern of disappearance of the colony around the site of application of the LED light at 20 and 40 minutes. FIG. 25B shows effects of UVA treatment of $E.$ $coli$ liquid cultures when subsequently plated. Liquid $E.$ $coli$ cultures were treated with 3000 W/cm2 for 20 minutes (right) or left untreated as controls (left), then plated on solid medium. There is a notable decrease in the number and size of $E.$ $coli$ colonies following UVA treatment (right plate).

Figure 25F:
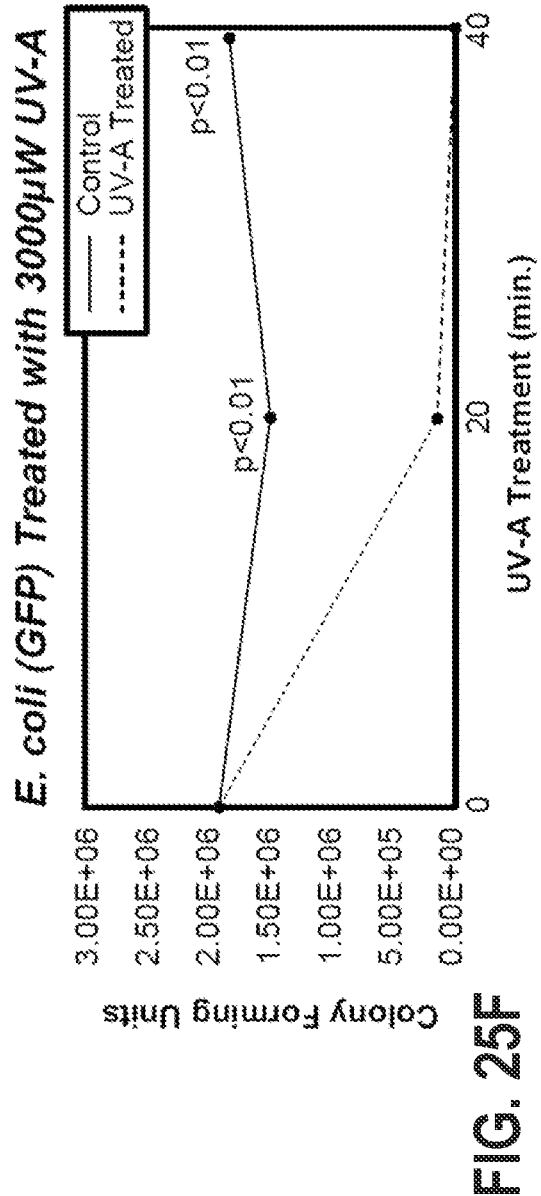
Figure 25G:
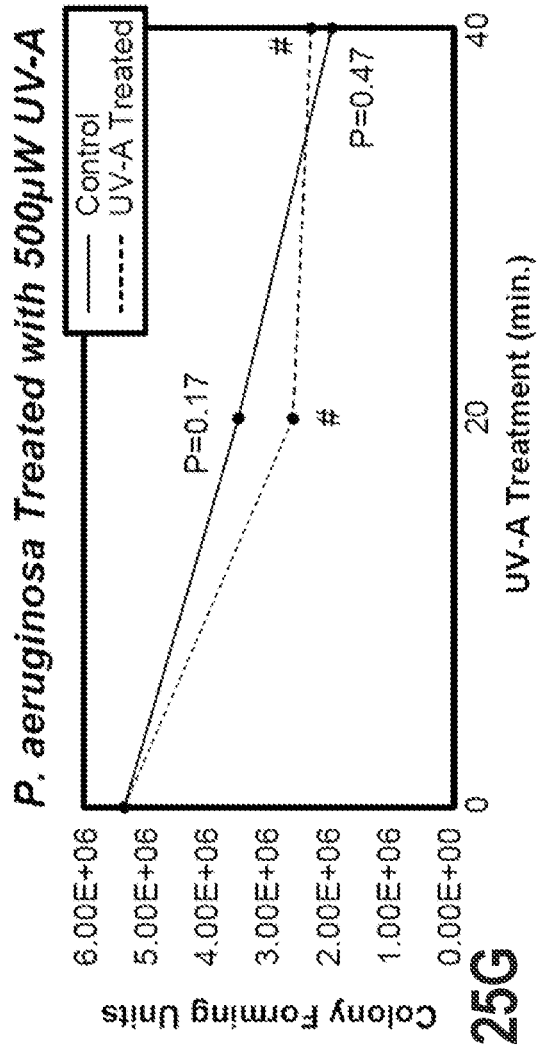
FIGS. 25G-25J show growth curves showing P. aerugiosa bacterial counts over time exposed to various intensities of UV light using exemplary systems.
Figure 25H:
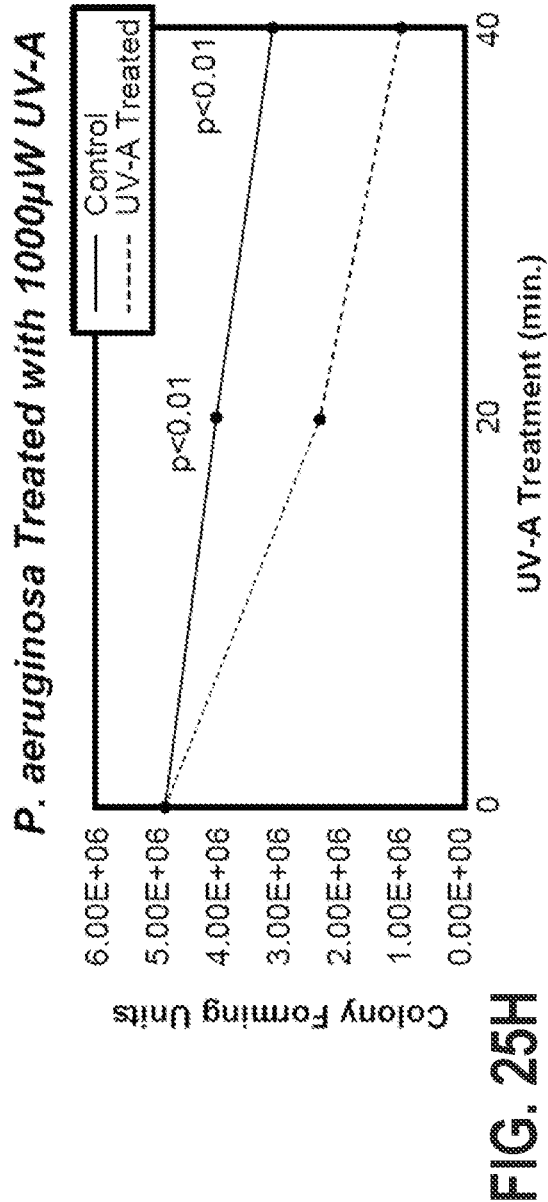

FIGS. 25C-25F illustrate graphs showing the change in colony forming units (CFUs) of $E.$ $coli$ over time when UV-A light with a peak wavelength of 345 nm is applied at various intensities. As illustrated most of the bacteria were eliminated by 40 minutes with an intensity of 2000 uW (FIG. 25E) and most of the bacteria were eliminated by 20 minutes with an intensity of 3000 uW (FIG. 25F). When the same light was applied at 500 uW and 1000 uW of intensity, there was significant reduction of CFUs by 40 minutes, but only by about half (FIG. 25C and FIG. 25D).

Figure 25I:
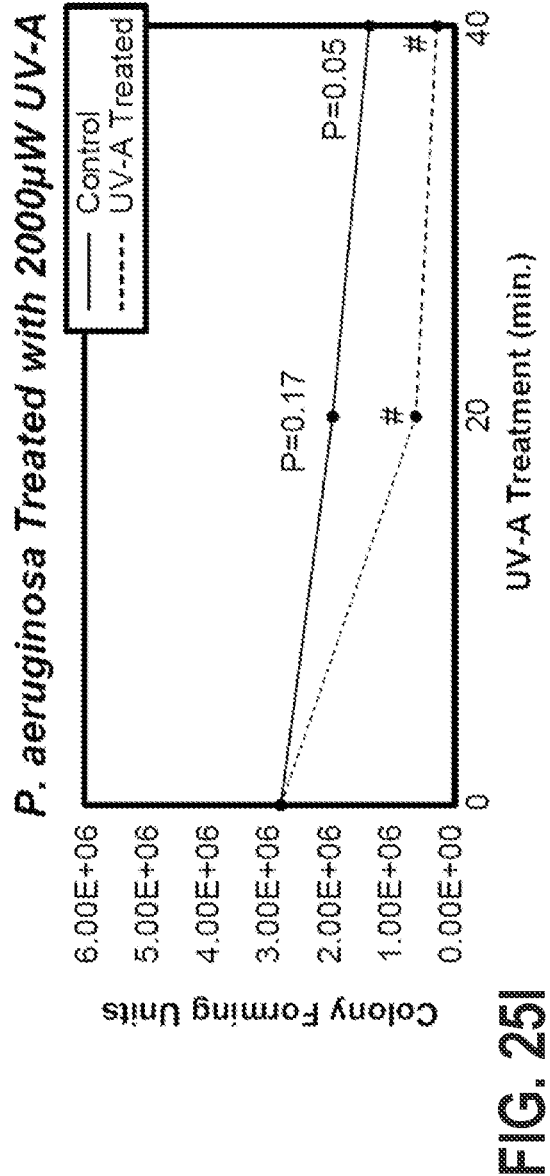
Figure 25J:
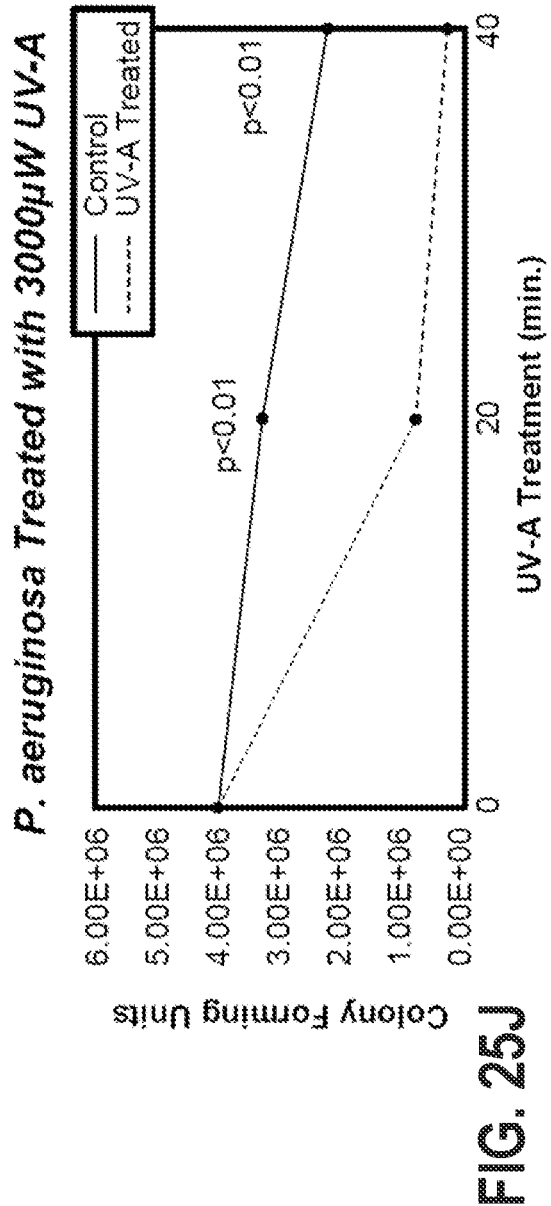

FIGS. 25G-25J illustrate graphs showing the change in colony forming units (CFUs) of $P.$ $aeruginosa$ over time when UV-A light with a peak wavelength of 345 nm is applied at various intensities. As illustrated, treatment with an intensity of 1000 uW, 2000 uW and 3000 uW showed significantly greater reduction in CFUs compared to control (FIG. 25H, FIG. 25I and FIG. 25J), and most of the bacteria were eliminated by 20 minutes with an intensity of 2000 uW and 3000 uW (FIG. 25I and FIG. 25J).

Figure 25K:
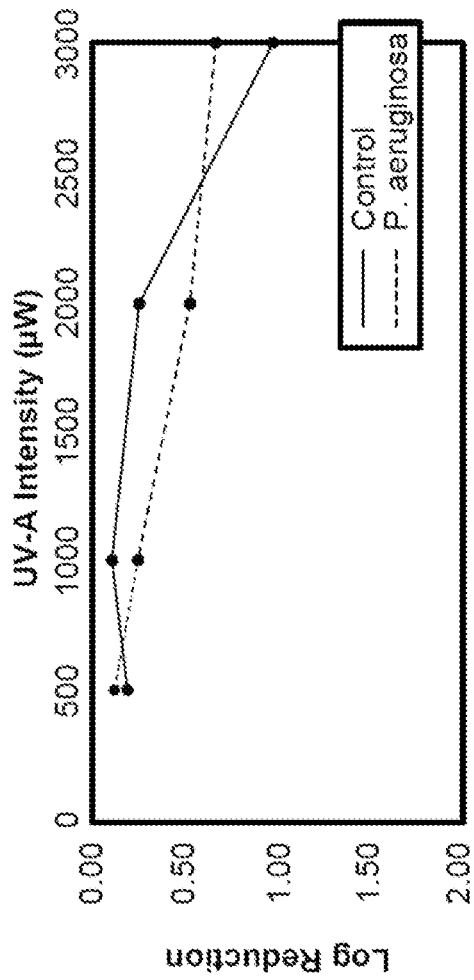
FIGS. 25K-25L show growth curves comparing the logarithmic reduction at various intensities at 20 minutes and 40 minutes respectively using exemplary systems.
Figure 25L:
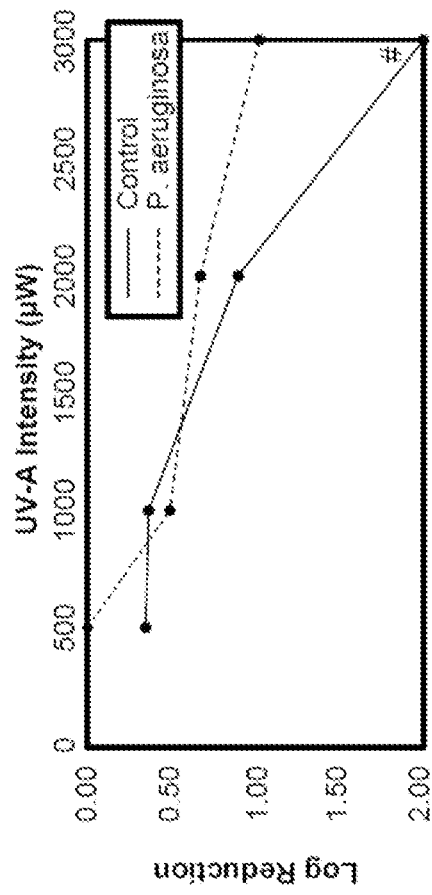
Figure 25M:
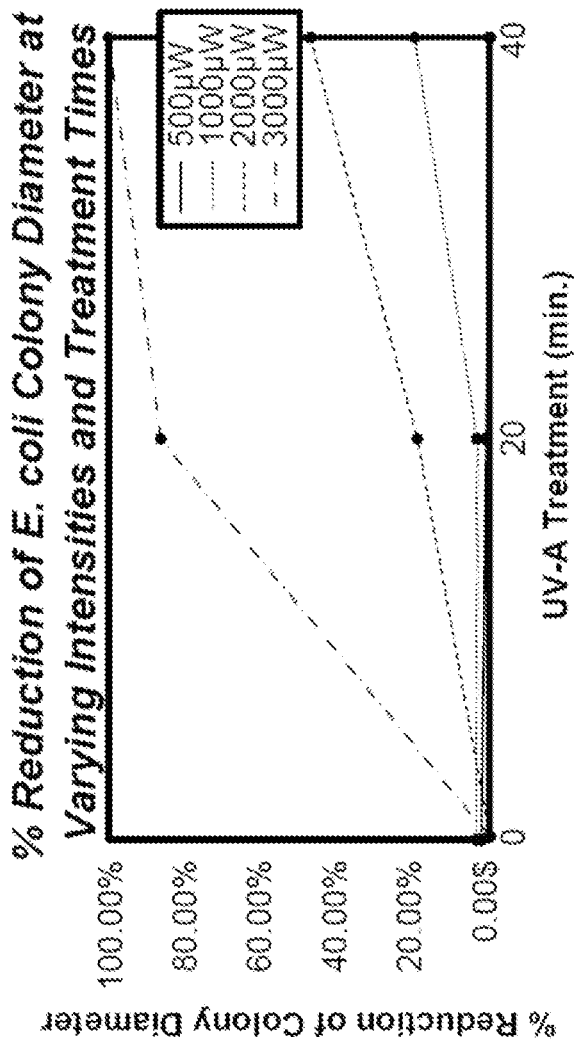
FIG. 25M shows growth curves showing the reduction of E. coli colony diameter at various intensities and treatment times using an exemplary system.
Figure 25N:
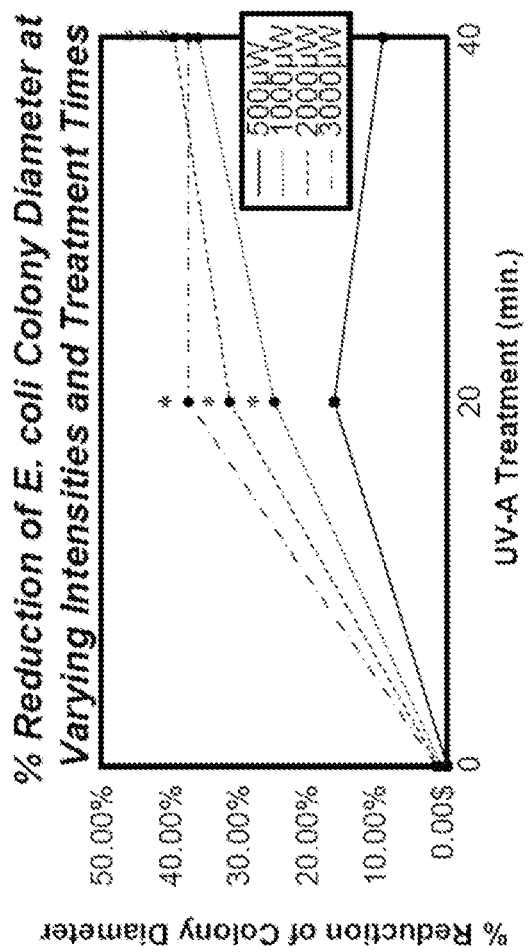
FIG. 25N shows growth curves showing the reduction of a P. aeruginosa colony diameter at various intensities and treatment times using an exemplary system.

FIGS. 25K-25L illustrate growth curves comparing the logarithmic reduction of $P.$ $aeruginosa$ at various intensities at 20 minutes and 40 minutes respectively. FIG. 25M illustrates growth curves showing the reduction of a $E.$ $coli$ colony diameter at various intensities and treatment times. FIG. 25N illustrates growth curves showing the reduction of a $P.$ $aeruginosa$ colony diameter at various intensities and treatment times.

Examining the effect of light intensity on the reduction of *E. coli* and *P. aeruginosa*, there was a dose response effect on both bacterial levels and colony size (FIGS. 25B-25N). The ideal UVA intensity to impact bacteria appeared to be between 2000 and 3000ρW/cm2 when using a narrowband LED with a peak wavelength of 345 nm, and in some examples may depend on the bacteria or pathogen type and species, and other factors as disclosed herein.

Example 3: Safety Data

For the assessment of the safety of UVA on mammalian cells, three experiments were conducted. The first was the exposure of UVA to HeLa cells in culture. HeLa cells were added to DMEM cell culture medium (Gibco, Waltham, MA) plus 10% Bovine serum (Omega Scientific, Tarzana, CA) and 1× Antibiotic-Antimycotic (100× Gibco) in 60×15 mm cell culture dishes (Falcon) and incubated at 37° C. (5% $CO_2$) for 24 hours to achieve 1,000,000 to 1,800,000 cells per plate. At this point cells were exposed to UVA LED light (1800 µW/cm$^2$) for 0 (control), 10, or 20 minutes. After 24 hours, cells were removed by 0.05% Trypsin-EDTA (1×) (Gibco), stained with Trypan blue (Trypan Blue 0.4% ready to use (1:1) (Gibco)) and quantitated by automated cell counter (Biorad T20, Hercules, CA). In a similar experiment, the LED UVA light was used at a higher intensity (5000 µW/cm$^2$) for 20 minutes. Once again, HeLa cells were quantitated at 24 hours following UVA exposure.

The safety of UVA was also studied in two human respiratory cell types. These included alveolar (ATCC A549) and primary ciliated tracheal epithelial cells (HTEpC) (PromoCell, Heidelberg, Germany). For each cell line, 250,000 cells were plated and grown for 48 hours in DMEM until the cell count per plate was approximately 750,000. At this point, cells were exposed to UVA (2000 µW/cm$^2$) for 0 (control) or 20 minutes (treated), and cell counts were obtained at 24 hours later.

The levels of 8-hydroxy-2'-deoxyguanosineis (8-OHdG) was also analyzed in the DNA of cells treated with UVA. 8-OHdG is widely accepted as a sensitive marker of oxidative DNA damage and oxidative stress. DNA was extracted with the AllPrep DNA/RNA/Protein Mini Kit (Qiagen) following manufacturer's instructions. The levels of 8-OHdG was detected using the EpiQuik™ 8-OHdG DNA Damage Quantification Direct Kit following manufacturer's instructions (Epigentek, Farmingdale, NY). For optimal quantification, the input DNA amount was 300 ng, as the basal 8-OHdG is generally less than 0.01% of total DNA (Epigentek, Farmingdale, NY).

Wild type 129S6/SvEv mice (n=20, female=10) and BALB/cJ mice (n=10,female=5) were used for UVA light safety tests. All animals were anesthetized prior the procedure. Prior to the UVA light treatment, animals were placed in an induction chamber containing isoflurane anesthetic gas (1-5%). The carrier gas for isoflurane was compressed oxygen (100% oxygen). Once the respiratory rate had slowed (approximately one breath per second), the animals were removed from the induction chamber and maintained under sedation using a nose cone anesthesia (1-2% isoflurane). The depth of anesthesia was confirmed by lack of response to toe pinch.

Under anesthesia, customized rods (D=4 mm, L=40 mm) were introduced anally up to the splenic flexure. The same procedure was applied to the control group using an identical but unlit rod. Same light source and measurement equipment were used as described for liquid culture experiments.

In the first experiment, 5 BALB/cJ mice underwent colonic UVA exposure (2,000 µW/cm$^2$) for 30 minutes as compared to 5 mice treated with the same technique with an unlit optic rod.

In the second experiment, 10 129S6/SvEv mice underwent 20 minutes per day of colonic UVA exposure (3,000-3,500 µW/cm$^2$) for 2 two consecutive days as compared to 10 mice (male=5) treated with an unlit rod.

Colon Endoscopic Examination Before and After UVA Light Therapy

A rigid pediatric cystoscope (Olympus A37027A) was used to assess the intestinal mucosa before and after 7 days of UVA exposure. Endoscopy was performed in anesthetized animals. The method of sedation is described above.

The anus was first lubricated with a water-based gel (Astroglide®, BioFilm, Inc., Vista, CA, USA). The endoscope was then inserted to the splenic flexure, and the colon was insufflated using room air instilled via an endoscopic port. All endoscopies were recorded and blindly interpreted by two gastroenterologists with expertise in animal model endoscopies. Endoscopic appearances were analyzed based on perianal examination, transparency of the intestinal wall, mucosal bleeding, and focal lesions.

At day 14, control and treated mice were euthanized, and swiss-roll preparations of the entire colon were performed as suggested by Bialkowska et al. Briefly, the entire colon was removed and rinsed in a modified Bouin's fixative solution (50% ethanol/5% acetic acid in dH2O). Using scissors, the colon was opened longitudinally along the mesenteric line and rinsed briefly in a Petri dish containing 1×PBS. The luminal side was identified and Swiss rolling of the opened tissue was performed. Once the entire colon length was rolled, the colon was carefully transferred to a tissue-processing/-embedding cassette. The cassette was placed in 10% buffered formalin overnight at room temperature, after which paraffin sections of the colon were cut, stained with hematoxylin and eosin (H&E), and assessed by a blinded pathologist (SS).

Data for bacterial counts between groups were not normally distributed and were therefore compared using non-parametric tests (Mann Whitney U test). Other quantitative data were compared by t-test using GraphPad Prism 7 (GraphPad, San Diego, CA).

Results

Figures 26A, 26B:
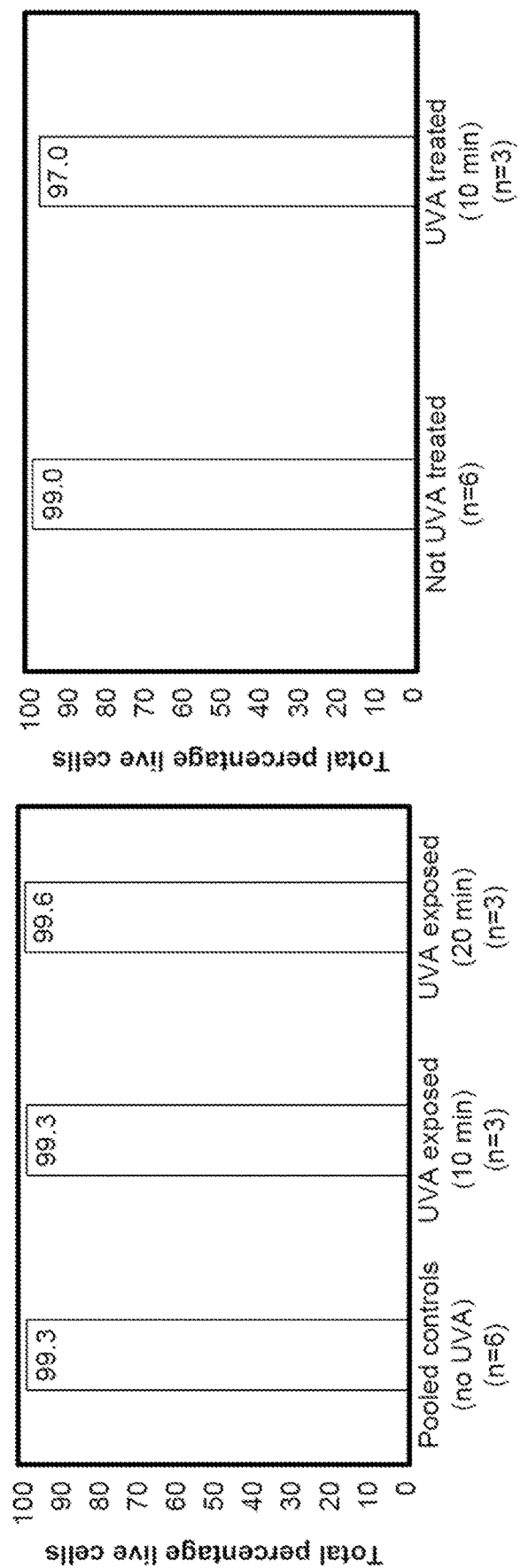
FIG. 26A shows a bar graph showing cell growth during exposure to UV-A light using an exemplary system.
FIG. 26B shows a bar graph showing cell growth during exposure to UV-A light using an exemplary system.

Overall, based on cell growth over time, LED UVA appeared safe in the mammalian cells tested (HeLa, alveolar A549 and primary tracheal cells). All plates demonstrated continued cell growth, regardless of UVA exposure, with 1.5 to 2 times the number of cells per plate compared to controls, indicating robust ongoing replication. In the case of HeLa cells, UVA did not affect the number of live cells at 24 hours when compared to unexposed controls (P=0.99 and P=0.55 for 10 min and 20 min of ~2000 µW/cm$^2$ UVA, respectively) as shown in FIG. 26A. Higher intensity UVA (5000 µW/cm$^2$) did not affect the growth of HeLa cells as shown in the bar graph depicted in FIG. 26B. Similar findings were also seen with alveolar cells at 2000 µW/cm$^2$ for 20 min (P=0.99) as shown in FIG. 26C. Finally, ciliated epithelial cell growth was also unaffected by UVA after 20 minutes of exposure to ~1000 µW/cm$^2$ and to ~2000 µW/cm$^2$.

Figure 26D:
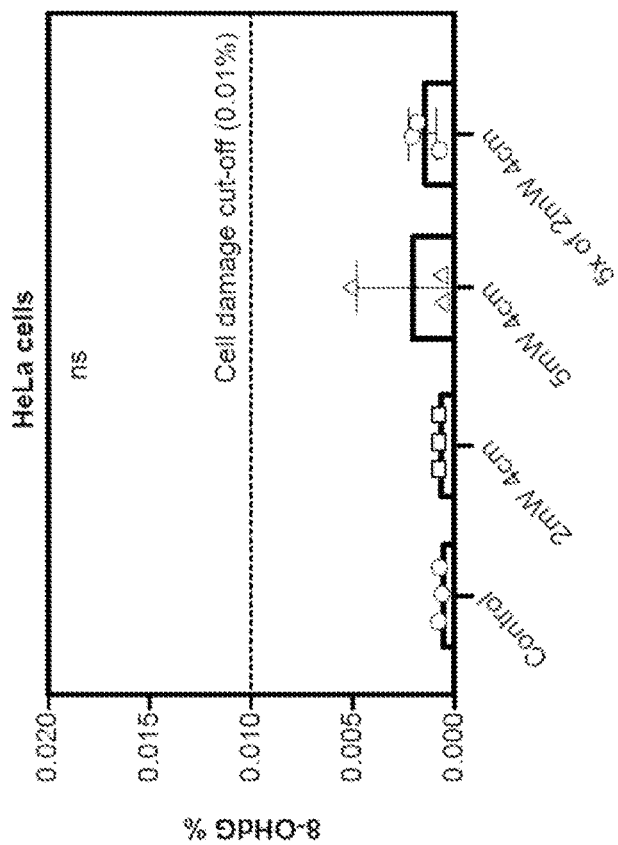
FIG. 26D shows a bar graph showing the absence of DNA damage to cells during exposure to UV-A light using an exemplary system.
Figure 26C:
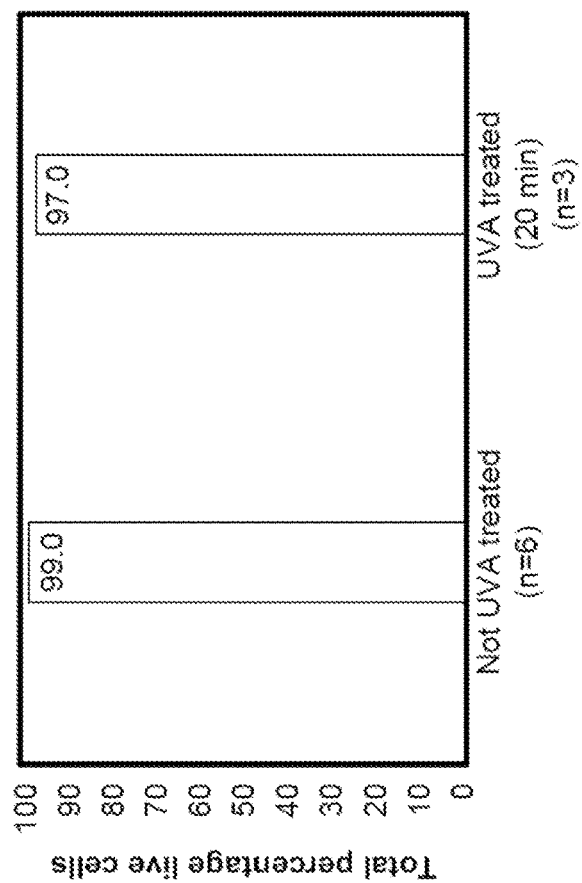
FIG. 26C shows a bar graph showing cell growth during exposure to UV-A light using an exemplary system.
Figure 26F:
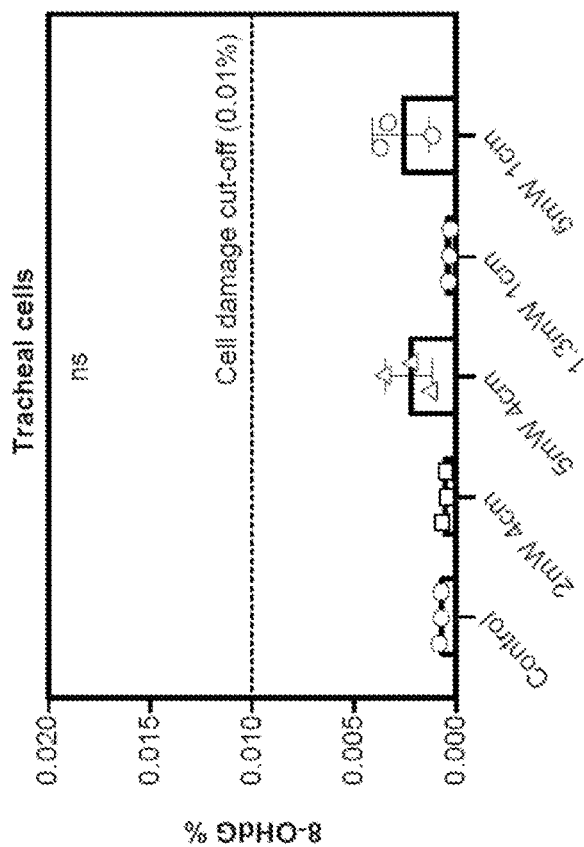
FIG. 26F shows a bar graph showing lack of DNA damage to cells during exposure to UV-A light using an exemplary system.
Figure 26E:
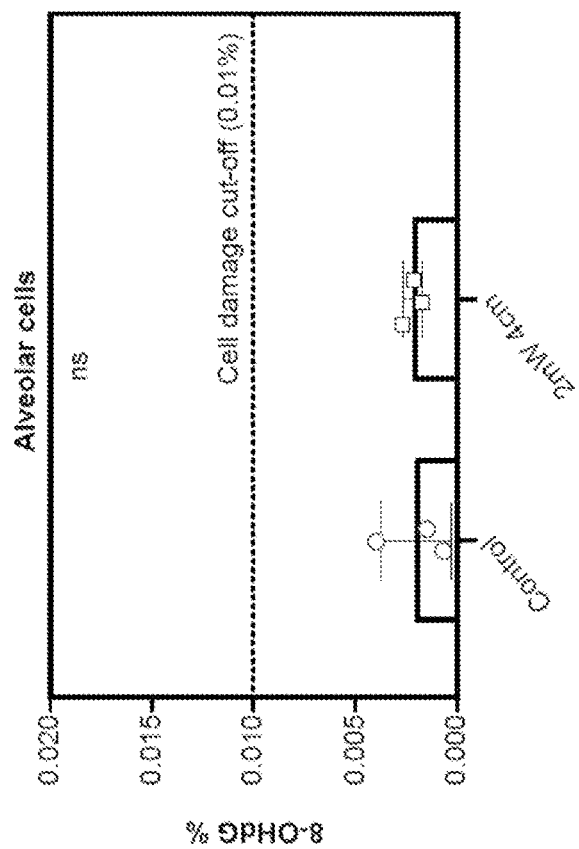
FIG. 26E shows a bar graph showing lack of DNA damage to cells during exposure to UV-A light using an exemplary system.

Moreover, exposure to UVA did not cause DNA damage in any cell line analyzed, and the levels of 8-Oxo-2'-deoxyguanosine (8-OHdG) in cells treated with narrow-band LED UVA was similar to controls not exposed to UVA (P<0.05) as shown in FIG. 26D (HeLa cells), FIG. 26E (Alveolar cells), and FIG. 26F (Tracheal cells). Higher intensity LED UVA (5000 µW/cm$^2$) appeared to increase the levels of 8-OHdG (P=0.07) but the percentage of 8-OHdG remained well below the generally accepted threshold of 0.01% of the total DNA.

UVA light exposure is not associated with endoscopic or histologic injury

To assess the safety of UVA therapy on internal visceral cells and tissues, two different wild-type strains of mice were exposed to intracolonic wide-spectrum UVA light using optical rods designed to homogenously side-emit broad-spectrum UVA. Only the left side of the colon up to the splenic flexure were exposed to UVA light; hence, the unexposed right side served as a self-control. In the first experiment, under anesthesia, 5 mice underwent colonic UVA exposure (2,000 µW/cm2) for 30 minutes as compared to 5 mice treated with the same technique with an unlit optic rod.

In the second experiment, 10 mice (129S6/SvEv, male=5) underwent 20 minutes per day of colonic wide spectrum UVA exposure (3,000-3,500 $\mu W/cm^2$) for 2 two consecutive days as compared to 10 mice (male=5) treated with an unlit rod. No perforation, bleeding or fatalities were seen in any of the experiments. The mouse colonoscopy images show no change before and after UVA exposure.

In both experiments, endoscopic evaluation of mice before and after UVA administration demonstrated no macroscopic evidence of mucosal erythema, friability, ulceration or bleeding. Assessed by a blinded pathologist (SS), no chronic/acute inflammation, cystitis, crypt abscesses, granulomata, ulceration or dysplasia was seen on examined full-thickness colonic specimens exposed to wide spectrum UVA as compared controls and untreated segments of the colon.

RNA Virus Experimental Data

Additionally, the disclosed systems and methods were utilized to obtain experimental data in treating various RNA viruses with UVA light. Accordingly, the data illustrates that UV-A light emitted from an LED with a peak wavelength of 340 nm, can kill RNA viruses like Coxsackievirus. For instance, the Hela cells infected with Coxsackievirus survived when this UV-A treatment was applied, but did not survive when there was no UV-A light treatment applied after infection. Furthermore, the experimental data demonstrated only a 15% loss of UV-A light once it passed through an ET Tube.

In late December 2019, an outbreak of a novel coronavirus disease (SARS-CoV-2 or COVID-19; previously known as 2019-nCoV) was reported in Wuhan, China. COVID-19 is a viral infection that replicates efficiently in the upper respiratory tract. As part of the mechanism of action, the virus infects ciliated tracheal epithelial cells, which then slough off and compromise alveolar function. Secondary bacterial infections have also been noted, and both of these processes can lead to further inflammation, acute respiratory distress syndrome (ARDS), and ultimately, death. It is estimated that 10-15% of those infected have a severe clinical course and about 5% become critically ill, requiring mechanical ventilation for failure of the respiratory and other organ system. The case fatality rate of COVID-19 has been estimated to range from 0.5% to 9.5%, although these estimates are confounded by preferential testing of symptomatic patients and a lag time of up to 14 days for symptom presentation. Death is thought to be due to respiratory failure in the setting of ARDS and/or secondary infections including ventilator associated pneumonia (VAP).

Ventilator-associated pneumonia (VAP) may develop in intensive care unit (ICU) patients who are mechanically ventilated for at least 48 hours, which is common in COVID-19 patient. The incidence of VAP ranges broadly from 5% to 67%, depending on the diagnostic criteria used and patient population studied. Causative organisms include Enterobacteriaceae (25%), *Staphylococcus aureus* (20%), *Pseudomonas aeruginosa* (20%), *Haemophilus* influenza (10%), and streptococci (13). Multi-drug resistant bacteria are more common among late-onset cases. Mortality attributed to early-onset VAP is thought to be approximately 6% while that for late-onset VAP is 10%.

Currently, there is no treatment for COVID-19 and conventional means to reduce secondary infections in mechanically ventilated patients have proven insufficient to date. A safe and effective broad antiviral and antibacterial approach to these patients would potentially reduce viral burden, secondary infection and VAP, time on mechanical ventilation, and death due to respiratory failure.

As disclosed herein, ultraviolet (UV) light has antibacterial properties. UVC (110-280 nm) is widely used for industrial sterilization (16), but has harmful effects on human DNA. External UVA (320-400 nm) and UVB (280-320 nm) devices have FDA-approved indications to treat human diseases such as psoriasis, eczema, and skin lymphoma. These wavelengths penetrate the mucosal and submucosal tissue. Of the three spectrums, UVA appears to cause the least damage to mammalian cells. Presently, there are no studies showing the effects of an internal application of UVA light for bacterial or viral infections. Advances in light emitting diodes (LEDs) are making it feasible to apply narrow-band UVA to internal organs.

Accordingly, disclosed is experimental data illustrating the effects of broad and/or narrow band UVA for the treatment of common bacterial pathogens known to be associated with VAP. Additionally, disclosed is data that demonstrates on the effects of a specific wavelength of UVA on group B coxsackievirus and coronavirus 229E. Finally, further data demonstrates the safety of UVA exposure for mammalian cells and in vivo epithelial cells.

Example 4: Coxsackievirus

Coxsackievirus Sample Obtainment and Infection into Cells

Recombinant coxsackievirus B (pMKS1) expressing enhanced green fluorescent protein (EGFP-CVB) plasmid was linearized using ClaI restriction enzyme (ER0142, Thermo Fisher) and linearized plasmid was purified using standard phenol/chloroform extraction and ethanol precipitation. Viral RNA was then produced using mMessage mMachine T7 Transcription kit (AM1344, Thermo Fisher). Viral RNA was then transfected into HeLa cells (~80% confluency) using Lipofectamine 2000 (11668027, Thermo Fisher). Once cells exhibited ~50% cytopathic effect, cells were scraped and the cell/media suspension was collected. This mixture was then subjected to three rounds of rapid freeze-thaw cycles and centrifuged at 1000×g for 10 minutes to clarify media of cellular debris. Supernatant was used as passage 1 viral stock. The passage 1 viral stock was then overlain onto separate HeLa cells (~80% confluency) to expand the stock into passage 2 viral stock which was used for subsequent experiments.

UVA Treatment on HeLa Cells Infected with Group B Coxsackievirus

HeLa cells were used for four different experiments with enhanced green-fluorescent protein (EGFP)-expressing group B coxsackievirus (EGFP-CVB). In the first experiment, HeLa cells (253,000 per plate) (n=12 plates) were cultured for 24 hours. Half of the EGFP-CVB aliquots were exposed to LED UVA (2000 µW/cm²; peak wavelength of 340 nm) for 20 minutes while the other was not exposed; HeLa cells were then infected with either UVA-exposed or UVA-unexposed virus (MOI=0.1). Six hours later, the supernatant was removed, and the cells were washed twice with 1× sterile PBS (pH=7.0). New DMEM media was added. Plates that were infected with UVA-exposed virus received an additional 20 minutes of UVA (2000 µW/cm$^2$) exposure. Dead cells in the supernatant were collected and quantified 24 hours later. Six plates (3 each of UVA and non-UVA treated) were assessed for live cells. Of the remaining six plates, the 3 plates which had initially been exposed to UVA with a peak wavelength of 340 nm were then exposed to an additional 20 minutes of UVA (2000 µW/cm$^2$). After an additional 24 hours, dead and live cells counts were obtained from the remaining plates.

HeLa Cell Pre-Treatment with UVA on Group B Coxsackievirus Infection

In the second experiment, HeLa cells (235,000 cells) were plated and then incubated in DMEM for 24 hours. The plates were then divided into unexposed controls (n=3) and exposed to LED UVA (2000 µW/cm$^2$; peak wavelength of 340 nm) for 20 minutes (n=3). After another 24 hours, all plates were infected with EGFP-CVB (MOI=0.1). After an additional 24 hours, cells were counted as previous described.

Pre-Treatment of Group B Coxsackievirus with UVA on HeLa Cell Infection

In the third experiment, HeLa cells were cultured for 24 hours and then infected with EGFP-CVB (MOI=0.1). Just prior to infection, half of the EGFP-CVB aliquots were exposed to LED UVA (2000 µW/cm$^2$; peak wavelength of 340 nm) and the other half remained unexposed. Twenty-four hours later, a viable cell count was obtained.

Long-Term UVA Treatment of HeLa Cells During Ongoing Group B Coxsackievirus Infection In this experiment, 250,000 HeLa cells were plated. At 24 hours, cells were divided into three groups. In the first group, cells were infected with EGFP-CVB (MOI=0.1). These cells served as positive infected controls. In group 2, HeLa cells were infected with UVA-treated (2000 µW/cm2 for 20 min; peak wavelength of 340 nm) EGFP-CVB (MOI=0.1) and 6 hours later the infected cells were treated with UVA (2000 µW/cm$^2$; peak wavelength of 340 nm) for 20 minutes followed by 4 additional treatments including day 2 for 20 minutes twice 8 hours apart, and day 3 twice for 20 minutes, 8 hours apart. Group 3 was not infected with EGFP-CVB but was treated 5 times with UVA at the same timepoints used for group 2. This was the non-infected positive control to demonstrate safety of UVA. In all conditions, imaging and cell counts were obtained.

UVA Treatment on Alveolar (A549) Cells Infected with Group B Coxsackievirus

Ideal timepoints of cell death from infection were determined in preliminary experiments with alveolar cells to be 48 hours after infection. In this study, 200,000 alveolar cells were plated and counted at 48 hours (cell count of 754,000). Alveolar cells were then infected with EGFP-CVB (MOI=0.1). Twenty-four hours after infection, the alveolar cell plates were exposed to LED UVA (2000 µW/cm$^2$; peak wavelength of 340 nm) for 0 (control) or 20 minutes (treated) and this was repeated every 24 hours for three days with imaging and cell counts at 96 hours post-infection.

Results

UVA Pre-Treatment of Group B Coxsackievirus Only Prior to Infection of HeLa Cells does not Mitigate Infection In this experiment, half of the plates with HeLa cells were treated with EGFP-CVB and the other half were treated with Group B coxsackievirus that was exposed to ~2000 µW/cm$^2$ LED UVA light with a peak wavelength of 340 nm for 20 minutes. The effect on infection rates at 24 hours were not different between groups.

UVA pre-treatment of HeLa cells prior to Group B coxsackievirus infection does not mitigate viral effects In this experiment, half of the plates with HeLa cells were left untreated and the other half were pre-treated with ~2000 µW/cm$^2$ LED UVA; peak wavelength of 340 nm for 20 minutes with no further UVA treatment. EGFP-CVB was added to both groups. Both groups were equally infected, suggesting that treating HeLa cells before infection did not influence the infection rate.

Figure 27:
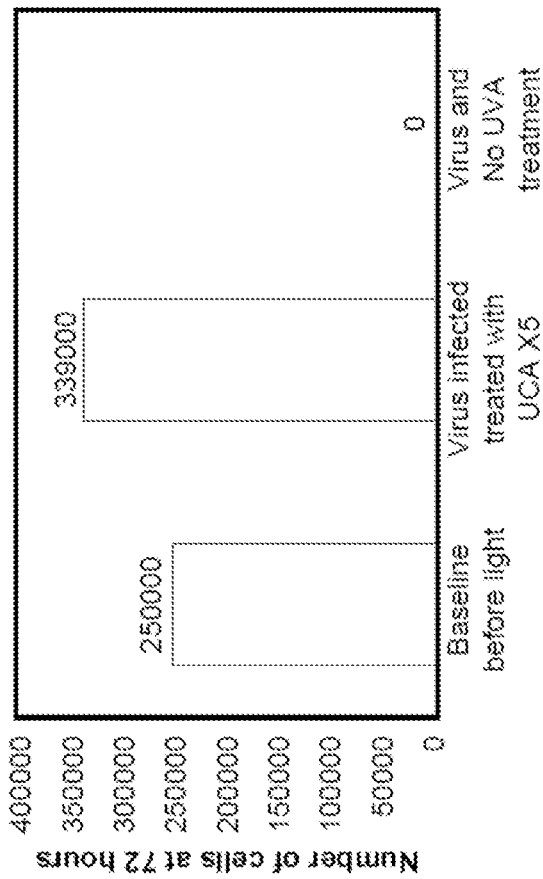
FIG. 27 shows a bar graph showing cell growth infected with a virus during exposure to UV light using an exemplary system.
Figure 28:
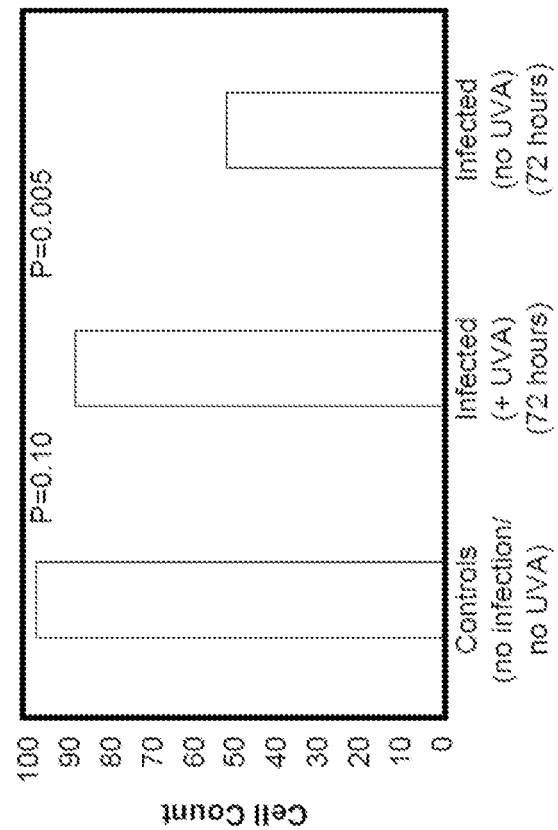
FIG. 28 shows a bar graph showing the cell counts of infected cells after 72 hours of UV light application compared to controls using an exemplary system.

UVA Treatment after Infection with Group B Coxsackievirus Reduced Viral Effect on HeLa Cells In this study, UVA was applied after the HeLa cells were infected with EGFP-CVB. Treated cells were exposed to ~2000 µW/cm$^2$ LED UVA with a peak wavelength of 340 nm at 6 hours post-infection, then twice daily for two additional days, with cell counts at 72 hours post-infection. This was compared to infected but untreated controls. In the treated group, UVA light prevented cell death from EGFP-CVB, with increased cell counts to 339,333 f 60,781 at 72 hours as shown in the bar graph depicted in FIG. 27, compared to no live cells remaining on plates at 48 and 72 hours in untreated controls. Importantly, a third group of HeLa cells that were not infected but received UVA exposure at the same time intervals showed normal cell proliferation, with a cell count of 2,413,333±403,773 at 72 hours.

Additional Experimental Data with GFP Tagged Coxsackie Virus B (EGFP-CVB)

Figure 30:
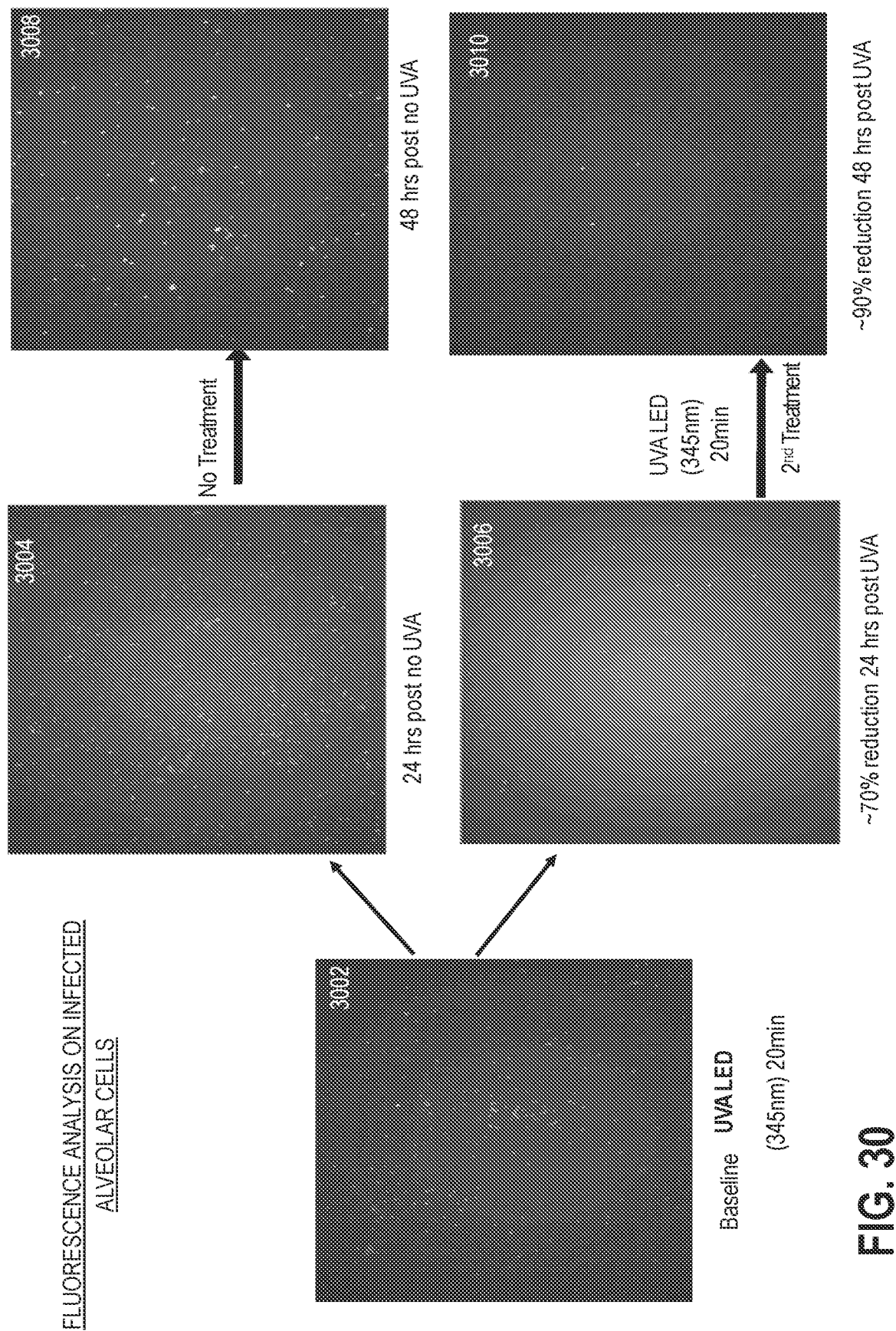
FIG. 30 shows fluorescence images of alveolar cells transfected with Coxsackie virus and effect of UV examples of the invention. Indeed, certain terms may even be emphasized below; however, any terminology intended to be interpreted in any restricted manner will be overtly and specifically defined as such in this Detailed Description section.

Assessment of UVA Treatment by Fluorescence Microscopy Analysis of Alveolar Cells Infected with GFP-CVB (FIG. 30)

Alveolar cells cultured for 24 hours were transfected with GFP-CVB, and fluorescence microscopy was performed after 48 hours to establish baseline (image 3002). The transfected cells were then treated with UVA and imaged at 24 hours (image 3006) and 48 hours (image 3010) post transfection. Control group included GFP-CVB transfected cells but without UVA treatment. The control group without UVA treatment was also imaged at 24 hours (image 3004) and 48 hours (image 3008) post transfection. As can be seen at the images at FIG. 30, UVA treatment resulted in approximately 70 reduction of GFP-CVB infection at 24 hours and approximately 90 reduction of GFP-CVB at 48 hours. UVA treatment was performed with UV LED having peak wavelength at 345 nm and for 20 minutes.

Figure 31:
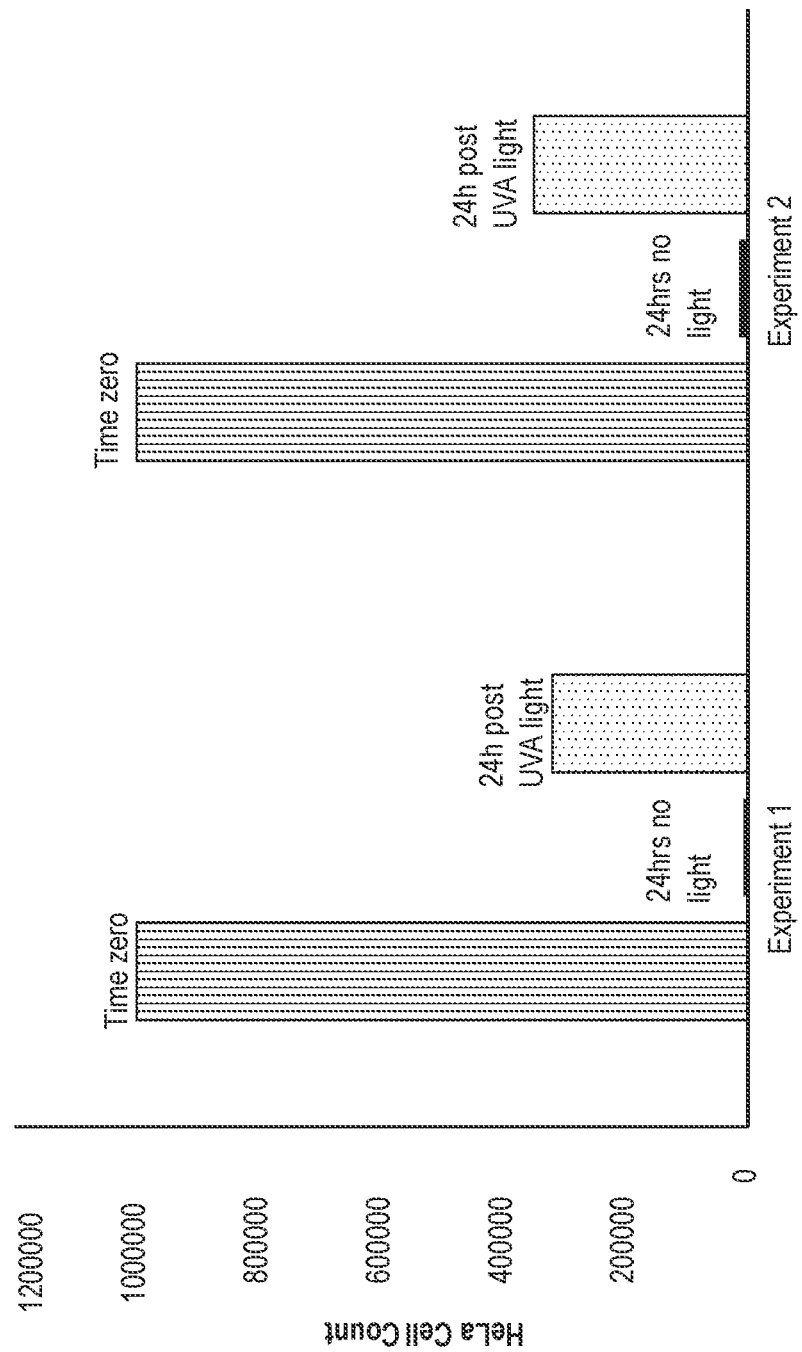

Assessment of UVA Treatment by Quantitative Analysis of HeLa Cells Infected with GFP-CVB (FIG. 31)

HeLa cells cultured for 24 hours were counted prior to transfection with GFP-CVB (time zero at FIG. 31). After transfection, HeLa cells were cultured for 24 hours with GFP-CVB. At 24 hours, UVA treatment was performed on one group. Control group included GFP-CVB transfected HeLa cells without UVA treatment. A final cell count was performed on UVA treated and untreated GFP-CVB transfected HeLa cells. As shown at FIG. 31, HeLa cell survival increased significantly with UVA treatment. Similar to above experiments, UVA treatment was performed with UV LED having peak wavelength at 345 nm for a duration of 20 minutes.

The Effect of UVA Treatment on Alveolar (A549) Cells Infected with Group B Coxsackievirus In alveolar cells infected with EGFP-CVB, cell death was far less than that seen in HeLa cells. At 96 hours post infection, there was clear and widespread infection of cells in the control group. Alveolar cells treated with LED UVA with a peak wavelength of 340 nm also demonstrated infection, but visual assessment suggested a lower rate of infection, with far fewer cells producing viral EGFP signals. In addition, viable cell counts appeared to be higher in the UVA treated group when compared to the untreated group.

Example 5: Coronavirus

In another example, coronavirus infected ciliated tracheal epithelial cells (HTeC) were treated with UV light as disclosed below.

Ciliated tracheal epithelial cells (Promocell, Heidelberg, Germany) were plated (135,000 per plate) into three groups. One group was infected with coronavirus 229E (Cov-229E) (50 uL per plate). In the other group, just prior to infection, coronavirus 229E was treated with LED UVA with a peak wavelength of 340 nm (2000 $\mu W/cm^2$) for 20 minutes. A third group received no infection or UVA. After infection, the cells were treated with UVA (4 cm distance with 2000 $\mu W/cm^2$ at surface of plate with a peak wavelength of 340 nm) for 20 minutes daily. Plates were imaged at 16, 72 and 96 hours, and cell counts were obtained at 72 and 96 hours after infection.

UVA to Salvage Already Infected (with Coronavirus 229E) Ciliated Tracheal Epithelial Cells In this experiment, plates of ciliated tracheal epithelial cells (HTeC) were infected with Cov-229E as above. At 24 hours, plates were divided into two groups. Group 1 was left to continue the infection. In group 2, plates were treated with UVA with a peak wavelength of 340 nm (4 cm distance with 2000 $\mu W/cm^2$ at surface of plate) for 20 minutes. At 48 hours, plates were imaged, and viable cell counts were obtained.

UVA to Treat Coronavirus Infected Ciliated Tracheal Epithelial Cells at Close Range In the anticipation of an endotracheal device using UVA technology, another experiment was conducted identical to the above experiments using lower intensity of light (1300 $\mu W/cm^2$ at the surface of the plate from only 1 cm distance) for 20 minutes daily. This would be the anticipated distance between a light catheter and the tracheal cells in the ventilated patient from the inside of an endotracheal tube.

Level of Coronavirus in Cells with or without UVA Treatment

AllPrep DNA/RNA/Protein Mini Kit (Qiagen) was used to extract total protein from cell samples. Proteins were loaded into a Bolt 4-12% Bis-Tris gel (NW04122 Thermo Fisher) and transferred onto a Biotrace NT nitrocellulose membrane (27376-991, VWR). Total proteins were stained with Ponceau S solution (P7170, Sigma-Aldrich). The membrane was then blocked in blocking solution (tris-buffered saline containing 3% bovine serum albumin (A7030, Sigma-Aldrich) and 0.1% Tween 20 (P1379, Sigma-Aldrich). The membrane was then incubated overnight at 4° C. with either rabbit anti-coronavirus spike protein antibody (1:1000; PA5-81777, Thermo Fisher) or mouse anti-MAVS (mitochondrial antiviral signaling) antibody (1:200; SC-166583, Santa Cruz Biotechnology) diluted in blocking solution. After washing in tris-buffered saline+0.1% Tween 20 (TBS-T), the membrane was then overlain with either horseradish peroxidase (HRP)-conjugated goat anti-rabbit IgG antibody (1:300; 95058-734, VWR) or HRP-conjugated goat anti-mouse IgG antibody (1:300; 5220-0286, SeraCare). The membrane was then washed in TBS-T and subsequently exposed to enhanced chemiluminescence solution (RPN2235, GE Healthcare). Immunoreactive protein bands were imaged using a ChemiDoc Imaging System (Bio-Rad Laboratories, Hercules, CA USA).

LED UVA Light Preserves Ciliated Tracheal Epithelial Cells Infected with Coronavirus 229E Pre-treatment of ciliated tracheal epithelial cells with coronavirus 229E and daily LED UVA (2000 $\mu W/cm^2$; peak wavelength of 340 nm) for 20 minutes was compared to control cells (no UVA and no infection) and cells infected with coronavirus but no UVA exposure. Direct visualization showed definitive changes in cell morphology with infection (no UVA). However, control cells and infected cells treated with daily UVA exhibited similar morphology. At 96 hours, the supernatant was removed and the viable cells (adherent to the plate) were counted. There was no difference in tracheal cell number between control and infected cells treated with UVA. However, there was a marked reduction in viable cells among those infected compared to UVA treated cells (P=0.005) as illustrated in the bar graph shown in FIG. 28.

Figure 29:
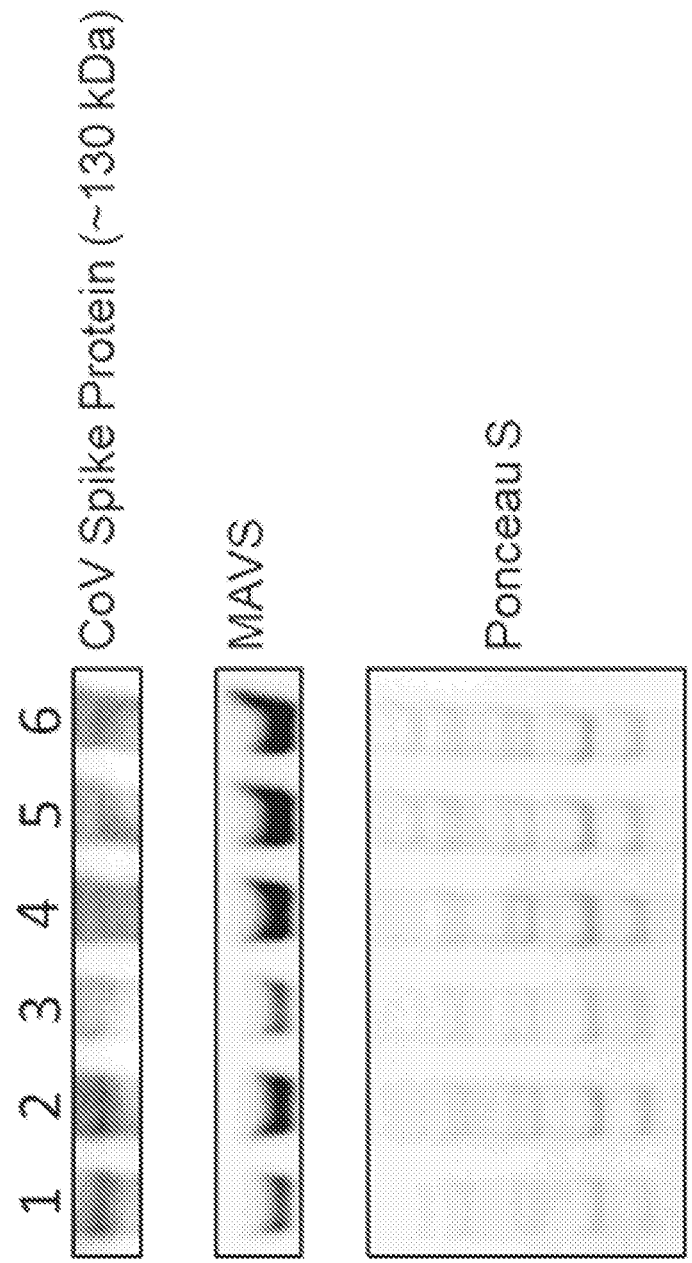
FIG. 29 shows a western blot showing intracellular detection of coronavirus 229E in ciliated tracheal epithelial cells treated with NB-UVA light at 96 hours and levels of Mitochondrial antiviral-signaling protein (MAVS)

Interestingly, infected cells treated with LED UVA revealed decreased Cov-229E spike (S) protein (~130 kDa) when compared to the infected cells not treated. Moreover, the levels infected with Cov-229E and treated with UVA had increased levels of MAVS when compared to cells infected with Cov-229E but not treated with UVA (FIG. 29). Column 1, 2, and 3 in FIG. 29 represent cells transfected with CoV-229E; column 4, 5 and 6 represent cells transfected with CoV-229E and treated with NB-UVA. Ponceau S Stain was used to locate overall protein bands to check the amount of protein loaded on the gel. Accordingly, the experimental data confirms that UV-A light will kill coronavirus 229 E after infecting the epithelial lung tissue, and validates its application in conjunction with ET Tubes and other devices to irradiate the lung tissues as a treatment for coronavirus infected patients.

Figure 32:
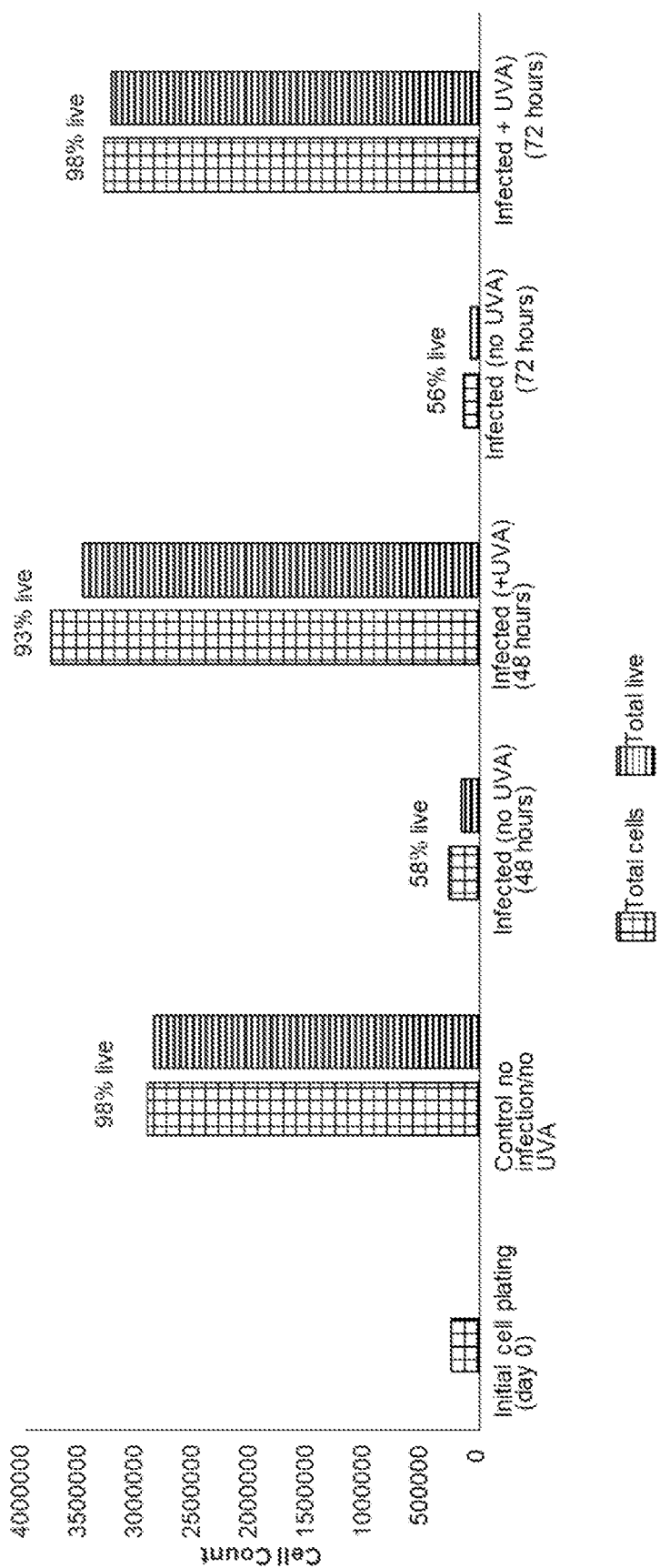
Figure 33:
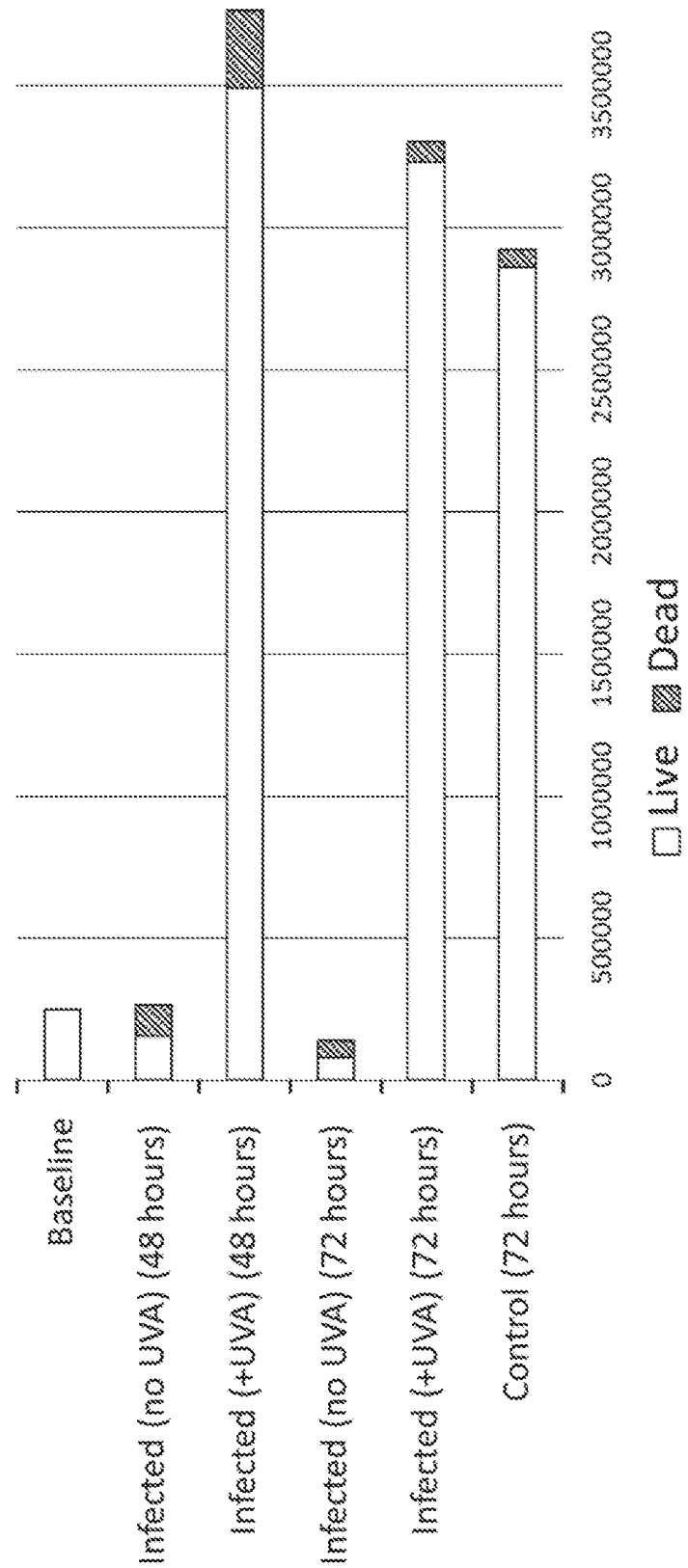

FIGS. 32 and 33 are bar graphs showing the effect of UVA treatment on coronavirus 229E transfected HTeC cells at 48 hours and 72 hours post-UVA treatment compared to untreated controls. As evidenced in FIGS. 33 and 34, UVA treatment increases cell viability of coronavirus 229E transfected HTeC cells.

Additional Embodiments

In one embodiment, an endoscope comprising one or more balloons and one or more UV LEDs or other delivery tube, such as delivery tube 202, may be inserted through the oral cavity through the esophagus into the stomach. In this example, an infection or inflammatory disease in the GI tract may be treated with the UV light sources 222 and one or more balloons selectively inflated to one or more target areas in the stomach, and/or in the small intestine including one or more of deuodenum, jejunum, and ileum.

In an embodiment, a light delivery device for performing intra-luminal light therapy is provided. The light delivery device includes a delivery tube comprising a light emitting portion, the light emitting portion including a plurality of light sources configured to emit narrow-band light at wavelengths in an ultraviolet A (UV-A) range between 335 nm and 349 nm; a plurality of distendable balloons connected to the delivery tube at the light emitting portion, each of the plurality of distendable balloons in fluid communication with a respective inflation port; wherein each of the plurality of distendable balloons is composed of an ultraviolet (UV) transparent material. In a first example of the light delivery device, each of the plurality of distendable balloons are configured to increase irradiance and/or irradiance distribution of light emitted from the plurality of light sources and delivered to a corresponding intra-luminal treatment site. In a second example of the light delivery device, which optionally includes the first example, the plurality of distendable balloons are arranged serially along a length of the light emitting portion; and wherein a separation between any two of the plurality of distendable balloons is adjustable. In a third example of the light delivery device, which optionally includes one or both of the first and the second examples, the light emitting portion comprises one or more segments that are not connected to the plurality of distendable balloons; and wherein the one or more segments include one or more light sources of the plurality of light sources. In a fourth example of the light delivery device, which optionally includes one or more of the first through third examples, the plurality of light sources are light emitting diodes (LEDs) electrically connected to a power source; and wherein the plurality of light sources are configured to emit light outwardly from the delivery device. In a fifth example of the light delivery device, which optionally includes one or more of the first through fourth examples, the plurality of light sources are positioned on a cooling tube within the delivery device, the cooling tube configured to receive cooling air from a cooling system including a medical-grade compressor and a chiller. In a sixth example of the light delivery device, which optionally includes one or more of the first through fifth examples, the plurality of light sources are configured to emit peak wavelengths the UV-A range between 338 nm and 346 nm. In a seventh example of the light delivery device, which optionally includes one or more of the first through sixth examples, the light delivery device further comprises a balloon control unit configured for inflating and/or deflating each of the plurality of distendable balloons via the respective balloon inflation port. In an eighth example of the light delivery device, which optionally includes one or more of the first through seventh examples, the light delivery device further comprises a guide wire channel within the delivery tube and extending throughout a length of the delivery tube, the guide wire channel configured for passing the delivery device over a guide wire positioned within a lumen of a patient. In a ninth example of the light delivery device, which optionally includes one or more of the first through eighth examples, the UV-transparent material is polyether block amide (PEBA) or Cyclic olefin copolymer (COC) or silicone. In a tenth example of the light delivery device, which optionally includes one or more of the first through ninth examples, the plurality of distendable balloons includes at least three balloons.

An embodiment is directed to a method for performing intra-luminal ultraviolet (UV) therapy comprising: providing a UV light delivery device comprising: a delivery tube comprising a plurality of light emitting segments, each of the plurality of light emitting segments including a plurality of light emitting diodes (LEDs) configured to emit narrow-band light having wavelengths in an ultraviolet A (UV-A) range between 338 nm and 346 nm; a plurality of distendable balloons, each of the plurality of distendable balloons coupled to one of the plurality of light segments and each of the plurality of distendable balloons fluidly coupled to a respective inflation port coupled to a balloon control unit; wherein the plurality of distendable balloons are composed of UV transmitting materials; positioning the delivery tube within a lumen of a gastrointestinal (GI) tract of a patient with each the plurality of distendable balloons in a deflated condition; selectively inflating the plurality of distendable balloons via the balloon control unit; and energizing the plurality of LEDs for at a threshold duration and a threshold intensity based on one or more of type and an overall severity of a disorder of the GI tract. A first of the method includes wherein positioning the delivery tube within the lumen comprises aligning one or more of the plurality of distendable balloons with one or more diseased areas within the lumen. In a second example of the method, which optionally includes the first example, selectively inflating the plurality of distendable balloons includes inflating the one or more distendable balloons that align with the one or more diseased areas while maintaining a remaining number of balloons that align with normal healthy tissues in a deflated condition. In a third example of the method, which optionally includes one or both of the first and the second examples, selectively inflating the one or more distendable balloons that align with the one or more diseased areas includes pressurizing the one or more distendable balloons to a threshold pressure at which the one or more distendable balloons contact an epithelial layer of the lumen. In a fourth example of the method, which optionally includes one or more of the first through third examples, the threshold pressure is based on a diameter of the lumen. In a fifth example of the method, which optionally includes the first through fourth examples, during one condition, when one or more target areas have different severities of infection and/or inflammation, for a given light emitting segment, adjusting an amount of light intensity based on a local severity of infection and/or inflammation at the one or more target areas. In a sixth example of the method, which optionally includes the first through fifth examples, the delivery tube includes a coolant tube configured to receive cooling air from a compressor; and further comprising monitoring a temperature of the delivery tube via a thermistor, and adjusting a coolant flow rate through the coolant tube based on the temperature. In a seventh example of the method, which optionally includes the first through sixth examples, the delivery tube is configured as an endoscope comprising one or more cameras for visualizing the lumen. In an eighth example of the method, which optionally includes the first through seventh examples, the UV transmitting material includes polyether block amide (PEBA) or Cyclic olefin copolymer (COC) or silicone. In a ninth example of the method, which optionally includes the first through eighth examples, positioning the delivery tube within the lumen comprises passing the delivery tube over a guide wire positioned within the lumen, the guide wire positioned within the lumen using an endoscope.

Another embodiment is directed to a method of treating, ameliorating, and/or preventing a gastrointestinal disorder in a patient, the method comprising: providing a delivery tube; the delivery tube comprising a light emitting portion including a set of light emitting diodes (LEDs) and at least one distendable balloon coupled to the light emitting portion; navigating a delivery tube into a lumen of a patient's gastrointestinal tract, positioning the at least one distendable balloon to align with a target area in the lumen requiring ultraviolet (UV) light treatment; inflating the at least one distendable balloon via a balloon inflation port fluidly coupled to the at least one distendable balloon; and energizing the set of LEDs connected to the delivery tube and positioned inside the at least one distendable balloon for a duration and an intensity sufficient to treat the gastrointestinal disorder; wherein the set of LEDs are configured to emit narrow-band light having wavelengths in a UV-range between 335 nm and 349 nm. A first example of the method includes wherein the at least one distendable balloon is composed of an UV transmitting material, the UV transmitting material having UV transmittance in a range between eight percent and one hundred percent. In a second example of the method, which optionally includes the first example, the at least one distendable balloon is constructed using a material including polyether block amide (PEBA) or Cyclic olefin copolymer (COC) or silicone. In a third example of the method, which optionally includes one or both of the first and the second examples, inflating the at least one distendable balloon includes pressurizing the at least one distendable balloon to a threshold pressure at which the at least one distendable balloons is in direct contact with a desired surface area of an epithelial layer of the lumen. In a fourth example of the method, which optionally includes one or more of the first through third examples, the threshold pressure is based on a diameter of the lumen. In a fifth example of the method, which optionally includes one or more of the first through fourth examples, the intensity comprises at least 1,100 microwatt/cm$^2$, 1,500 microwatt/cm$^2$, 2,000 microwatt/cm$^2$, 2,100 microwatt/cm$^2$, 2,200 microwatt/cm$^2$, 2,300 microwatt/cm$^2$, 2,400 microwatt/cm$^2$, 2,500 microwatt/cm$^2$, 2,600 microwatt/cm$^2$, 2,700 microwatt/cm$^2$, 2,800 microwatt/cm$^2$, 2,900 microwatt/cm$^2$, 3,000 microwatt/cm$^2$, or 2 milliwatt/cm$^2$. In a sixth example of the method, which optionally includes one or more of the first through fifth examples, the gastrointestinal disorder comprises at least one of: ulcerative colitis, Crohn's disease, pouchitis, proctitis, fistula, inflammatory strictures, microscopic colitis, infections diarrhea, refractory *Helicobater pylori*, MALT lymphoma, colonic inertia, tropical sprue, celiac disease, small intestinal bacterial overgrowth, typhlitis, post-bone marrow transplant infections, pseudopolyps, radiation enteritis, refractory *Clostridium Difficile*, gastrointestinal cancers, hepatobiliary infections, and inflammation and cancers of the mucosa and submucosa. In a seventh example of the method, which optionally includes one or more of first through sixth examples, the gastrointestinal disorder is a form of inflammatory bowel disease. In an eighth example of the method, which optionally includes one or more of first through sixth examples, the form of IBD comprises ulcerative colitis and/or Crohn's disease.

In one embodiment, a UV light treatment assembly comprises a UV light catheter comprising one or more balloons and one or more LEDs. In one non-limiting example, when configured as a single balloon device, the UV light catheter may be approximately 15 cm in length, including a 10 cm segment that contains LED lights and ensheathed by a UV-transparent inflatable balloon. In another non-limiting example, when configured as a multi-balloon device, the UV light catheter may be approximately 100 cm in length, and may include four 10 cm segments of LED lights each ensheathed in a UV-transparent inflatable balloon. The UV lights may be wired on electronic printed circuit boards. Cooled air may be pumped into the catheter inside a cooling tube that will be coiled in-between the LEDs, and will circulate around the lights upon exiting the catheter. The catheter may be flexible, to allow manipulation into the proximal colon using the guidewire technique. Further, the catheter includes a thermistor that detects heat and shuts off the device if it exceeds body temperatures. In some examples, the light catheters may be provided for single-use. The UV light treatment system further comprises a controller including a compressor and a chiller. The controller powers the LED lights, including the timer, and user interface/display. The controller also includes the air chiller/compressor that is configured to pump cooled air into the catheter to mitigate the risk of thermal injury. Further, in some examples, the controller and the compressor/chiller may be housed on a mobile cart, and may be reusable. The UV light treatment system further includes an umbilical assembly. The umbilical includes a flexible tube that connects the controller to the catheter. The flexible tube may house the necessary wiring and tubing to operate the catheter. The umbilical may be reusable.

An advantage of the UV-transparent balloon includes securing the light delivery device in place during light administration, which in turn provides more uniform light exposure to a wider diameter colon, and diffuses extraneous debris/biofilm that may act as a barrier between the light delivery device (that is, the light catheter) and the colonic epithelium, and also, prevents stool from descending into the treatment segment. Furthermore, balloons provide a constant distance between the light source and the target tissue for a uniform exposure dosage. The multiple balloon approach further allows for flexibility of the device when traversing the hepatic and splenic flexures, as well as a customized way of delivering light to just those segments exhibiting inflammation, without exposure to non-inflamed segments, through selective illumination of the ballooned segments correlating with the individual's extent of disease.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the patient matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the patient matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. A light delivery device for performing intra-luminal light therapy, the device comprising:
a delivery tube comprising a light emitting portion, the light emitting portion including a plurality of light sources configured to emit narrow-band light at wavelengths in an ultraviolet A (UV-A) range between 335 nm and 349 nm; and
a plurality of distendable balloons connected to the delivery tube at the light emitting portion, each of the plurality of distendable balloons in fluid communication with a respective inflation port;
wherein each of the plurality of distendable balloons is composed of an ultraviolet (UV) transparent material.

2. The light delivery device of claim 1, wherein each of the plurality of distendable balloons are configured to increase irradiance and/or irradiance distribution of light emitted from the plurality of light sources and delivered to a corresponding intra-luminal treatment site.

3. The light delivery device of claim 1, wherein the plurality of distendable balloons are arranged serially along a length of the light emitting portion; and wherein a separation between any two of the plurality of distendable balloons is adjustable.

4. The light delivery device of claim 3, wherein the light emitting portion comprises one or more segments that are not connected to the plurality of distendable balloons; and wherein the one or more segments include one or more light sources of the plurality of light sources.

5. The light delivery device of claim 1, wherein the plurality of light sources are light emitting diodes (LEDs) electrically connected to a power source; and wherein the plurality of light sources are configured to emit light outwardly from the delivery device.

6. The light delivery device of claim 1, wherein the plurality of light sources are positioned on a cooling tube within the delivery device, the cooling tube configured to receive cooling air from a cooling system including a medical-grade compressor and a chiller.

7. The light delivery device of claim 1, wherein the plurality of light sources are configured to emit peak wavelengths the UV-A range between 338 nm and 346 nm.

8. The light delivery device of claim 1, further comprising a balloon control unit configured for inflating and/or deflating each of the plurality of distendable balloons via the respective balloon inflation port.

9. The light delivery device of claim 1, further comprising a guide wire channel within the delivery tube and extending throughout a length of the delivery tube, the guide wire channel configured for passing the delivery device over a guide wire positioned within a lumen of a patient.

10. The light delivery device of claim 1, wherein the UV-transparent material is polyether block amide (PEBA) or Cyclic olefin copolymer (COC) or silicone.

11. The light delivery device of claim 1, wherein the plurality of distendable balloons includes at least three balloons.

12. A method for performing intra-luminal ultraviolet (UV) therapy comprising:
providing a UV light delivery device comprising:
a delivery tube comprising a plurality of light emitting segments, each of the plurality of light emitting segments including a plurality of light emitting diodes (LEDs) configured to emit narrow-band light having wavelengths in an ultraviolet A (UV-A) range between 338 nm and 346 nm; and
a plurality of distendable balloons, each of the plurality of distendable balloons coupled to one of the plurality of light segments and each of the plurality of distendable balloons fluidly coupled to a respective inflation port coupled to a balloon control unit;
wherein the plurality of distendable balloons are composed of UV transmitting materials;
positioning the delivery tube within a lumen of a gastrointestinal (GI) tract of a patient with each the plurality of distendable balloons in a deflated condition;

selectively inflating the plurality of distendable balloons via the balloon control unit;

and energizing the plurality of LEDs for a threshold duration and a threshold intensity based on one or more of type and an overall severity of a disorder of the GI tract.

13. The method of claim 12, wherein positioning the delivery tube within the lumen comprises aligning one or more of the plurality of distendable balloons with one or more diseased areas within the lumen.

14. The method of claim 13, wherein selectively inflating the plurality of distendable balloons includes inflating the one or more distendable balloons that align with the one or more diseased areas while maintaining a remaining number of balloons that align with normal healthy tissues in a deflated condition.

15. The method of claim 13, wherein selectively inflating the one or more distendable balloons that align with the one or more diseased areas includes pressurizing the one or more distendable balloons to a threshold pressure at which the one or more distendable balloons contact an epithelial layer of the lumen.

16. The method of claim 15, wherein the threshold pressure is based on a diameter of the lumen.

17. The method of claim 12, further comprising: during one condition, when one or more target areas have different severities of infection and/or inflammation, for a given light emitting segment, adjusting an amount of light intensity based on a local severity of infection and/or inflammation at the one or more target areas.

18. The method of claim 12, wherein the delivery tube includes a coolant tube configured to receive cooling air from a compressor; and further comprising monitoring a temperature of the delivery tube via a thermistor, and adjusting a coolant flow rate through the coolant tube based on the temperature.

19. The method of claim 12, wherein the delivery tube is configured as an endoscope comprising one or more cameras for visualizing the lumen.

20. The method of claim 12, wherein the UV transmitting material includes polyether block amide (PEBA) or Cyclic olefin copolymer (COC) or silicone.

21. The method of claim 12, wherein positioning the delivery tube within the lumen comprises passing the delivery tribe over a guide wire positioned within the lumen, the guide wire positioned within the lumen using an endoscope.

22. A method of treating, ameliorating, and/or preventing a gastrointestinal disorder in a patient, the method comprising:

providing a delivery tube; the delivery tube comprising a light emitting portion including a set of light emitting diodes (LEDs) and at least one distendable balloon coupled to the light emitting portion;

navigating the delivery tube into a lumen of a patient's gastrointestinal tract, positioning the at least one distendable balloon to align with a target area in the lumen requiring ultraviolet (UV) light treatment, inflating the at least one distendable balloon via a balloon inflation port fluidly coupled to the at least one distendable balloon; and energizing the set of LEDs connected to the delivery tube and positioned inside the at least one distendable balloon for a duration and an intensity sufficient to treat the gastrointestinal disorder;

wherein the set of LEDs are configured to emit narrowband light having wavelengths in a UV-range between 335 nm and 349 nm.

23. The method of claim 22, wherein the at least one distendable balloon is composed of an UV transmitting material, the UV transmitting material having UV transmittance in a range between eight percent and one hundred percent.

24. The method of claim 22, wherein the at least one distendable balloon is constructed using a material including polyether block amide (PEBA) or Cyclic olefin copolymer (COC) or silicone.

25. The method of claim 22, wherein inflating the at least one distendable balloon includes pressurizing the at least one distendable balloon to a threshold pressure at which the at least one distendable balloons is in direct contact with a desired surface area of an epithelial layer of the lumen.

26. The method of claim 22, wherein the threshold pressure is based on a diameter of the lumen.

27. The method of claim 22, wherein the intensity comprises at least 1,100 microwatt/cm$^2$, 1,500 microwatt/cm$^2$, 2,000 microwatt/cm$^2$, 2,100 microwatt/cm$^2$, 2,200 microwatt/cm$^2$, 2,300 microwatt/cm$^2$, 2,400 microwatt/cm$^2$, 2,500 microwatt/cm$^2$, 2,600 microwatt/cm$^2$, 2,700 microwatt/cm, 2,800 microwatt/cm$^2$, 2,900 microwatt/cm$^2$, 3,000 microwatt/cm$^2$, or 4 milliwatt/cm$^2$.

28. The method of claim 22, wherein the gastrointestinal disorder is a form of inflammatory bowel disease.

29. The method of claim 28, wherein the form of inflammatory bowel disease comprises ulcerative colitis and/or Crohn's disease.

30. The method of claim 22, wherein the gastrointestinal disorder comprises at least one of: ulcerative colitis, Crohn's disease, pouchitis, proctitis, fistula, inflammatory strictures, microscopic colitis, infections diarrhea, refractory *Helicobater pylori*, MALT lymphoma, colonic inertia, tropical sprue, celiac disease, small intestinal bacterial overgrowth, typhlitis, post-bone marrow transplant infections, pseudopolyps, radiation enteritis, refractory *Clostridium difficile*, gastrointestinal cancers, hepatobiliary infections, and/or inflammation and cancers of the mucosa and submucosa.

* * * * *